(12) United States Patent
Sheehan et al.

(10) Patent No.: US 9,086,407 B2
(45) Date of Patent: Jul. 21, 2015

(54) ANALYTE DETECTION

(75) Inventors: Antony James Sheehan, Seaview Downs (AU); Ronald Ian William Osmond, Henly Beach South (AU); Michael Francis Crouch, Hackney (AU); Anthony Ross Dyer, Parkside (AU)

(73) Assignee: TGR BioSciences Pty Ltd., Thebarton, South Australia (AU)

( * ) Notice: Subject to any disclaimer, the term of this patent is extended or adjusted under 35 U.S.C. 154(b) by 47 days.

(21) Appl. No.: 13/436,764

(22) Filed: Mar. 30, 2012

(65) Prior Publication Data

US 2012/0270207 A1      Oct. 25, 2012

Related U.S. Application Data

(63) Continuation-in-part of application No. PCT/AU2010/001517, filed on Nov. 12, 2010.

(60) Provisional application No. 61/470,359, filed on Mar. 31, 2011, provisional application No. 61/470,395, filed on Mar. 31, 2011.

(30) Foreign Application Priority Data

Nov. 12, 2009   (AU) ................................ 2009905550

(51) Int. Cl.
   *G01N 33/543*        (2006.01)
(52) U.S. Cl.
   CPC ................... *G01N 33/54353* (2013.01)
(58) Field of Classification Search
   None
   See application file for complete search history.

(56) References Cited

U.S. PATENT DOCUMENTS

| 5,464,749 | A  | 11/1995 | Schwarzberg et al. |
| 6,531,278 | B1 | 3/2003  | Weimer |
| 6,855,508 | B2 | 2/2005  | Fei et al. |
| 2007/0254322 | A1 | 11/2007 | Romaschin et al. |
| 2009/0215088 | A1 | 8/2009  | Forsyth et al. |
| 2009/0325186 | A1 | 12/2009 | Hinnah et al. |

FOREIGN PATENT DOCUMENTS

| WO | WO-92/21769 A1 | 12/1992 |
| WO | WO-99/64447 A1 | 12/1999 |
| WO | WO-2004/074169 A1 | 9/2004 |
| WO | WO-2007/060523 A1 | 5/2007 |
| WO | WO-2007/079530 A1 | 7/2007 |
| WO | WO-2007/085043 A1 | 8/2007 |
| WO | WO-2007/085044 A1 | 8/2007 |
| WO | WO-2007/115357 A1 | 10/2007 |
| WO | WO-2007/140537 A1 | 12/2007 |
| WO | WO 2008154399    | 12/2008 |

OTHER PUBLICATIONS

Wang et al., Improving the Activity of Immobilized Subtillsin by Site Directed Attachment Through a Genetically Engineered Affinity Tag, Fresenius J Anal Chem 369:280-285, 2001.*
Rosenquist, C. et al., "Serum CrossLaps One Step ELISA, First application of monoclonal antibodies for measurement in serum of bone-related degradation products from C-terminal telopeptides of type I collagen," Clinical Chemistry, vol. 44, No. 11, pp. 2281-2289 (1998).
Katona, E. et al., "A Simple, Quick One-step ELISA Assay for the Determination of Complex Plasma Factor XIII ($A_2B_2$)," Thrombosis and Haemostasis, vol. 83, Issue 2, pp. 268-273 (2000).

* cited by examiner

Primary Examiner — Gary W Counts
(74) Attorney, Agent, or Firm — Jones Day

(57) ABSTRACT

The present disclosure provides methods and/or kits for detecting an analyte in a sample. Some embodiments provide a method for detecting a non-nucleic acid analyte in a sample using a solid substrate comprising a bound immobilization agent and an antibody capture agent and a detectable agent, which can bind to the analyte. The antibody capture agent comprises, at a plurality of sites, a ligand for the immobilization agent. A complex between the analyte, the antibody capture agent and a detectable agent is formed and immobilized on the solid substrate by binding between the immobilization agent and the ligand. In some embodiments, the ligand and the immobilization agent are a binding pair comprising a peptide tag and an anti-peptide tag antibody.

30 Claims, 26 Drawing Sheets

A

ANALYTE DETECTION

CROSS-REFERENCE TO RELATED APPLICATIONS

This application claims the benefit of PCT/AU2010/001517 entitled "Analyte Detection" filed Nov. 12, 2010 and the entire content of this PCT application is hereby incorporated by reference. This application also claims priority from, and hereby incorporates by reference in their entirety, each of the following applications: U.S. provisional patent application 61/470,359 filed 31 Mar. 2011 entitled "Detection of Analytes" and U.S. provisional patent application 61/470,395 filed 31 Mar. 2011 entitled "Improved Immunoassay".

FIELD

The present invention relates to methods for detecting an analyte in a sample.

BACKGROUND

Detection of analytes in samples is important in many industries including, for example, research, immunology, water quality assessment, environmental science and engineering, medicine, etc.

Different methods for detecting analytes in samples may be used including, for example, high pressure liquid chromatography (HPLC), mass spectrometry and enzyme-linked immunosorbent assays (ELISA). While HPLC and mass spectrometry may be used to detect analytes on the basis of charge and/or size, ELISA may be used to detect an analyte based on antigens on the analyte that are recognisable by capture and detection agents (e.g. antibodies, aptamers, etc.), making it an important assay, especially in the life sciences. ELISA may be used to detect the presence, absence or the amount of an analyte in a sample.

While ELISA has become a relatively inexpensive detection method, conventional ELISA takes at least 2 hours to complete and generally includes at least 2 separate incubation and washing steps. Accordingly, it would be desirable to provide a method for detecting an analyte in a sample that takes less time and inputs to perform compared with conventional ELISA, while maintaining or improving the sensitivity of detection.

Reference to any prior art in this specification is not, and should not be taken as, an acknowledgment or any form of suggestion that this prior art forms part of the common general knowledge in any country.

SUMMARY

The present disclosure provides methods and/or kits for detecting an analyte in a sample.

In some embodiments, the present disclosure provides a method for detecting a non-nucleic acid analyte in a sample, the method comprising:
providing a solid substrate comprising a bound immobilisation agent;
providing a capture agent which can bind the analyte, wherein the capture agent comprises, at a plurality of sites, a ligand for the immobilisation agent;
providing a detectable agent which can bind to the analyte;
contacting the sample, capture agent and detectable agent to allow the formation of a complex comprising the analyte, capture agent and detectable agent;
contacting the complex with the solid substrate such that the immobilisation agent may bind the complex via the ligand; and
detecting the presence of immobilised complex on the solid substrate by detection of the detectable agent.

In some embodiments, the present disclosure provides a kit for detecting an analyte in a sample, the kit comprising:
an assay platform comprising a plurality of reaction vessels, one or more of the reaction vessels comprising a bound immobilisation agent;
a capture agent which can bind to an analyte, wherein the capture agent comprises, at a plurality of sites, a ligand for the immobilisation agent;
a detectable agent which can bind to the analyte, wherein the detectable agent comprises a detectable tag; and
instructions for detecting the analyte.

In certain embodiments, the present disclosure provides a method for detecting one or more analytes in one or more samples, the method comprising:
providing one or more samples comprising one or more analytes to be detected;
providing a single assay platform comprising at least two reaction vessels, the at least two reaction vessels comprising a solid substrate comprising the same bound immobilisation agent;
providing one or more capture agents, the one or more capture agents being able to bind to the one or more analytes to be detected and comprising, at a plurality sites, a ligand for the immobilisation agent;
providing one or more detectable agents, the one or more detectable agents being able to bind to the one or more analytes to be detected;
contacting in one or more of the at least two reaction vessels, the one or more samples, the one or more capture agents and the one or more detectable agents to allow the formation of one or more complexes comprising an analyte, a capture agent and a detectable agent;
contacting the one or more complexes with the solid substrate such that the immobilisation agent may bind the one or more complexes via the ligand; and
detecting the presence of one or more immobilised complexes on the solid substrate by detection of the one or more detectable agents.

DETAILED DESCRIPTION

The present invention provides a method for detecting an analyte in a sample, the method comprising:
providing a solid substrate comprising a bound immobilisation agent;
providing a capture agent which can bind the analyte, wherein the capture agent comprises, at a plurality of sites, a ligand for the immobilisation agent;
providing a detectable agent which can bind to the analyte;
contacting the sample, capture agent and detectable agent to allow the formation of a complex comprising the analyte, capture agent and detectable agent;
contacting the complex with the solid substrate such that the immobilisation agent may bind the complex via the ligand; and
detecting the presence of immobilised complex on the solid substrate by detection of the detectable agent.

Conventional sandwich ELISA generally involves binding of a capture antibody to a solid substrate prior to exposure of the capture antibody to an analyte. In conventional ELISAs, the capture antibody is bound or adsorbed to a solid substrate in random orientations. As some of these orientations may mask part, or all, of the analyte binding domain of the capture agent, not all the capture agent bound to the solid substrate may be available for analyte binding, thereby reducing the efficiency of the capture agent and the assay. Furthermore, in some orientations, although the capture agent may still be able to bind to the analyte, subsequent events in the ELISA, such as binding of the detectable agent to the analyte, may be sterically hindered as a result of the orientation of the capture antibody on the solid substrate, thereby reducing the signal generated and hence the sensitivity and efficiency of the assay.

In contrast, the method of the present invention promotes the formation of a complex between a capture agent, an analyte and a detectable agent prior to or concurrent with contacting the complex with the solid substrate.

Without limiting the present invention to any particular mode of action, formation of the complex before or concurrent with binding of the capture agent to the solid substrate is thought to prevent or inhibit binding of the capture agent to the solid substrate in an orientation which is not amenable to analyte binding. Thus, substantially all of the capture agent used may be available for analyte binding. Furthermore, the formation of the complex before or concurrent with binding to the solid substrate may also prevent or reduce steric hindrance of binding between the detectable agent and the analyte, thus promoting increased sensitivity of the method.

In the method of the present invention, the amount of capture agent that binds to the immobilisation agent in an orientation that masks the analyte binding domain, may be reduced relative to conventional ELISA, that is, formation of the complex promotes the capture agent binding to the immobilisation agent in a usable orientation.

As a result of more efficient use of the capture agent (as a result of the complex formation described above), the amount of capture agent that is required to produce a given amount of detectable signal may be reduced relative to conventional ELISA. In addition, more efficient use of the capture agent (as a result of the complex formation described above) may also lead to a reduction in the area of solid substrate required to produce a given level detectable signal relative to conventional ELISA.

In embodiments where a peptide tag is used as a ligand and an anti peptide antibody is used as an immobilisation agent (a peptide/antibody capture system), such a system may provide one or more additional advantages.

For example, it has been determined that a peptide/antibody capture system has advantages over a streptavidin/biotin capture system, as peptide/antibody capture systems may provide one or more of increased signal, reduced variability and reduced interference depending on the sample type.

In addition, in embodiments utilising a reduced number of washing steps of the solid substrate, a peptide/antibody capture system may provide an advantage, particularly in embodiments where the solid substrate is only washed after the complex has been immobilised. Further, in embodiments utilising a reduced time of the assay, a peptide/antibody capture system may also provide an advantage to assist in reducing assay time.

Other advantages of a peptide/antibody capture system are described herein. For example, specific peptides can be designed and prepared that are not naturally occurring, at least for the organism in which an analyte is to be detected. Bioinformatics may be used to select sequences that are unique.

Different peptides may also be selected for different applications or assays. As such, they are readily expandable if more than one affinity system is required. For example, in embodiments relating to the detection of an analyte in different wells of an assay plate, each well may be coated with a specific subset of anti-peptide antibodies which would allow the specific immobilisation of particular capture antibodies from a mixture of such antibodies with different peptide tags.

Further, in some embodiments the use of a peptide/antibody capture system may provide one or more advantages over other types of capture systems. For example, the use of a peptide/antibody system in certain embodiments may also provide an advantage over capture systems utilising poly-charged ligands (for example His tags) and metal ions (for example $Ni^{2+}$ ions), as the peptide/antibody system may have greater affinity and/or be less likely to be affected by the presence of other charges molecules. Similarly, the use of a peptide/antibody system in certain embodiments may provide an advantage over glutathione/GST systems in that the peptide/antibody capture system also has greater affinity.

A peptide/antibody capture system may also provide in some embodiments one or more advantages over the use of anti-species antibodies as an immobilisation agent, since the system is then not restricted to the use of species of antibodies immobilised on the surface. For example, an anti-rabbit immobilised antibody can only be used to bind to rabbit capture antibodies. In addition, anti-species antibodies may suffer from reduced specificity to the species of antibody they are designed to bind, which may minimize their utility in assays using samples containing endogenous antibodies such as serum and plasma, as these will block the binding of assay antibodies.

Further, a peptide/antibody capture system may also provide in some embodiments one or more advantages over capture systems utilising immobilised protein A and/or protein G capture systems. For example, proteins A and G will bind many antibodies in a solution. Protein A and protein G may also demonstrate reduced utility in samples containing endogenous antibodies, such as serum or plasma, as these will block binding of antibodies. In addition, such a capture system may have disadvantages in embodiments where both the capture agent and the detectable agent are antibodies, since Protein A or Protein G will not discriminate between the capture and detection antibodies, and will bind both, therefore eliminating the assay discrimination for analyte.

As the method allows detectable signals to be produced with less capture agent and/or reduced solid substrate surface area relative to conventional ELISA, the method may be particularly suitable for microfluidic systems, where miniaturisation of structures and minimisation of reagents used is desirable. Accordingly, in some embodiments, the method may be performed in a microfluidic system.

Microfluidics deals with the behaviour, precise control and manipulation of fluids that are geometrically constrained to a small, typically in the low millimeter, or sub-millimeter scale. The behaviour of fluids at the microscale can differ from 'macrofluidic' behaviour in that factors such as surface tension, energy dissipation, and fluidic resistance start to dominate the system. At small scales (channel diameters of around 100 nanometers to several hundred micrometers) fluids exhibit specific properties. For example, the Reynolds number (which compares the effect of momentum of a fluid to the effect of viscosity) can become very low. A key consequence of this is that fluids, when side-by-side, do not necessarily mix in the traditional sense; molecular transport between them must often be through diffusion. Furthermore, high specificity of chemical and physical properties (concentration, pH, temperature, shear force, etc.) can also be ensured resulting in more uniform reaction conditions and higher grade products in single and multi-step reactions.

In addition, as set out above, in microfluidic systems, the surface area available for surface-based reactions, such as the formation of an immobilised complex on a surface, may be limited, thus making the method of the present invention particularly suited to microfluidic systems.

In light of the above, a "microfluidic system" as referred to herein refers to where the method of the present invention is at least partially performed in a reaction vessel comprising one or more chambers or channels in which the narrowest dimension is less than 3 mm, less than 2 mm or less than 1 mm. Alternatively, or in addition, a microfluidic system may also include any reaction which occurs in a total reaction volume of less than 20 µl, less than 10 µl, less than 5 µl or less than 1 µl. Examples of microfluidic systems may include, for example, microfluidic "lab-on-a-chip" type devices; high density microtitre plates, such as 1536, 3456 or 9600 well microtitre plates; microarrays and the like.

As described above, in some embodiments, the complex comprising the analyte, capture agent and detectable agent is formed prior to binding between the immobilisation agent and the ligand. In some embodiments, the complex may be formed by sequential or concurrent addition of the capture agent and detectable agent to the analyte prior to contacting the complex with the immobilisation agent on the solid substrate.

In some embodiments, the complex comprising the analyte, capture agent and detectable agent is formed concurrent with binding between the immobilisation agent and the ligand. For example, the complex may be formed by adding the capture agent, detectable agent and the analyte to the solid substrate. In some embodiments, the complex may be formed in part (e.g. analyte+capture agent or analyte+detectable agent) before it is contacted with the solid substrate and the capture agent or detectable agent.

The time taken to perform a method for detecting an analyte in a sample is an important consideration in industry. In this regard, conventional ELISA can be time-intensive. For example, it is not uncommon in a conventional ELISA for incubation steps to be performed after the addition of each individual component of the ELISA (e.g. the capture antibody, the analyte and the detection antibody). In some embodiments, the present invention minimises the number of incubation steps, as the complex of the capture agent, the analyte and the detectable agent may be formed prior to or concurrent with binding to the solid substrate. Accordingly, in some embodiments, only a single incubation step may be required.

As a result of the multiple incubation steps and sequential addition of components, conventional ELISA generally also requires multiple wash steps to remove unbound components after each incubation step. For example, it is not uncommon in a conventional ELISA for washing steps to be performed after binding of a capture antibody to a solid substrate, after addition of an analyte and after addition of a detection antibody. In some embodiments, the method of the present invention allows the number of washing steps to be reduced compared with conventional ELISA. For example, as the capture agent, analyte and detectable agent may be added to the solid substrate at the same time, intermediate washing steps may be avoided. The reduced number of washes may allow the method to be performed in a simpler and more time-efficient manner. Furthermore, in some embodiments, the reduced number of washes allows the method to be used for capture agents that may have a low binding affinity to the analyte, as the reduced amount of washing may reduce or eliminate dissociation between the capture agent and the analyte.

In some embodiments, reducing the number of incubation steps and/or washing steps that are required may allow the duration of the complex to solid substrate binding step to be maximised without increasing the total duration of the method. Increasing the duration of the complex to solid substrate binding step may increase the sensitivity of the method.

Notwithstanding, in some embodiments, it may be desirable to wash unbound components from the solid substrate after the complex has bound to the solid substrate. Accordingly, in some embodiments, the solid substrate may be washed prior to detection of the detectable agent. Washing the solid substrate prior to detection of the detectable agent allows the removal of unbound detectable agent, which can decrease the level of background signal and hence improve the sensitivity of the ELISA. Methods for washing steps are known in the art and generally involve repeated addition and removal of buffer. For example, washing steps may be performed as described in Moore et al. *AIDS* 3(3): 155-163, 1989.

As set out above, the method comprises providing a solid substrate comprising a bound immobilisation agent. In this regard, the solid substrate comprising the bound immobilisation agent may be any suitable substrate for binding the immobilisation agent and permitting detection of the detectable agent. The solid substrate may, for example, comprise a surface of a multi-well plate (e.g. a microtitre plate), a multi-well strip, a bead, a dip stick, a microfluidic device, etc.

In some embodiments, the use of the bound immobilisation agent on the solid substrate provides flexibility in the selection of the substrate that may be used. For example, the immobilisation agent may allow a particular capture agent to bind to a substrate (via the immobilisation agent) to which it would otherwise not bind. Moreover, the use of an immobilisation agent-ligand binding pair allows the method to be modular in that a range of capture agents may be produced that bind to a particular solid substrate by incorporation of a ligand for the immobilisation agent on the solid substrate into the capture agents.

In some embodiments, the solid substrate may comprise a substance that promotes binding of the immobilisation agent or may be treated to promote binding of the immobilisation agent. In some embodiments, the solid substrate may comprise a plastic surface including, for example, a polystyrene surface, a polyvinyl chloride surface or a cyclo-olefin surface. In some embodiments, the solid substrate may be transparent or coloured depending whether the detection method involves a colorimetric, fluorescence or other read out.

In some embodiments, the solid substrate may comprise a hydrophobic surface.

In some embodiments, the solid substrate may be treated to increase the binding affinity of the immobilisation agent to the solid substrate. For example, the solid substrate may be irradiated or functionalised to allow covalent bonding between the substrate and the immobilisation agent.

As described above, the solid substrate comprises a bound immobilisation agent which is capable of binding a ligand on the capture agent. As can be appreciated, a range of different immobilisation agent and ligand binding pairs may be used. In some embodiments, the immobilisation agent and ligand may be interchangeable (i.e. a first compound may be bound to the solid substrate or the capture agent and a second compound, which is part of the same binding pair, may be bound to the other).

In some embodiments, the immobilisation agent and ligand binding pairs may comprise, for example: biotin and avidin or streptavidin (or derivates thereof); a metal chelate (e.g. copper, nickel, cobalt) and Histidine (e.g. histidine tagged proteins); maleic anhydride and amine (e.g. amine containing proteins); or meleimide and sulfhydryls (e.g. sulfhydryl peptides); a FLAG-tag and an anti-FLAG antibody; and the like.

In some embodiments, the immobilisation agent comprises avidin, streptavidin or derivatives thereof and the ligand comprises biotin or derivates thereof. Derivatives of avidin or streptavidin are known in the art and may include forms of avidin or streptavidin that have been modified to increase their binding affinity to modified and/or unmodified solid substrates or ligands. For example, streptavidin may be modified to add one or more amine groups, histidine residues or sulfhydryl groups to the molecule. In some embodiments, the derivative of streptavidin may comprise neutravidin, captavidin or streptavidin mutants (e.g. H127C or S139C).

In some embodiments, where a FLAG-tag is used as a ligand in the method of the present invention (see later), the corresponding immobilization agent may comprise an anti-FLAG antibody. Reference herein to an "antibody" may include, for example, monoclonal antibodies, polyclonal antibodies, multivalent antibodies, chimeric antibodies, multispecific antibodies, and antibody fragments that exhibit the desired binding specificity to a FLAG-tag. A range of anti-FLAG antibodies could be readily obtained or produced by a person skilled in the art. However, by way of example, commercially available anti-FLAG antibodies include Sigma-Aldrich product codes F7425, F3040, F1804, F3165, F4042, F2555 and SAB4200071. Some commercially available antibodies recognize the FLAG-tag only in certain positions on a protein, e.g. exclusively N-terminal. However, other available antibodies are position-insensitive.

In some embodiments, hydrophobic or hydrophilic immobilisation agents may be passively bound to the hydrophobic or hydrophilic solid substrates, respectively. For example, streptavidin (or derivates thereof) may be passively bound to a hydrophobic solid substrate. In some embodiments, the solid substrate may comprise a linker which facilitates covalent bonding of the immobilisation agents to the solid substrate. For example, the linker may comprise glutathione, maleic anhydride, a metal chelate, or meleimide. The immobilisation agent may then be bound to the solid substrate via the linker.

In some embodiments, the solid substrate comprising the bound immobilisation agent may be treated with a blocking agent that binds non-specifically to and saturates binding sites to prevent unwanted binding of ligand or other components (e.g. the analyte, capture agent or detectable agent) to the excess sites on the solid substrate. In some embodiments, a blocking agent may be included during the binding reactions (e.g. bovine serum albumin (BSA), or the like, may be included during the formation of the complex). Examples of blocking agents may include, for example, gelatin, BSA, egg albumin, casein, and non-fat milk. In some embodiments, the solid substrate and/or the bound immobilisation agent may be treated with the blocking agent prior to the addition of the capture agent or concurrent with the addition of the capture agent.

While a single step ELISA has been previously described in Kumada et al. (*Journal of Biotechnology* 127: 288-299, 2007), such an assay suffers from an inability to adequately block the solid substrate, particularly when the capture agent has a low binding affinity to the analyte. Inadequate blocking can result in non-specific binding of proteins to the capture agent or the solid substrate, which can reduce the efficiency of the assay and/or create false or variable signals. Assays such as those described in Kumada therefore require a trade-off between specificity and sensitivity and the assay may not be suitable for many samples and analytes.

In contrast, the utilisation of an immobilisation agent bound to the solid substrate according to the present invention may allow for adequate blocking of the solid substrate without compromising the sensitivity of the method. In some embodiments, the method may be suitable for high specificity detection of an analyte using a capture agent with a low binding affinity for the analyte.

The ELISA disclosed in Kumada is also limited in relation to the protein concentration that may be present in a sample. For example, as described in Kumada, the immobilisation yield of the capture agent (GST-PS19 or wild-type GST) to a hydrophobic plate drops off significantly in the presence of a BSA concentration in excess of 0.001 mg/ml. Indeed, in the presence of a BSA concentration of 0.1 mg/ml, the immobilisation yield of the capture agent is only around 20%. Similar effects were observed for the immobilisation of wild-type GST to hydrophilic plates. The assay disclosed in Kumada is therefore not suitable for samples with moderate to high levels of proteins (e.g. samples comprising serum or cell lysates).

In at least some embodiments, the method of the present invention is not so limited. For example, in some embodiments, the utilisation of the immobilisation agent allows the method to be performed in the presence of moderate or high protein concentrations. Moderate or high protein concentrations may be introduced during blocking steps (as set out above) or may be included in the sample itself. For example, the sample may comprise a serum sample which may have a protein concentration up to approximately 60-80 mg/ml, a cell lysate sample which may have a protein concentration of approximately 1-3 mg/ml, or a sample from a cell-based assay which may include protein contamination from fetal bovine serum (FBS), or the like, which may be used in cell culture media. Protein contamination from media may account for 1-5% of the final protein contamination in a cell lysate, which may translate to approximately 0.6-4 mg/ml of protein in addition to the cellular protein.

Accordingly, in some embodiments, the sample may comprise a protein concentration of more than 0.01 mg/ml, a protein concentration of more than 0.1 mg/ml, a protein concentration of more than 1 mg/ml, a protein concentration of more than 2 mg/ml, a protein concentration of more than 10 mg/ml, or a protein concentration of more than 60 mg/ml.

Furthermore, as the immobilisation agent is attached to the solid substrate, and the capture agent comprises a ligand for the immobilisation agent, the potential influence of substrate-reactive proteins in the sample may be substantially negated. For example, hydrophobic proteins in the sample are not likely to affect the outcome of the method even if it is performed on a hydrophobic solid substrate as the immobilisation agent is already bound to the solid substrate and the ligand on the capture agent is specific for the immobilisation agent.

As described above, the capture agent comprises, at a plurality of sites, a ligand for the immobilisation agent. In some embodiments, the ligand may be a part of the capture agent. For example, the capture agent may comprise histidine residues, amine groups or sulfhydryl groups that are able to bind to the immobilisation agent.

In some embodiments, the ligand may be bound to the capture agent. For example, in some embodiments, the ligand may be amine reactive, carbohydrate reactive, carboxyl reactive, or sulfhydryl reactive and thus may bind to the capture agent via primary amines (e.g. lysine or the N-terminus), carbohydrate modifications, carboxyl groups (e.g. on aspartic acid residues, glutamic acid residues and the C-terminus), or sulfhydryl groups. In some embodiments, the ligand may comprise iodinatable and/or photoactivatable groups. For example, in embodiments whereby the capture agent comprises RNA or DNA, the ligand may comprise aryl azide groups that may be converted to highly reactive aryl nitrene when exposed to strong visible light or psoralen groups that react with thymine- and other pyrimidine-containing bases when activated to form covalent bonds (e.g. the ligand may comprise 1-[4-Azidosalicylamido]-6-[biotinamido]-hexane or Psoralen-PEG3-Biotin). In some embodiments the ligand may comprise tetrafluorophenyl azide (TFPA) groups that, once activated by UV light, are able to covalently bind at sites containing C—H or N—H bonds (e.g. the ligand may comprise TFPA-PEG3-Biotin). Methods for labelling proteins, RNA, DNA and other molecules with the above ligands are generally known in the art and may include methods described by Wong (*Chemistry of Protein Conjugation and Cross-Linking*, CRC Press LLC, 1991).

In some embodiments, the ligand comprises biotin or a derivative thereof including, for example, iminobiotin, D-desthiobiotin, DSB-X-biotin, biotin dimers or arylstannylbiotin trimer. Biotin and derivatives thereof may be bound to the capture agent by biotinylation. Biotinylation reagents and methods for biotinylation of a target molecule are known in the art and include those described by Hermanson (*Bioconjugate Techniques*, Academic Press, 2008). Biotinylation may comprise, for example, primary amine biotinylation, sulfhydryl biotinylation, carboxyl biotinylation, or glycoprotein biotinylation. Advantages of biotin or derivatives thereof for labelling the capture agent are the availability of commercial kits, ease of labelling and the ability to label the capture agent at a plurality of sites.

In some embodiments, the ligand for the immobilisation agent comprises a FLAG-tag. FLAG-tag, or FLAG octapeptide, is a polypeptide protein tag that can be conjugated to a protein (such as an antibody) or added to a protein using Recombinant DNA technology. A FLAG-tag can be used in many different assays that require recognition by an antibody. Adding a FLAG-tag to a protein allows the protein to be bound and/or immobilised by an antibody against the FLAG sequence. The peptide sequence of the FLAG-tag is DYKDDDDK (SEQ ID NO: 1). In some embodiments, a FLAG-tag may also be used in conjunction with other affinity tags for example a polyhistidine tag (His-tag), HA-tag or myc-tag. The FLAG-tag was the first example of a fully functional epitope tag to be published in the scientific literature (see Hopp et al., *Bio/Technology* 6: 1204-1210, 1988). Its structure has been optimized for compatibility with the proteins it is attached to, in that it is more hydrophilic than other common epitope tags and therefore less likely to denature or inactivate proteins to which it is appended. In addition, it can be removed readily from proteins by treatment with the specific proteinase, enterokinase (Enteropeptidase).

In addition to comprising a ligand for the immobilisation agent at a plurality of sites, the capture agent must be capable of binding to the analyte. In some embodiments, the capture agent may comprise an antibody, an aptamer, or a protein receptor or ligand (or binding fragment thereof). Similarly, in some embodiments, the detectable agent which can also bind to the analyte may comprise an antibody, an aptamer, or a protein receptor or ligand (or binding fragment thereof).

Reference herein to an "antibody" may include, for example, monoclonal antibodies, polyclonal antibodies, multivalent antibodies, chimeric antibodies, multispecific antibodies, and antibody fragments that exhibit the desired binding specificity. Antibodies to specific analytes may be obtained commercially or generated by methods known in the art. For example, antibodies to specific analytes may be prepared using methods generally disclosed by Howard and Kaser (*Making and Using Antibodies: a Practical Handbook*, CRC Press, 2007).

Aptamers used as the capture agent or detectable agent may be obtained commercially or generated by methods known in the art. For example, aptamers to specific analytes may be prepared using methods generally disclosed by Mascini (*Aptamers in Bioanalysis*, John Wiley & Sons Inc, 2009).

Protein receptors or ligands that may be used as the capture agent or detectable agent may comprise the whole receptor or ligand or a fragment thereof (e.g. a fragment comprising a binding domain of the receptor or ligand). In some embodiments, the receptor or ligand (or fragment thereof) may comprise a fusion protein. Fusion partners may include, for example, fluorescent fusion partners (e.g. GFP), immunoglobulin fusion partners, etc. Fusion partners and methods for preparing fusion proteins are known in the art and may include those described by Sambrook and Russell (*Molecular Cloning: A Laboratory Manual*, Volume 3, Cold Spring Harbor Laboratory Press, 2001). In some embodiments, the fusion partner may act to stabilise the receptor or ligand (or fragment thereof), provide a detectable signal (e.g. for fluorescent fusion partners) or provide a target for antibody, or other, binding or immobilisation.

In some embodiments, the detectable agent may comprise a detectable tag. In some embodiments, the detectable tag may be applied to the detectable agent (e.g. bound to the detectable agent) or may be part of the detectable agent (e.g. the detectable agent may include the detectable tag as a fusion partner, a labelled amino acid or labelled nucleotide).

Examples of suitable detectable tags include antigens, enzymes, fluorophores, quenchers, radioactive isotopes, luminescent labels, nucleic acids capable of PCR amplification and the like. It will be appreciated that the detectable tag may be detected directly or indirectly via a further molecule that can produce a detectable signal.

Antigens that may be used as a detectable tag may include, for example, any antigenic component of the detectable agent that may be targeted by a secondary detectable agent. For example, in some embodiments, a secondary antibody may be used to detect an antigen on a detectable agent. The secondary antibody may, for example, be fluorescently or enzymatically labelled. In embodiments where the detectable agent is a primary antibody (ie. an analyte binding antibody), the secondary antibody may have binding affinity to an antigen on the primary antibody. For example, the antigen may be derived from the host in which the detectable agent was raised.

Enzymes that may be used as detectable tags include, for example, enzymes that result in the conversion of a substrate into a detectable product (generally resulting in a change in colour or fluorescence or generation of an electrochemical signal). Such enzymes may include, for example, horseradish peroxidase (HRP), alkaline phosphatase (AP), β-galactosidase, acetylcholinesterase, luciferase, or catalase. Depending on the enzyme and substrate used, detection may be performed with a spectrophotometer, fluorometer, luminometer, electrochemical detection means.

Radioactive isotopes that may be used as detectable tags include, for example, $^{3}H$, $^{14}C$, $^{32}P$, $^{35}S$, or $^{131}I$. The radioisotope may be conjugated to a detectable agent or incorporated into a detectable agent by translation of mRNA encoding the detectable agent in the presence of radiolabelled amino acids. Radioisotopes and methods for conjugating radioactive isotopes to molecules such as proteins are known in the art and include methods discussed by Slater (*Radioisotopes in Biology: A Practical Approach*, Oxford University Press, 2002). Radioisotopes may be detected using gamma, beta or scintillation counters.

Fluorophores that may be used as detectable tags include, for example, resorufin, fluorescein (fluorescein isothiocyanate, FITC), rhodamine (tetramethyl rhodamine isothiocyanate, TRITC), green fluorescent protein (GFP), phycobiliproteins (allophycocyanin, phycocyanin, phycoerythrin and phycoerythrocyanin, or derivatives of any of the foregoing). In some embodiments, the detectable tag may be part of the detectable agent (e.g. in the form of a fusion protein or a protein comprising fluorescent amino acids). Fluorophores may be subjected to applied stimulation (e.g. light of a suitable excitation wavelength) to promote fluorescence.

Alternatively, stimulation may be provided by a fluorescence resonance energy transfer (FRET) partner (i.e. a donor molecule). When the fluorophore comes into close vicinity to the FRET partner (e.g. during formation of the complex), the fluorophore may become excited by the FRET partner and fluoresce (i.e. the fluorophore is an acceptor molecule). FRET donors may include luminescent and/or fluorescent agents.

In some embodiments, the detectable tag may comprise a quencher. Quenchers are able to absorb excitation energy from fluorophores and may be used to suppress the fluorophore's emission when in close proximity. In this regard, the reaction is similar to a FRET reaction, except that the readout is a loss of fluorescence.

In embodiments which use a quencher or FRET fluorophore as the detectable tag, an interacting quencher or fluorophore may be provided on, or integrated with, the solid substrate and/or capture agent. For example, in embodiments where the detectable tag is a fluorophore, the substrate or capture agent may include a FRET partner (either donor or acceptor) or a quencher. Conversely, in embodiments where the detectable tag is a quencher, the solid substrate or capture agent may include a suitable fluorophore. Detection of an analyte in a sample may then be determined by a loss or gain in fluorescence via interaction between the fluorophore and quencher or between the FRET donor and acceptor.

In some embodiments, detecting the presence of the immobilised complex on the solid substrate may utilise time-resolved fluorescence (TRF) and FRET technologies. For example detecting the presence of the immobilised complex on the solid substrate may involve a TRF-FRET technology as described in EP 569,496, U.S. Pat. No. 5,527,684 or U.S. Pat. No. 6,861,264.

In some embodiments, the detectable tag may comprise a bead that comprises a quencher, fluorophore, or FRET donor or acceptor. In some embodiments, the solid substrate and detectable agent may comprise labelled beads which interact via FRET.

In some embodiments, the solid substrate and detectable agent may comprise labelled beads as part of a chemical transfer proximity based assay such as the SureFire® detection assay described by Osmond et al. (*J. Biomol. Screen.* 10(7): 730-737, 2005).

Luminescent compounds that may be used as detectable tags include, for example, chemiluminescent and bioluminescent compounds. These compounds may be used to label the detectable agent. The presence of the chemiluminescent-tag may be determined by detecting the presence of luminescence that arises during the course of a chemical reaction. Examples of useful chemiluminescent labelling compounds are luminol, isoluminol, theromatic acridinium ester, imidazole, acridinium salt and oxalate ester. Bioluminescence is a type of chemiluminescence found in biological systems in which a catalytic protein increases the efficiency of the chemiluminescent reaction. The presence of a bioluminescent antibody is determined by detecting the presence of luminescence. Examples of bioluminescent compounds include luciferin, luciferase and aequorin.

Nucleic acids that may be used as detectable tags include any suitable nucleic acid that is capable of PCR amplification and/or hybridisation to a probe. Preferably the nucleic acid is of a length sufficient to allow binding of a forward and/or a reverse primer. The nucleic acid tag may be included in an aptamer or bound to a protein. Bound complex may be detected by performing a PCR reaction, whereby the nucleic acid tag is amplified and measured, or using a labelled nucleic acid probe with a complementary sequence to at least a portion of the nucleic acid tag. Methods of preparing and binding detectable nucleic acid tags to capture agents or detectable agents (e.g. proteins) are known in the art and include methods described in US 2009/0053701.

As set out above, the present invention provides a method for detecting an analyte in a sample.

In some embodiments, the method for detecting an analyte in a sample may comprise a qualitative determination of whether the analyte is present or absent in the sample. In some embodiments, the method may comprise a quantitative assessment of the levels of the analyte in the sample.

The sample may be any mixture, composition, solution, etc. that may or may not contain an analyte. In some embodiments, the sample may comprise a laboratory sample, medical sample, water sample, food sample, agricultural sample, etc. As described above, in some embodiments, the sample may comprise a serum sample, a serum containing sample or a cell lysate.

In some embodiments, the sample may be pretreated before being used in the method (i.e. the sample may be precleared, concentrated, diluted, or processed to remove one or more components or impurities from the sample using methods known in the art).

The analyte may be any analyte in a sample against which an antibody, aptamer or other capture agent and detectable agent are able to bind. For example, the analyte may comprise a microbe, a virus, a protein, a nucleic acid, a macromolecule, a small molecule, a drug, etc. In some embodiments, the analyte comprises a protein.

In some embodiments, the analyte may comprise a particular form or state of a protein or other molecule. For example, in some embodiments, the method may be used to detect a protein that is phosphorylated, methylated, glycosylated, etc. In these embodiments, at least one of the capture agent and the detectable agent should have specificity to only one form of the protein (e.g. the capture agent may only bind to the phosphorylated form of the protein and not to the unphosphorylated form of the protein).

In some embodiments, the analyte may comprise a phosphoprotein. A range of phosphoproteins are known including, for example, phosphorylated ERK, S6 p240/44, AKT pT308 or AKT pS473. In some embodiments, the binding site of at least one of the capture agent and the detectable agent comprises a phosphorylation site binding domain. At least one of the capture agent and the detectable agent may be specific for the phosphorylated or unphosphorylated form of the protein.

Some embodiments of the present disclosure are directed to methods and/or kits for detecting an analyte in a sample that have one or more combinations of advantages. For example, some of the advantages of the methods and/or kits disclosed herein include: reducing the time taken to detect the analyte; reducing the number of incubation steps; reducing the number of step and/or duration for washing of the solid substrate; providing reliable performance; eliminating the need for pre-incubation; reducing the number of dispensing steps; reducing the number of aspiration steps; providing a simple easy to use assay; being suitable for microfluidic systems and/or other automated systems; reducing costs in materials; reducing costs in time needed to perform the assay; reducing handling costs; reducing handling errors; reducing the cost of the materials needed; measuring different analytes on one plate; being compatible for use with most standard plate readers; providing improved sensitivity; ability to tolerate samples with moderate to high levels of proteins; allowing the use of antibodies that have a low binding affinity to an analyte; improving the ability to detect analytes in a variety of biological milieu; allowing the use of lower concentration of antibodies to an analyte; and providing kits and/or assay platforms (such as microtitre plates) that are easy to manufacture and/or less costly to manufacturer.

For example, the methods and/or kits of the present disclosure may result in improvement in the number of handling and/or washing steps required during an assay. In addition, the methods and/or kits of the present disclosure may in some embodiments result in an improvement in the time required to reliably detect the analyte.

Further, the improvements in handling and washing provide a number of advantages over previous assays, for example assays for detecting an analyte utilising an antibody (or an antigen binding part thereof) to capture an antigen. Such improvements result in an assay that has a lower cost to perform and which provides more consistent results over previous assays. For example, in embodiments utilising a peptide/antibody capture system or a steptavidin/biotin capture system, such systems may assist in reducing the washing of the solid substrate.

By way of illustration, ELISA can take up to 6 hours to complete and consist of at least 2 separate incubation and washing steps. Other enzyme-linked immunosorbent assays may generally take over 2 hours to complete and also requires at least 2 separate incubation and washing steps. The methods and/or kits of the present disclosure allow the assay to be performed in a shorter time and in some embodiments, allows a single incubation, one wash assay to be performed that is superior to previous ELISAs. For example, the reduction in handling steps allows a reduction in common sources of variation that are introduced by multiple handling steps, plate washing, and extra pipetting steps. Therefore, such previous assays require more handling, take more time and/or use more product resources and can result in greater costs.

In addition, as a result of the multiple incubation steps and sequential addition of components ELISA generally also require multiple wash steps to remove unbound components after each incubation step. For example, it is not uncommon in an ELISA for washing steps to be performed after binding of a capture antibody to a solid substrate, after addition of an analyte, and after addition of a detection antibody.

In some embodiments, the methods and/or kits of the present disclosure allow the number of washing steps to be reduced compared with previous assays. For example, in some embodiments the capture agent, the analyte and the detectable agent may be added to the solid substrate at the same time, or substantially the same time, intermediate washing steps may be avoided. The reduced number of washes may allow the methods to be performed in a simpler and more time-efficient manner. Furthermore, in some embodiments the reduced number of washes allows the methods and/or kits to be used for capture agents that may have a low binding affinity to the analyte, as the reduced amount of washing may reduce and/or eliminate dissociation between the capture agent and the analyte.

As described herein, the methods and/or kits of the present disclosure result in a number of advantages over traditional assays.

Some embodiments of the methods and/or kits of the present disclosure allow the time to detect an analyte to be reduced.

Some embodiments provide methods and/or kits for detecting an analyte, wherein the detection of the analyte is achieved in a time of less than 120 minutes. Some embodiments provide methods and/or kits for detecting an analyte, wherein the detection of the analyte is achieved in a time of less than 30, 40, 50, 60, 70, 80 or 90 minutes. In some embodiments, the detection of the analyte is achieved in a time range of 30 to 90 minutes, 30 to 80 minutes, 30 to 70 minutes, 30 to 60 minutes, 40 to 80 minutes, 40 to 70 minutes, 40 to 60 minutes, 50 to 80 minutes, 50 to 70 minutes, or 50 to 60 minutes. In some embodiments, the detection of the analyte is achieved in a time of at least 30, 40, 50, 60, 70, 80 or 90 minutes.

In some embodiments, the detection of the analyte is achieved in a time of less than 30 minutes. In some embodiments, the detection of the analyte is achieved in a time of less than 25, 15, 10 or 5 minutes. In some embodiments, the detection of the analyte is achieved in a time range of 5 to 30 minutes, 5 to 25 minutes, 5 to 20 minutes, 5 to 15 minutes, 10 to 30 minutes, 10 to 25 minutes, 10 to 15 minutes, 15 to 30 minutes, 15 to 25 minutes, 15 to 20 minutes, 20 to 30 minutes, or 20 to 25 minutes. In some embodiments, the detection of the analyte is achieved in a time of at least 5, 10, 15, 20, 25, or 30 minutes.

Some embodiments provide methods and/or kits for detecting an analyte, wherein the detection of the analyte is achieved in a time of less than 120 minutes from contacting the complex with the solid substrate.

Some embodiments provide methods and/or kits for detecting an analyte in a sample, wherein the detection of the analyte is achieved in a time of less than 30, 40, 50, 60, 70, 80 or 90 minutes from contacting the complex with the solid substrate. In some embodiments, the detection of the analyte is achieved in a time range of 30 to 90 minutes, 30 to 80 minutes, 30 to 70 minutes, 30 to 60 minutes, 40 to 80 minutes, 40 to 70 minutes, 40 to 60 minutes, 50 to 80 minutes, 50 to 70 minutes, or 50 to 60 minutes, from contacting the complex with the solid substrate. In some embodiments, the detection of the analyte is achieved in a time of at least 30, 40, 50, 60, 70, 80 or 90 minutes from contacting the complex with the solid substrate.

In some embodiments, the detection of the analyte is achieved in a time of less than 30 minutes from contacting the complex with the solid substrate. In some embodiments, the detection of the analyte is achieved in a time of less than 25, 15, 10 or 5 minutes contacting the complex with the solid substrate. In some embodiments, the detection of the analyte is achieved in a time range of 5 to 30 minutes, 5 to 25 minutes, 5 to 20 minutes, 5 to 15 minutes, 10 to 30 minutes, 10 to 25 minutes, 10 to 15 minutes, 15 to 30 minutes, 15 to 25 minutes, 15 to 20 minutes, 20 to 30 minutes, or 20 to 25 minutes from contacting the complex with the solid substrate. In some embodiments, the detection of the analyte is achieved in a time of at least 5, 10, 15, 20, 25, or 30 minutes from contacting the complex with the solid substrate.

Some embodiments provide methods and/or kits for detecting an analyte, wherein the detection of the analyte is achieved in a time of less than 120 minutes from contacting the sample, the capture agent, the detectable agent and the solid substrate.

Some embodiments provide methods and/or kits for detecting an analyte in a sample, wherein the detection of the analyte is achieved in a time of less than 30, 40, 50, 60, 70, 80 or 90 minutes from contacting the sample, the capture agent, the detectable agent and the solid substrate. In some embodiments, the detection of the analyte is achieved in a time range of 30 to 90 minutes, 30 to 80 minutes, 30 to 70 minutes, 30 to 60 minutes, 40 to 80 minutes, 40 to 70 minutes, 40 to 60 minutes, 50 to 80 minutes, 50 to 70 minutes, or 50 to 60 minutes, from contacting the sample, the capture agent, the detectable agent and the solid substrate. In some embodiments, the detection of the analyte is achieved in a time of at least 30, 40, 50, 60, 70, 80 or 90 minutes from contacting the sample, the capture agent, the detectable agent and the solid substrate.

In some embodiments, the detection of the analyte is achieved in a time of less than 30 minutes from contacting the sample, the capture agent, the detectable agent and the solid substrate. In some embodiments, the detection of the analyte is achieved in a time of less than 25, 15, 10 or 5 minutes from contacting the sample, the capture agent, the detectable agent and the solid substrate. In some embodiments, the detection of the analyte is achieved in a time range of 5 to 30 minutes, 5 to 25 minutes, 5 to 20 minutes, 5 to 15 minutes, 10 to 30 minutes, 10 to 25 minutes, 10 to 15 minutes, 15 to 30 minutes, 15 to 25 minutes, 15 to 20 minutes, 20 to 30 minutes, or 20 to 25 minutes from contacting the sample, the capture agent, the detectable agent and the solid substrate. In some embodiments, the detection of the analyte is achieved in a time of at least 5, 10, 15, 20, 25, or 30 minutes from contacting the sample, the capture agent, the detectable agent and the solid substrate.

As described, in some embodiments the reduced number of washes allows the methods and/or kits to be used for antibodies (capture antibodies and/or detectable antibodies) that may have a low or lower, binding affinity to the analyte, as the reduced amount of washing may reduce and/or substantially eliminate dissociation between the antibody and the analyte. In some embodiments, the methods and/or kits may be used with a capture agent having a Kd for binding with the analyte of greater than $10^{-6}$M. In further embodiments, the capture agent has a Kd for binding with the analyte of greater than $10^{-7}$M, $10^{-8}$M or $10^{-9}$M. In certain embodiments, the Kd is in the range from $10^{-8}$M to $10^{-12}$M.

Further, in previous assays that involve binding of a capture antibody to a solid substrate prior to exposure of the capture antibody to an analyte, the capture antibody is bound or adsorbed to a solid substrate in random orientations. As some of these orientations may mask part, or all, of the analyte binding domain of the capture agent, some of the capture agent bound to the solid substrate may not be available for analyte binding, thereby reducing the efficiency of the capture agent and the assay. Furthermore, in some orientations, although the capture agent may still be able to bind to the analyte, subsequent events such as binding of the detectable agent to the analyte, may be sterically hindered as a result of the orientation of the capture antibody on the solid substrate, thereby reducing the signal generated and hence the sensitivity and efficiency of the assay.

In contrast, in some embodiments the method of the present disclosure may promote the formation of a complex between a capture agent, an analyte and a detectable agent before or concurrent with contacting the complex with the solid substrate, which may prevent or inhibit binding of the capture agent to the solid substrate in an orientation which is not amenable to analyte binding. Thus, a greater proportion of the capture agent used may be available for analyte binding. Further, a lower concentration of capture agent (e.g. antibody) can be utilised without comprising sensitivity and/or specificity.

As described herein, some embodiments are directed to methods and/or kits for detecting an analyte in a sample with improved sensitivity and/or specificity. Some embodiments are directed to methods and/or kits wherein sensitivity is improved by the formation of a complex comprising the analyte, the capture agent and the detectable agent, before or concurrent with contacting the complex with the solid substrate.

As described herein, the methods and/or kits of the present disclosure allow for the detection of an analyte in a sample. In this regard, it will be understood that some embodiments of the present disclosure represent an immunoassay. Some embodiments of the present disclosure represent a sandwich assay, in which the analyte is bound to a capture antibody and to an antibody detectable agent.

As described herein, in some embodiments the methods and/or kits may comprise a qualitative determination of whether the analyte is present or absent in the sample.

As described herein, in some embodiments the methods and/or kits may comprise a quantitative assessment of the levels of the analyte in the sample. For example, in some embodiments the methods and/or kits allow for the quantification of the concentration of the analyte in the sample. Methods for the calculation of the concentration of an analyte are known.

In some embodiments, the method for detecting an analyte comprises an immunoassay. In some embodiments, the immunoassay comprises a non-competitive immunoassay. In some embodiments, the immunoassay comprises a competitive immunoassay. In some embodiments, the immunoassay comprises a combination of both a non-competitive and a competitive immunoassay.

In some embodiments, the analyte comprises one or more antigenic sites that allow the analyte to be bound by an antibody capture agent and/or an antibody detectable agent.

In some embodiments, the analyte comprises a non-nucleic acid analyte.

Some embodiments are based on the capture of the analyte by the capture agent via a mechanism that is not substantially based on nucleic acid-nucleic acid interactions, such as a binding based on complementary base pairing. That being said, it will be understood that in some embodiments, the analyte may comprise a nucleic acid component. In some embodiments the binding of the analyte by the capture agent is substantially based on hydrophobic, hydrophilic, polyanionic-polycationic, van der Waals, or combinations thereof, substantially exclusive of nucleic acid-nucleic acid interactions.

As described herein, examples of analytes that may be detected by the methods of the present disclosure comprise a microbe, a virus, a protein, a macromolecule, a small molecule, a drug or combinations thereof. Other types of analyte are contemplated.

In some embodiments, the analyte may comprise a component of a cell signalling pathway, a cytokine, a tumour suppressor, an antibody or a fragment thereof, or combinations thereof.

As described herein, in some embodiments the analyte may comprise a particular form or state of a molecule, such as a protein. For example, in some embodiments, the method may be used to detect a protein that is phosphorylated, methylated, glycosylated or combinations thereof. In these embodiments, at least one of the capture agent and the detectable agent may have specificity to only one form of the protein (for example the capture agent may only bind to the phosphorylated form of the protein and not to the unphosphorylated form of the protein).

As described herein, in some embodiments, the analyte may comprise a phosphoprotein. Examples of phosphoproteins comprise phosphorylated ERK, S6 p240/44, AKT pT308 or AKT pS473.

In some embodiments, the analyte is selected from the group consisting of phospho-ERK 1/2; total ERK 1/2; phospho-Akt 1/2/3; total Akt 1/2/3; phospho-NF-K$\beta$ p65; total NF-K$\beta$ p65; phospho-1-k$\beta\alpha$; total-k$\beta\alpha$; phospho-STAT3; total STAT3; phospho-STAT5 A/B; phospho-JNK 1/2/3; total JNK 1/2/3; phospho-p38 MAPK$\alpha$; total p38 MAPK$\alpha$; phospho-p53; total p53; phospho-p70S6K; total p70S6K; and GAPDH.

In some embodiments, the analyte is present in the sample at a concentration of 100 ng/ml or less, 10 ng/ml or less, 1 ng/ml or less, 100 pg/ml or less, or 10 pg/ml or less, 1 pg·ml or less, 100 fg/ml or less, 10 fg/ml or less, or 1 fg/ml or less. In some embodiments, the analyte is present in the sample at a concentration of greater than 100 ng/ml, greater than 10 ng/ml, greater than 1 ng/ml, greater than 100 pg/ml or, greater than 10 pg/ml, greater than 1 pg/ml, greater than 100 fg/ml, greater than 10 fg/ml or greater than 1 fg/ml. In some embodiments the analyte is present in the sample at a concentration of between 1 fg/ml to 100 ng/ml, 1 fg/ml to 10 ng/ml, 1 fg/ml to 1 ng/ml, 10 fg/ml to 100 ng/ml, 10 fg/ml to 10 ng/ml, 10 fg/ml to 1 ng/ml, 100 fg/ml to 100 ng/ml, 100 fg/ml to 10 ng/ml, 100 fg/ml to 1 ng/ml, 1 pg/ml to 100 ng/ml, 1 pg/ml to 10 ng/ml, or 1 pg/ml to 1 ng/ml.

As described herein, the present disclosure provides methods and/or kits for detecting an analyte in a sample. For example, the sample may be a mixture, composition, solution, that may or may not contain an analyte.

In some embodiments, the sample comprises one or more samples. In some embodiments, the sample comprises one or more samples comprising one or more analytes to be detected.

In some embodiments, the sample comprises a laboratory or research sample, a medical sample, a biological sample, a cell sample, a water sample, a food sample, an agricultural sample, and/or a derivative of these samples or combinations thereof.

In some embodiments, the sample comprises a medical sample or a cell sample, such as a blood sample, a serum sample, a urine sample, a milk sample, a cell lysate, a derivative of these samples and/or combinations thereof.

In some embodiments, the sample may be pre-treated before being used. For example, the sample may be pre-cleared, concentrated, diluted, induced, pre-treated or processed to remove one or more components or impurities from the sample using known methods.

In some embodiments, the sample may comprise a protein concentration of more than 0.01 mg/ml, a protein concentration of more than 0.1 mg/ml, a protein concentration of more than 1 mg/ml, a protein concentration of more than 2 mg/ml, a protein concentration of more than 10 mg/ml, or a protein concentration of more than 60 mg/ml. In some embodiments, the sample may comprise a protein concentration of less than 0.01 mg/ml, a protein concentration of less than 0.1 mg/ml, a protein concentration of less than 1 mg/ml, a protein concentration of less than 2 mg/ml, a protein concentration of less than 10 mg/ml, or a protein concentration of less than 60 mg/ml. These protein concentrations demonstrate that in some embodiments the methods and/or kits of the present disclosure are compatible for analyte detection in a range of biological milieu, such as cellular lysates, and/or serum.

In some embodiments, the methods and/or kits comprise one or more samples comprising one or more analytes to be detected. In some embodiments, a sample may comprise one or more analytes to be detected.

In some embodiments, the methods and/or kits comprises providing a reaction vessel.

Examples of reaction vessels include a test tube, a micro centrifuge tube, a well, or a flask. In some embodiments, the reaction vessel comprises a well of a multi-well plate, such as a microtitre plate, or a well or surface of a microfluidic device.

In some embodiments, the methods and/or kits comprise an assay platform. In some embodiments, the assay platform comprises one or more reaction vessels.

In some embodiments, the one or more reaction vessels comprise one or more solid substrates. The one or more solid substrates may comprise one or more bound immobilisation agents. In some embodiments, one or more reaction vessels comprise one or more bound immobilisation agents. In some embodiments, the assay platform comprises one or more reaction vessels comprising one or more solid substrates. In some embodiments, the assay platform comprises a multi-well plate, such as a microtitre plate. In some embodiments the one or more reaction vessels comprise one or more wells of a multi-well plate, such as a microtitre plate. In some embodiments, the assay platform comprises a plurality of reaction vessels comprising a solid substrate comprising the bound immobilisation agent. It will be appreciated that for an assay platform comprising a plurality of reaction vessels, some of the plurality of reaction vessels may comprise one or more reaction vessels comprising a bound immobilisation agent and one or more reaction vessels that do not comprise a bound immobilisation agent.

In some embodiments, the methods and/or kits comprise providing a single reaction vessel. In some embodiments, the use of a single reaction vessel for performing the steps in the method onward from the contacting of the sample, the antibody capture agent, the detectable agent and the solid substrate may reduce the handling steps involved in the method as compared to previous assays and thereby provide an improvement over such assays, including the ability to provide more consistent results over such assays.

In some embodiments, more than one analyte may be detected in one reaction vessel. In some embodiments, one analyte is detected in a sample. In some embodiments, one or more analytes are detected in a sample. In some embodiments, at least two analytes are detected in a sample.

In some embodiments the detection of more than one analyte may be achieved by providing several target-specific antibody capture agents to the reaction vessel, in combination with providing their respective detectable agents. For example, in some embodiments where each detectable agent is an antibody, each antibody may be conjugated to a different detectable tag, such as an enzyme, a fluorophore, a lanthanide, a chelate or combinations thereof.

In some embodiments, the methods and/or kits of the present disclosure provide one or more capture agents, the one or more capture agents being able to bind to one or more analytes to be detected and comprising, at a plurality sites, a ligand for the immobilisation agent.

In some embodiments, the use of a biotin-steptavidin/avidin capture system in conjunction with no additional washing of the solid substrate after contacting of the solid substrate with any one or more of the sample, the capture agent and the detectable agent may provide an advantage to the detection of more than one analyte.

As described herein, in some embodiments a reaction vessel comprises the solid substrate. In such embodiments, the solid substrate may be part of the reaction vessel. For example, the solid substrate may be integral with substantially all or part of the reaction vessel, and/or the solid substrate may form part of the surface of the reaction vessel (such as the surface of a well of a microtitre plate) or may be attached to the reaction vessel. Other combinations are also contemplated.

In some embodiments, the solid substrate is separate to the reaction vessel. In these embodiments, the solid substrate may be mobilisable and may be added to the reaction vessel.

For example, the solid substrate may be a bead, an affinity matrix, a resin, a gel, a slurry, a strip, or a dip stick. Combinations of different types of solid substrates are also contemplated.

In some embodiments, the bead is a magnetic bead. Methods for the use of magnetic beads are known in the art.

In some embodiments, the immobilisation agent is bound to the solid substrate by a covalent attachment to the solid substrate. For example, in some embodiments wherein the solid substrate is a bead, the immobilisation agent may be bound to the bead by a covalent attachment to the bead.

In some embodiments, the immobilisation agent is bound to the solid substrate via a non-covalent attachment. Examples of such interactions include a hydrophilic interaction, a hydrophobic interaction, a charged (ionic) interaction, a van de Waals interaction, or combinations of such interactions. In some embodiments, the immobilisation agent is passively bound to the solid substrate. In some embodiments, the immobilisation agent is actively bound to the solid substrate.

As described herein, the use of a bound immobilisation agent provides one or more advantages to some of the embodiments of the methods and/or kits for detecting an analyte. For example, the use of a bound immobilisation agent diminishes the potential influence of substrate-reactive proteins in the sample. For example, hydrophobic proteins in the sample are less likely to affect the outcome of the method and/or kits even if it is performed on a hydrophobic solid substrate, as the immobilisation agent is already bound to the solid substrate and the ligand on the capture agent may be specific for the immobilisation agent.

In some embodiments, the immobilisation agent and the ligand on the capture agent form a binding pair. A range of different immobilisation agent and ligand binding pairs may be used.

In some embodiments, the immobilisation agent and the ligand are a binding pair that is not a polyanionic-polycationic binding pair.

In some embodiments the use of an immobilisation agent-ligand binding pair which do not bind substantially through an ionic interaction between a substantially polyanionic molecule and a substantially polycationic molecule may provide one or more advantages to the method and/or kits for detecting an analyte in a sample. Examples of polyionic molecules include polymeric ionic substances, or polypeptides with repeated charged amino acids, such as a polyhistidine tag.

In some embodiments, advantages of using a immobilisation agent-ligand binding pair that is not a polyanionic-polycationic binding pair include, for example, the fact that the binding between the pair of molecules is less dependent upon the pH of any solution contacting the binding pair and/or the fact that the ability to reduce non-specific interactions is difficult with polyionic binding pairs. Furthermore, many proteins present in biological milieu may specifically bind either polyanions or polycations, making these components potentially difficult to detect with such an immobilisation system.

In addition, in some embodiments the use of a immobilisation agent-ligand binding pair that is not a polyanionic-polycationic binding pair may provide other advantages including promoting the formation of a complex between the capture agent, the analyte and the detectable agent, improving the access of such a complex to the solid substrate and promoting the ability of the detectable agent to access the analyte for detection purposes.

In some embodiments, the immobilisation agent and ligand binding pair comprise an anti-peptide tag antibody (for example the octapeptide DYKDDDDK (SEQ ID NO. 1) and an antibody against this peptide tag. Other examples of peptide tag/anti-peptide tag antibodies as binding pairs are disclosed herein.

In some embodiments, the immobilisation agent and ligand binding pairs comprise biotin and avidin or streptavidin (or derivates thereof); metal chelate (e.g. copper, nickel, cobalt) and Histidine (e.g. histidine tagged proteins); maleic anhydride and amine (e.g. amine containing proteins); or meleimide and sulfhydryls (e.g. sulfhydryl peptides).

As described herein, in some embodiments where a peptide tag is used as a ligand, the corresponding immobilization agent may comprise an anti peptide tag antibody, as described herein.

A range of anti peptide tag antibodies may be obtained or produced by a person skilled in the art. For example, commercially available antibodies against the peptide tag DYKDDDDK (SEQ ID NO. 1) are described herein. In some embodiments, the peptide tag comprises KRITVEEALAHPYLEQYYDPTDE (SEQ ID NO. 2), a sequence derived from the carboxy terminus of the human ERK proteins (ERK C-term peptide). In certain embodiments, the peptide tag does not comprise a plurality of consecutive amino acids with the same charge.

In some embodiments, the methods and/or kits of the present disclosure comprise an antibody capture agent and/or an antibody detectable agent.

As described herein, reference to an "antibody" is to be understood to mean an immunoglobulin molecule with the ability to bind an antigenic region of another molecule, and includes monoclonal antibodies, polyclonal antibodies, multivalent antibodies, chimeric antibodies, multispecific antibodies, diabodies and fragments of an immunoglobulin molecule or combinations thereof that have the ability to bind to the antigenic region of another molecule with the desired affinity including a Fab, Fab', F(ab')$_2$, Fv, a single-chain antibody (scFv) or a polypeptide that contains at least a portion of an immunoglobulin that is sufficient to confer specific antigen binding, such as a molecule including one or more CDRs. Antibodies and/or binding fragments thereof to specific analytes may be obtained commercially or generated by known methods.

As described herein, in some embodiments the methods and/or kits of present disclosure comprise providing the capture agent in solution.

In many previous methods for detecting an analyte using a capture agent, the capture agent is immobilised on the solid substrate prior to coming into contact with the analyte and binding to the analyte. In some embodiments, the use of a capture agent in solution provides one or more advantages over the use of a capture agent immobilised on the solid substrate. Without being bound by theory, it is believed that the use of the capture agent in solution in some of the embodiments promotes the binding of the capture agent to the analyte and thereby promotes the formation of a complex of the capture agent, the analyte and the detectable agent.

In this regard, it will be understood that in some embodiments the capture agent is provided in solution prior to contacting the capture agent with the sample. Accordingly, in some embodiments the capture agent is provided in a form where it is not immobilised to a solid substrate and is provided in a substantially liquid state.

In some embodiments, the use of an antibody capture agent in solution also reduces the amount of a specific antibody to a target to be reduced as compared to previous immunoassays, as more target-specific capture antibody is required in assays when the absorbed capture is pre-absorbed onto a plate. In some embodiments there is no pre-immobilisation of the capture agent on the solid substrate.

In some embodiments, the capture agent comprises a plurality of ligands for the immobilisation agent. In some embodiments, the capture agent comprises, at a plurality of sites, a ligand for the immobilisation agent. In some embodiments, the capture agent comprises different ligands. Immobilisation agent-ligand binding pairs are as described herein.

In some embodiments, the ligand may be part of the capture agent. For example, the capture agent may comprise poly-histidine residues, amine groups or sulfhydryl groups that are able to bind to the immobilisation agent.

In some embodiments, the ligand is bound to the capture agent.

In some embodiments, the ligand for the immobilisation agent comprises a peptide tag, such as the octapeptide DYKDDDDK (SEQ ID NO. 1), sometimes referred to as FLAG-tag.

As described herein, peptide-tags are polypeptide tags that can be conjugated to an another agent, such as a protein or an antibody, or added to a protein using recombinant DNA technology. As describe herein, one example of a peptide tag is the peptide DYKDDDDK (SEQ ID NO. 1), which can be used in different assays that utilize recognition by an antibody. Other examples of peptide tags are described herein.

Adding a peptide tag to a protein allows the protein to be bound and/or immobilised by an antibody against the peptide tag sequence. In some embodiments, a peptide tag may also be used in conjunction with other affinity tags for example a polyhistidine tag (His-tag), HA-tag or myc-tag.

The addition of a peptide tag to the capture agent to form a conjugate may be achieved by a suitable known method.

As described herein, in some embodiments the methods and/or kits for detecting an analyte comprise providing a detectable agent which can bind to the analyte.

In some embodiments the detectable agent is provided in solution. Accordingly, in some embodiments the detectable agent is provided in a substantially liquid state.

In some embodiments, the use of a detectable agent in solution may provide one or more advantages to the methods and/or kits of the present disclosure, including promoting the formation and detection of a complex of the capture agent, the analyte and the detectable agent.

In some embodiments, the methods and/or kits of the present disclosure provide one or more detectable agents, the one or more detectable agents being able to bind to one or more analytes to be detected.

In some embodiments, the detectable agent comprises an antibody (including a binding fragment thereof), an aptamer, or a protein receptor or ligand (or binding fragment thereof) as described herein. Examples of antibodies and binding fragments thereof are as described herein.

Protein receptors or ligands used as a detectable agent may comprise the whole receptor or ligand or a fragment thereof (for example a fragment comprising a binding domain of the receptor or ligand). In some embodiments, the receptor or ligand (or fragment thereof) may comprise a fusion protein. Fusion partners may include, for example, fluorescent fusion partners (e.g. GFP) and immunoglobulin fusion partners. Fusion partners and methods for preparing fusion proteins are known in the art. In some embodiments, the fusion partner may act to stabilise the receptor or ligand (or fragment thereof), provide a detectable signal (e.g. for fluorescent fusion partners) or provide a target for antibody, or other, binding or immobilisation.

Aptamers used as a detectable agent may be obtained commercially or generated by known methods.

In some embodiments, the detectable agent may comprise a detectable tag. In some embodiments, the detectable tag may be applied to the detectable agent (for example bound to the detectable agent) or may be part of the detectable agent (for example the detectable agent may include the detectable tag as a fusion partner, a labelled amino acid or labelled nucleotide).

Examples of suitable detectable tags include antigens, enzymes, fluorophores, quenchers, radioactive isotopes and luminescent labels. It will be appreciated that the detectable tag may be detected directly or indirectly via a further molecule that can produce a detectable signal.

Antigens that may be used as a detectable tag may include, for example, any antigenic component of the detectable agent that may be targeted by a secondary detectable agent. For example, in some embodiments, a secondary antibody may be used to detect an antigen on a detectable agent. The secondary antibody may be fluorescently or enzymatically labelled. In embodiments where the detectable agent is a primary antibody (ie. an analyte binding antibody), the secondary antibody may have binding affinity to an antigen on the primary antibody. For example, the antigen may be derived from the host in which the detectable agent was raised.

In some embodiments, the detectable tag comprises an enzyme. Enzymes that may be used as detectable tags include, for example, enzymes that result in the conversion of a substrate into a detectable product (generally resulting in a change in colour or fluorescence or generation of an electrochemical signal). Such enzymes may include, for example, horseradish peroxidase (HRP), alkaline phosphatase (AP), β-galactosidase, acetylcholinesterase, luciferase, catalase or combinations thereof. Depending on the enzyme and substrate used, detection may be performed with a spectrophotometer, fluorometer, luminometer, electrochemical detection means. Other detection means are contemplated.

Radioactive isotopes that may be used as detectable tags include, for example, $^{3}H$, $^{14}C$, $^{32}P$, $^{35}S$, or $^{131}I$. Other isotopes are contemplated. The radioisotope may be conjugated to a detectable agent or incorporated into a detectable agent by translation of mRNA encoding the detectable agent in the presence of radiolabelled amino acids. Radioisotopes and methods for conjugating radioactive isotopes to molecules such as proteins are known in the art. Radioisotopes may be detected using gamma, beta or scintillation counters.

Fluorophores that may be used as detectable tags include, for example, resorufin, fluorescein (fluorescein isothiocyanate, FITC), rhodamine (tetramethyl rhodamine isothiocyanate, TRITC), green fluorescent protein (GFP), phycobiliproteins (allophycocyanin, phycocyanin, phycoerythrin and phycoerythrocyanin, derivatives of any of the foregoing) or combinations thereof. In some embodiments, the detectable tag may be part of the detectable agent (e.g. in the form of a fusion protein or a protein comprising fluorescent amino acids). Fluorophores may be subjected to applied stimulation (for example light of a suitable excitation wavelength) to promote fluorescence.

Luminescent compounds that may be used as detectable tags include, for example, chemiluminescent and/or bioluminescent compounds. These compounds may be used to label the detectable agent. The presence of the chemiluminescent-tag may be determined by detecting the presence of luminescence that arises during the course of a chemical reaction. Examples of useful chemiluminescent labelling compounds are luminol, isoluminol, theromatic acridinium ester, imidazole, acridinium salt and oxalate ester or combinations thereof. Bioluminescence is a type of chemiluminescence found in biological systems in which a catalytic protein increases the efficiency of the chemiluminescent reaction. The presence of a bioluminescent antibody is determined by detecting the presence of luminescence. Examples of bioluminescent compounds include luciferin, luciferase and aequorin.

In some embodiments, the methods and/or kits for detecting an analyte comprise contacting the sample, the capture agent, the detectable agent and the solid substrate, in a reaction vessel, to form a mixture. In some embodiments, the components are brought into contact with each other, in the reaction vessel, to allow the formation of a complex between the capture agent, the analyte and the detectable agent, the complex being able to be immobilised on the solid substrate (via the ligand on the solid substrate) concurrently or after its formation. As described herein, this may provide advantages to the performance of certain methods and/or kits of the present disclosure.

As described herein, in some embodiments the methods and/or kits of the present disclosure comprise contacting the sample, the capture agent, the detectable agent and the solid to allow binding of the capture agent and the detectable agent to the analyte to form a complex. Upon formation, the complex may be immobilized on the solid substrate via the ligand binding to the immobilisation agent bound to the solid substrate.

As described herein, in some embodiments, the methods and/or kits provide contacting in one or more of at least two reaction vessels, one or more samples, one or more capture agents and one or more detectable agents to allow the formation of one or more complexes comprising an analyte, a capture agent and a detectable agent.

In some embodiments, the methods and/or kits provide contacting one or more complexes with the solid substrate, such that the immobilisation agent may bind the one or more complexes via the ligand.

In some embodiments, prior to bringing the components into contact with each other in the reaction vessel, specific individual components may be brought into contact prior with each other.

In some embodiments, contacting of one or more of the individual components may occur in the reaction vessel or may occur in one or more separate reaction vessels.

In some embodiments, the sample, the capture agent, the detectable agent and the solid substrate are not contacted in a separate vessel prior to contacting in the reaction vessel. Thus, the combination of the components is contacted together for the first time in the reaction vessel.

In some embodiments, the sample and the solid substrate are contacted prior to contacting with the capture agent and/or the detectable agent. As discussed herein, this particular method of contacting provides one or more advantages to the performance of some embodiments of the methods and/or kits, as the capture agent and/or the detectable agent are exposed to the analyte in the presence of the solid substrate.

In some embodiments, the sample (and analyte(s) therein) is exposed to the solid substrate prior to exposure to either or both of the capture agent and the detectable agent. As discussed herein, in some embodiments this particular method of contacting provides an advantage to the performance of the method, as the capture agent and/or the detectable agent do not come into contact with the analyte until the analyte is in the presence of the solid substrate. For example, without being bound by theory, this may provide advantages to the formation of the complex between the capture agent, the analyte and the detectable agent.

In some embodiments, the sample and the solid substrate are contacted in the reaction vessel.

In some embodiments where the solid substrate forms part of the reaction vessel, the sample may be added to the reaction vessel and subsequently the capture agent and/or the detectable agent are brought into contact with the sample and the solid substrate.

In some embodiments, the sample and the solid substrate are not substantially incubated prior to contacting with the capture agent and/or the detectable agent. In some embodiments, this may provide an advantage by reducing the time required to detect the analyte.

In some embodiments, the capture agent and the detectable agent are brought into contact with each other before they are contacted with either or both of the sample and the solid substrate. Typically, this may be achieved by first contacting the capture antibody and the detectable agent in a separate vessel.

In some embodiments wherein the solid substrate forms part of the reaction vessel, the capture agent and the detectable agent are brought into contact with each other and then placed in the reaction vessel containing a sample.

In some embodiments, the capture agent and the detectable agent are sequentially contacted with the previously contacted sample and/or the solid substrate.

In some embodiments, the sample and the solid substrate are brought into contact and then each of the capture agent and the detectable agent are then brought into contact with the sample and the solid substrate. In some embodiments, the capture agent is first contacted with the sample and the solid substrate and subsequently the detectable agent is brought into contact with the capture agent, the sample and the solid substrate. In some embodiments, the detectable agent is first contacted with the sample and the solid substrate and subsequently the capture agent is brought into contact with the detectable agent, the sample and the solid substrate.

As described herein, in some embodiments the complex comprising the analyte, capture agent and detectable agent is formed prior to binding between the immobilisation agent and the ligand. The complex may be formed by sequential or concurrent addition of the capture agent and detectable agent to the analyte prior to contacting the complex with the immobilisation agent on the solid substrate.

In some embodiments, there is an incubation of the contacted sample, the solid substrate, the capture agent and the detectable agent.

In some embodiments, there is an incubation of the complex and the solid substrate.

In some embodiments, there is an incubation of the contacted sample, the solid substrate, the capture agent and the detectable agent prior to washing of the solid substrate.

In some embodiments, there is an incubation of the complex and the solid substrate prior to washing of the solid substrate.

In some embodiments, the incubating is 2 hours or less, 90 minutes or less, 80 minutes or less, 70 minutes or less, 1 hour or less, 50 minutes or less, 40 minutes or less, 30 minutes or less, 20 minutes or less, 15 minutes or less, 10 minutes or less, or 5 minutes or less. In some embodiments, if desired, there will be no incubation.

In some embodiments, the incubation is between 10 minutes to 2 hours, 10 minutes to 1 hour, 15 minutes to 2 hours, 15 minutes to 1 hour, 30 minutes to 2 hours, 30 minutes to 1 hour, or 1 hour to 2 hours. In some embodiments, the incubation is at least 5, 10, 15, 20, 25, 30, 60, 70, 80, 90 or 120 minutes.

In some embodiments, the incubating is 30 minutes or less. In some embodiments, the incubating is 25 minutes or less, 15 minutes or less, 10 minutes or less or 5 minutes or less. In some embodiments, the incubating is 5 to 30 minutes, 5 to 25 minutes, 5 to 20 minutes, 5 to 15 minutes, 10 to 30 minutes, 10 to 25 minutes, 10 to 15 minutes, 15 to 30 minutes, 15 to 25 minutes, 15 to 20 minutes, 20 to 30 minutes, or 20 to 25 minutes. In some embodiments, the incubating is at least 5, 10, 15, 20, 25, or 30 minutes.

In some embodiments, the incubation of the contacted sample, the solid substrate, the capture agent and the detectable agent prior to washing of the solid substrate occurs in the same reaction vessel. In some embodiments the incubation of the contacted sample, the solid substrate, the capture agent and the detectable agent prior to washing of the solid substrate occurs in a separate reaction vessel.

In some embodiments, the incubation of the complex and the solid substrate prior to washing of the solid substrate occurs in the same reaction vessel. In some embodiments the incubation of the complex and the solid substrate prior to washing of the solid substrate occurs in a separate reaction vessel.

As described herein, in some embodiments the methods and/or kits comprise washing the solid substrate one or more times to remove both the capture agent and the detectable agent not bound to the solid substrate via the ligand. The washing of the solid substrate may be performed using a suitable method, sufficient to remove capture agent and detectable agent not bound to the solid substrate via the ligand on the capture agent.

Washing the solid substrate prior to detection of the detectable agent allows the removal of unbound detectable agent and/or detectable agent not bound via the capture agent, which can decrease the level of background signal and hence improve sensitivity. Methods for washing steps are known and generally involve repeated addition and removal of buffer.

The solid substrate may be washed one or more times, and with one or more buffers. In some embodiments, the solid substrate may be washed two or more times, and with one or more buffers. In some embodiments, the solid substrate may be washed three or more times, and with one or more buffers.

In some embodiments, there is no additional washing of the solid substrate after contacting of the solid substrate with any one or more of the sample, the capture agent and the detectable agent.

For example, in embodiments utilising a peptide/antibody capture system or a steptavidin/biotin capture system, such systems may assist in reducing the steps involving washing of the solid substrate.

In these embodiments it will be appreciated that there may be no additional washing of the solid substrate after contacting of the solid substrate with any one or more of the sample, the capture agent and the detectable agent. However, in some embodiments, if desired, additional washing of the solid substrate after contacting of the solid substrate with any one or more of the sample, the capture agent and the detectable agent may be conducted. In some embodiments, one, two, three or four washings of the solid substrate after contacting of the solid substrate with any one or more of the sample, the capture agent and the detectable agent may be conducted.

In some embodiments, the methods and/or kits may be performed using only a single/one wash step conducted during the entire method. In some embodiments, the use of a one wash protocol may provide one or more advantages. For example, not only does the use of a one wash protocol provide advantages to the number of handling steps involved and the time required to conduct the method, the one wash protocol may also provide an improvement in the efficiency and performance of the method. It will be appreciated that in a one wash protocol, the solid substrate may be washed one or more times at that step in the protocol.

However, in certain embodiments, the one wash protocol may be varied, if desired, to add additional washes or rinses at various stages of the protocol or to add additional washes or rinses at various stages of the protocol.

In some embodiments, there is no additional washing of the solid substrate after contacting of the solid substrate with any one or more of the sample, the capture agent and the detectable agent.

As described previously herein, in some embodiments the methods and/or kits of the present disclosure comprise detecting the analyte by detecting the presence of the detectable agent bound to the solid substrate.

In this regard, in some embodiments the detection of the analyte is achieved by detecting the presence of the detectable agent present in the complex immobilised to the solid substrate in the reaction vessel.

In some embodiments the methods and/or kits of the present disclosure comprise detecting the analyte by detecting the presence of the detectable agent present in the complex immobilised to the solid substrate in the reaction vessel.

In some embodiments, the methods and/or comprise detecting the presence of one or more immobilised complexes on the solid substrate by detection of the one or more detectable agents.

The detection of an analyte by detecting the presence of the detectable agent bound to the substrate may be achieved by a suitable method specific to the detectable agent. Examples of detectable agents are as described herein.

As described herein, the time taken to perform a method for detecting an analyte in a sample is an important consideration.

For example, ELISA can be time-intensive and it is not uncommon in ELISA for incubation steps to be performed after the addition of each individual component of the ELISA.

As discussed herein, in some embodiments the present disclosure minimises the number of incubation, handling and/or washing steps. In some embodiments, this makes the method of the present disclosure particularly amenable to automation. Previous assays are difficult to automate as multiple handling steps are needed, including several aspiration, dispensing, and washing steps.

In some embodiments, reducing the number of incubation steps and/or washing steps that are required may allow the duration of the complex to solid substrate binding step to be maximised without increasing the total duration of the method. In some embodiments, increasing the duration of the complex to solid substrate binding step may increase the sensitivity of the method. Some embodiments of the present disclosure contemplate, if desired, various combinations as to the number of incubation, handling and/or washing steps.

In some embodiments, the detection of the analyte is achieved in a time of 2 hours or less from contacting the sample with the capture agent and/or the detectable agent.

In some embodiments, the detection of the analyte is achieved in a time of 90 minutes or less, 70 minutes or less, 60 minutes or less, 50 minutes or less, 45 minutes or less, 40 minutes or less, 30 minutes or less, 20 minutes or less, 15 minutes or less, or 10 minutes or less from contacting the sample with the capture agent and/or the detectable agent. In some embodiments, the detection of the analyte is achieved in a time period of between 10 minutes to 120 minutes, 10 minutes to 90 minutes, 10 minutes to 60 minutes, 15 minutes to 120 minutes, 15 minutes to 90 minutes, 15 minutes to 60 minutes, 15 minutes to 30 minutes, 30 minutes to 120 minutes, 30 minutes to 90 minutes, 30 minutes to 60 minutes, 45 minutes to 120 minutes, 45 to 90 minutes, or 45 minutes to 60 minutes from contacting the sample with the capture agent and/or the detectable agent.

In some embodiments, the detection of the analyte is achieved in a time of less than 60 minutes from contacting the sample with the capture agent and/or the detectable agent. In some embodiments, the detection of the analyte is achieved in a time of less than 30 minutes from contacting the sample with the capture agent and/or the detectable agent. In some embodiments, the detection of the analyte is achieved in a time of less than 15 minutes from contacting the sample with the capture agent and/or the detectable agent. In some embodiments, the detection of the analyte is achieved in a time of less than 10 minutes from contacting the sample with the capture agent and/or the detectable agent.

As described herein, in some embodiments the use of a capture system may assist in reducing the time required to undertake an assay. For example, in embodiments utilising a peptide/antibody capture system or a steptavidin/biotin capture system, such systems may assist in reducing the time to undertake such an assay.

As described herein, in some embodiments the use of a capture system may assist in reducing the washing of the solid substrate and/or reducing the time required to undertake an assay. For example, in embodiments utilising a peptide/antibody capture system or a steptavidin/biotin capture system, such systems may assist in reducing the washing of the solid substrate and in reducing the time to undertake such an assay.

As described herein, as some embodiments of the methods also allow detectable signals to be produced with less capture agent and/or reduced solid substrate surface area relative to ELISA, some methods may be suitable for microfluidic systems, where miniaturisation of structures and minimisation of reagents used is desirable. Accordingly, in some embodiments, the method may be performed in a microfluidic system, as described herein.

In some embodiments, the methods and/or kits show a low variability for detecting an analyte between reactions. In some embodiments, the methods and/or kits show a low intra-plate variability. In certain embodiments, the variability is 30% or less, 20% or less, or 10% or less. For example, in certain embodiments the methods and/or kits shows a low intra-plate variability for detecting an analyte, such as an intra-plate variability of 30% or less, 20% or less, or 10% or less.

In some embodiments, the methods and/or kits of the present disclosure may also be performed by utilising reagents and/or instructions.

In some embodiments, a further advantage of some embodiments of the methods and/or kits of the present disclosure is the ability to use a single assay plate or platform that is suitable for many different assay kits. This may provide manufacturers with a number of benefits, including reduced cost, labor and quality control requirements, in comparison to preparing a different assay plate for every assay kit, as is the current standard for ELISA kit manufacture. In addition, in some embodiments inputs can be reduced by the ability to use less of the target-specific capture antibody, again reducing costs and quality control requirements, as single batches of target-specific antibodies can be used for more assay kits.

In some embodiments, the present disclosure provides a method for detecting one or more analytes in one or more samples using a single assay platform, the method comprising:
  providing one or more samples comprising one or more analytes to be detected;
  providing a single assay platform comprising at least two reaction vessels, the at least two reaction vessels comprising a solid substrate comprising a bound immobilisation agent;
  providing one or more capture agents, the one or more capture agents being able to bind to the one or more analytes to be detected and comprising, at a plurality sites, a ligand for the immobilisation agent;
  providing one or more detectable agents, the one or more detectable agents being able to bind to the one or more analytes to be detected;
  contacting in one or more of the at least two reaction vessels in the assay platform, the one or more samples, the one or more capture agents and the one or more detectable agents to allow the formation of one or more complexes comprising an analyte, a capture agent and a detectable agent;
  contacting the one or more complexes with the solid substrate such that the immobilisation agent may bind the one or more complexes via the ligand; and
  detecting the presence of one or more immobilised complexes on the solid substrate by detection of the one or more detectable agents.

In some embodiments, the bound immobilisation agent is the same immobilisation agent.

In some embodiments, the present disclosure provides a method for detecting one or more analytes in one or more samples using a single assay platform, the method comprising:
  providing one or more samples comprising one or more analytes to be detected;
  providing a single assay platform comprising at least two reaction vessels, the at least two reaction vessels comprising a solid substrate comprising the same bound immobilisation agent;
  providing one or more capture agents, the one or more capture agents being able to bind to the one or more analytes to be detected and comprising, at a plurality sites, a ligand for the immobilisation agent;
  providing one or more detectable agents, the one or more detectable agents being able to bind to the one or more analytes to be detected;
  contacting in one or more of the at least two reaction vessels in the assay platform, the one or more samples, the one or more capture agents and the one or more detectable agents to allow the formation of one or more complexes comprising an analyte, a capture agent and a detectable agent;

contacting the one or more complexes with the solid substrate such that the immobilisation agent may bind the one or more complexes via the ligand; and detecting the presence of one or more immobilised complexes on the solid substrate by detection of the one or more detectable agents.

In some embodiments, a kit is utilised for performing the methods of the present disclosure. The kit may comprise one or more of the reagents and/or one or more components herein described and/or instructions to assist in the performance of the method.

In some embodiments, the present disclosure provides a kit for detecting an analyte in a sample, the kit comprising:

an assay platform comprising a plurality of reaction vessels, one or more of the reaction vessels comprising a bound immobilisation agent;

a capture agent which can bind to an analyte, wherein the capture agent comprises, at a plurality of sites, a ligand for the immobilisation agent;

an antibody detectable agent which can bind to the analyte, wherein the antibody detectable agent comprises a detectable tag; and instructions for detecting the analyte.

In some embodiments, the kit comprises instructions for detecting the analyte in a time of 2 hours or less, 90 minutes or less, 80 minutes or less, 70 minutes or less, 1 hour or less, 45 minutes or less, 30 minutes or less, 15 minutes or less, or 10 minutes or less.

In some embodiments, the kit comprises instructions for detecting the analyte comprise instructions for detecting the analyte in a time of 2 hours or less, 90 minutes or less, 80 minutes or less, 70 minutes or less, 1 hour or less, 45 minutes or less, 30 minutes or less, 15 minutes or less, or 10 minutes or less from contacting the sample with the capture agent and/or the detectable agent.

In some embodiments, the kit comprises instructions for the detecting of the analyte in a time period of between 10 minutes to 120 minutes, 10 minutes to 90 minutes, 10 minutes to 60 minutes, 10 minutes to 30 minutes, 15 minutes to 120 minutes, 15 minutes to 90 minutes, 15 minutes to 60 minutes, 30 minutes to 120 minutes, 30 minutes to 90 minutes, 30 minutes to 60 minutes, 45 minutes to 120 minutes, 45 to 90 minutes, 45 minutes to 75 minutes, or 45 minutes to 60 minutes.

In some embodiments, the kit comprises instructions for the detecting of the analyte in a time period of between 10 minutes to 120 minutes, 10 minutes to 90 minutes, 10 minutes to 60 minutes, 10 minutes to 30 minutes, 15 minutes to 120 minutes, 15 minutes to 90 minutes, 15 minutes to 60 minutes, 30 minutes to 120 minutes, 30 minutes to 90 minutes, 30 minutes to 60 minutes, 45 minutes to 120 minutes, 45 to 90 minutes, 45 minutes to 75 minutes, or 45 minutes to 60 minutes from contacting the sample with the capture agent and/or the detectable agent.

In some embodiments, the immobilisation agent is avidin, streptavidin and/or a derivative thereof and the ligand is biotin and/or a derivative thereof.

In some embodiments, the immobilisation agent is an anti peptide tag antibody and the ligand is a peptide tag. Other immobilisation agent and ligand binding pairs are as described herein.

In some embodiments, the capture agent comprises an antibody or a fragment thereof. In some embodiments, the capture agent comprises an antibody capture agent. In some embodiments, capture agent is in solution. In some embodiments, the antibody capture agent is in solution. Capture agents are as described herein.

In some embodiments, the detectable agent comprises an antibody or a fragment thereof. In some embodiments, the detectable agent comprises an antibody detectable agent. In some embodiments, the detectable agent is in solution. In some embodiments, the antibody detectable agent is in solution. Detectable agents are as described herein.

As described herein, in some embodiments, a further advantage of some embodiments of the methods and/or kits of the present disclosure is the ability to use a single assay plate or platform that is suitable for many different assay kits. In some embodiments, this may provide manufacturers with a number of benefits, including reduced cost, labor and quality control requirements, in comparison to preparing a different assay plate for every assay kit, as is the current standard for ELISA kit manufacture. In addition, in some embodiments inputs can be reduced by the ability to use less of a target-specific capture antibody, again reducing costs and quality control requirements, as single batches of target-specific antibodies can be used for more assay kits.

In some embodiments, the kit comprises an assay platform. In some embodiments, the assay platform comprises a plurality of reaction vessels. In some embodiments, one or more of the reaction vessels comprises a bound immobilisation agent. In some embodiments, one or more of the reaction vessels comprise a solid substrate. In some embodiments, the assay platform comprises a multi-well plate, such as a microtitre plate, and the one or more reaction vessels comprise a well of the multi-well plate.

In some embodiments, the instructions comprise instructions for utilising only a single wash of the solid substrate after contacting of the solid substrate with any one or more of the sample, the capture agent and the detectable agent.

The present disclosure is further described by the following examples. It is to be understood that the following description is for the purpose of describing particular embodiments only and is not intended to be limiting with respect to the above description.

BRIEF DESCRIPTION OF THE FIGURES

FIG. 1 shows for the purposes of comparison, three ELISA protocols for the detection of phosphorylated ERK 1/2 (pERK) were examined, using various concentrations of a cellular lysate containing pERK. (1) A simultaneous ELISA format, whereby the assay components, namely the capture antibody (anti-pERK-biotin), the analyte (cellular lysate), and the detection antibody (anti-ERK-HRP), were incubated concurrently in a streptavidin-coated microplate. (2) A standard multi-incubation ELISA format, whereby the capture antibody was first incubated in a streptavidin-coated microplate, followed by the analyte, and finally the detection antibody. (3) A standard multi-incubation ELISA format, whereby the analyte was incubated in a capture-antibody coated microplate, followed by a detection antibody. The assays were incubated for either 30 min (FIG. 1A) for each incubation step or 60 min (FIG. 1B) for each incubation step, and the wells were subjected to a standard wash cycle between each incubation step for each assay. After the final incubation and wash, QuantaRed™ HRP substrate was added to the wells, and each plate was incubated for 10 min in the dark. The fluorescent signal in the wells was measured at 550ex/600em nm.

FIG. 2 shows for the purposes of comparison, three ELISA protocols for the detection of phosphorylated ERK 1/2 (pERK), using various concentrations of a cellular lysate containing pERK. (1) A simultaneous ELISA format, whereby the assay components, namely the capture antibody (anti-pERK-biotin), the analyte (cellular lysate), and the detection antibody (anti-ERK-HRP), were incubated concurrently in a streptavidin-coated microplate for either 30 min (FIG. 2A) or 60 min (FIG. 2B). (2) A standard multi-incubation ELISA format, whereby the capture antibody was first incubated in a streptavidin-coated microplate for 10 min, followed by the analyte for 10 min, and finally the detection antibody for 10 min, giving a total cumulative assay incubation time of 30 min (FIG. 2A). (3) A standard multi-incubation ELISA format, whereby the analyte was incubated in a capture-antibody coated microplate for 30 min, followed by the detection antibody for 30 min, giving a total cumulative assay time of 60 min (FIG. 1B). The wells were subjected to a standard wash cycle between each incubation step for each assay. After the final incubation and wash, QuantaRed™ HRP substrate was added to the wells, and each plate was incubated for 10 min in the dark. The fluorescent signal in the wells was measured at 550ex/600em nm.

FIG. 3 shows the mean and standard deviations for the duplicate data points for each target analyzed. In this Figure, the comparison clearly demonstrates that optimal assay performance is achieved with lower capture antibody concentrations when the assay components are incubated concurrently for both biotin-capture and peptide-capture protocols, when compared with standard ELISA protocols whereby analytes are incubated sequentially, and washed between incubations. This data demonstrates that the assay has the potential to lower input costs for ELISA plate manufacture.

FIG. 4 shows the mean and standard deviations for the duplicate data points for each target analyzed. In this Figure, the comparison clearly demonstrates that no benefit to assay performance is achieved with the inclusion of a pre-incubation step prior to introduction to a solid substrate carrying the immobilization agent.

FIG. 5 shows the mean and standard deviations for the duplicate data points at each pERK lysate concentration analyzed. In this Figure, the assay clearly demonstrates the utility whereby the assay components are incubated concurrently.

FIG. 6 shows the mean and standard deviations for the duplicate data points for each target analyzed. In this Figure, the assay clearly demonstrates efficacy for several different targets, whereby the assay components are incubated concurrently.

FIG. 8 demonstrates the results of electrochemical detection of pERK in a microfluidic system.

FIG. 9 shows the results of electrochemical detection of pAKT473 in a microfluidic system.

FIG. 10 shows the mean and standard deviations for the duplicate data points for each target analyzed. In FIG. 10, the assays clearly demonstrate that when added within the short time period described, the order of addition of individual assay components does not affect assay performance, compared with assay components that are added simultaneously.

FIG. 11 shows the mean and standard deviations for the duplicate data points for each target analyzed. In this Figure, the assay clearly demonstrates efficacy for several different targets in serum, whereby the assay components are incubated concurrently. The high signal for EGF in human serum is due to the presence of endogenous EGF protein(s) in this medium.

FIG. 12 shows the mean and standard deviations for the duplicate data points for each target analyzed. In this Figure, the assay clearly demonstrates efficient detection within 15 min total assay time for several different targets, using certain embodiments, whereby the assay components are incubated concurrently.

FIG. 15 shows detection of either phospho-AKT (pSer473) or phospho-ERK in a 25 min total assay time. For each target, recombinant active (FIG. 15A) phospho-AKT or phospho-ERK (FIG. 15B) was diluted as indicated, to various concentrations using 1× Lysis buffer containing 0.1% BSA and added to 4 replicate wells of a 96-well streptavidin-coated microplate. To initiate the assay reaction, for either target, a mixture of the biotin-conjugated capture antibody, and the HRP-conjugated detection antibody were added to the lysates, and incubated for 1 hour. The wells were subjected to a standard wash cycle for each assay. After the wash cycle, QuantaRed™ HRP substrate was added to the wells, and each plate was incubated for 10 min in the dark. The fluorescent signal in the wells was measured at 550ex/600em nm.

Example 1

Materials

Figure 1A:
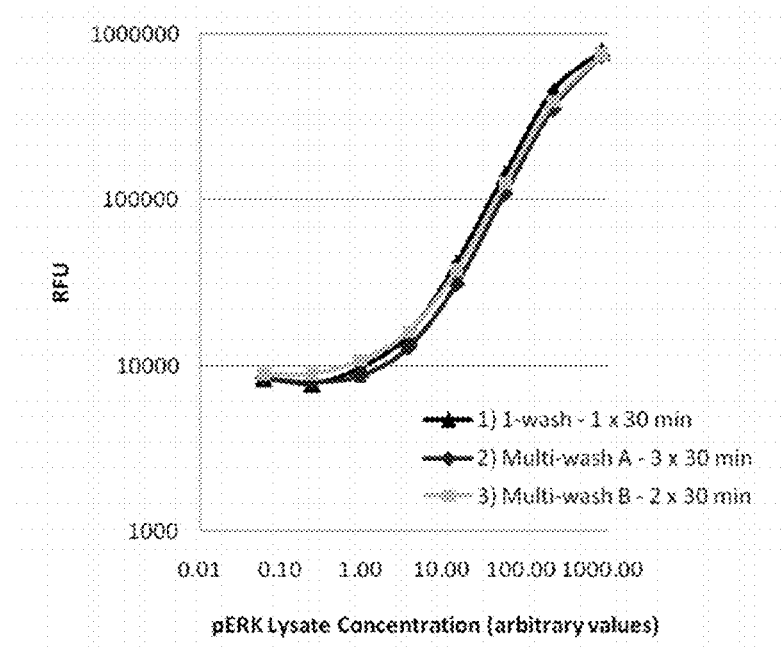
FIGS. 1A and 1B show the mean and standard deviations for the duplicate data points at each pERK lysate concentration analyzed. In this Figure the comparison clearly demonstrate comparable assay performance over a shorter time period when the assay components are incubated concurrently, compared with standard ELISA protocols whereby assay components are incubated sequentially.

Antibodies used in the following examples include: anti-pERK mouse monoclonal (+/−biotinylation); anti-total ERK rabbit monoclonal (+/−HRP); donkey anti-rabbit-HRP conjugate; anti-S6 p240/44 rabbit polyclonal (HRP conjugated); anti-S6 mouse monoclonal (biotinylated); anti-AKT pT308 rabbit monoclonal (HRP conjugated); anti-AKT mouse monoclonal (biotinylated); anti-AKT pS473 mouse monoclonal (biotinylated); and anti-AKT rabbit monoclonal (HRP conjugated).

Other reagents and materials used in the following examples include: QuantaRed™ enhanced chemifluorescent HRP substrate (Thermo Scientific); SIGMAFAST™ OPD tablets (Sigma); 96 well clear immunoassay Maxisorp™ plates (Nunc); 384 well clear immunoassay Maxisorp™ plates (Nunc); Streptavidin (Sigma); Blocking solution (1% BSA in PBS containing 0.05% polyethylene glycol sorbitan monolaurate sold under the trademark TWEEN 20); and A431 cell lysate containing pERK.

Example 2

Methods

1-Wash ELISA Protocol

Nunc 96 well Maxisorp™ plates were passively coated with streptavidin and blocked. pERK cell lysates (50 µL) were added to wells followed by the addition of a reaction buffer (50 µL) containing pre-optimised concentrations of biotinylated anti-pERK mouse mAb and anti-total ERK-HRP rabbit mAb (alternatively a reaction buffer containing biotinylated anti-pERK mouse mAb, anti-total ERK rabbit mAb and anti-rabbit IgG-HRP can be used).

In certain cases a pre-incubation of pERK cell lysate with the antibodies was performed in a sample plate prior to transfer to the streptavidin coated plate. Plates were incubated for a minimum of 30 min before washing 3× with PBS-T, addition of HRP substrate (100 µL) and measurement of product. A similar 1-wash protocol was followed when using Nunc 384 well Maxisorp™ plates. The specific kinase antibodies were supplemented into the protocol and the final reaction volume was 20 µL.

Comparative Multi-Wash ELISA Protocol—Streptavidin Coated Plate

Nunc 96 well Maxisorp™ plates were passively coated with streptavidin and blocked. Biotinylated anti-pERK mouse mAb was added to wells and incubated for a minimum of 30 min (100 µL). Plates were washed 3× with PBS-T. pERK cell lysates were added to wells and incubated for a minimum of 30 min (100 µL). Plates were washed 3× with PBS-T. Anti-total ERK-HRP rabbit mAb was added to wells and incubated for a minimum of 30 min (100 µL). Plates were washed 3× with PBS-T before addition of HRP substrate (100 µL) and measurement of product.

Comparative Multi-Wash ELISA Protocol—Anti-pERK IgG Coated Plate

Nunc 96 well Maxisorp™ plates were passively coated with anti-pERK mouse mAb and blocked. pERK cell lysates were added to wells and incubated for a minimum of 30 min (100 µL). Plates were washed 3× with PBS-T. Anti-total ERK-HRP rabbit mAb was added to wells and incubated for a minimum of 30 min (100 µL). Plates were washed 3× with PBS-T before addition of HRP substrate (100 µL) and measurement of product.

Example 3

Results

Assay Characteristics

Speed/Simplicity

Figure 1B:
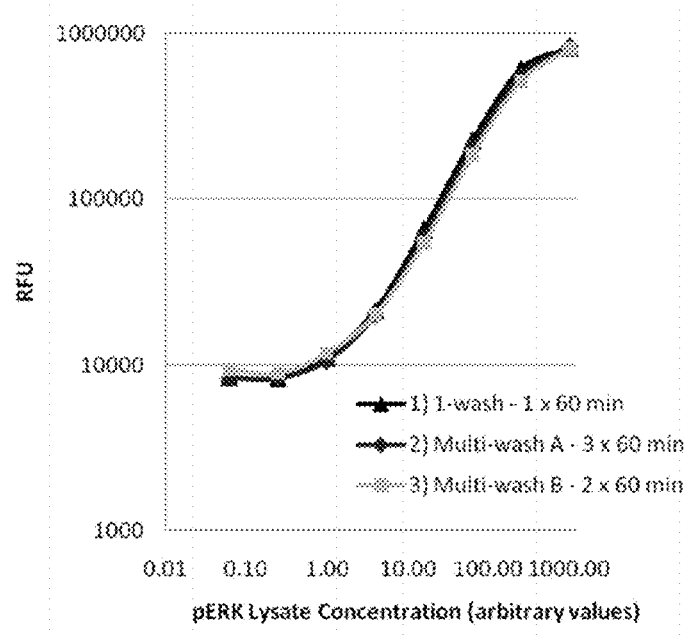

In their optimized formats, the 1-wash assay performed comparably to the multi-wash assay in terms of sensitivity (FIG. 1). This was evident on both streptavidin (Protocols 1 & 2) and anti-pERK IgG (Protocol 3) coated plates for the 30 min (FIG. 1A) and 60 min incubation periods (FIG. 1B). Generally, there was approximately a 10% greater signal obtained at each respective pERK concentration in the 1-wash ELISA compared to the multi-wash ELISAs but this did not translate to a significant improvement in the assay detection limit. Importantly, this demonstrated that the 1-wash assay could be performed with less handling steps and in less than half the time of the multi-wash ELISAs without negatively impacting on sensitivity. This translated to a much simpler ELISA assay format by the consolidation of multiple steps into a single 1-wash/step system.

Sensitivity

Figure 2A:
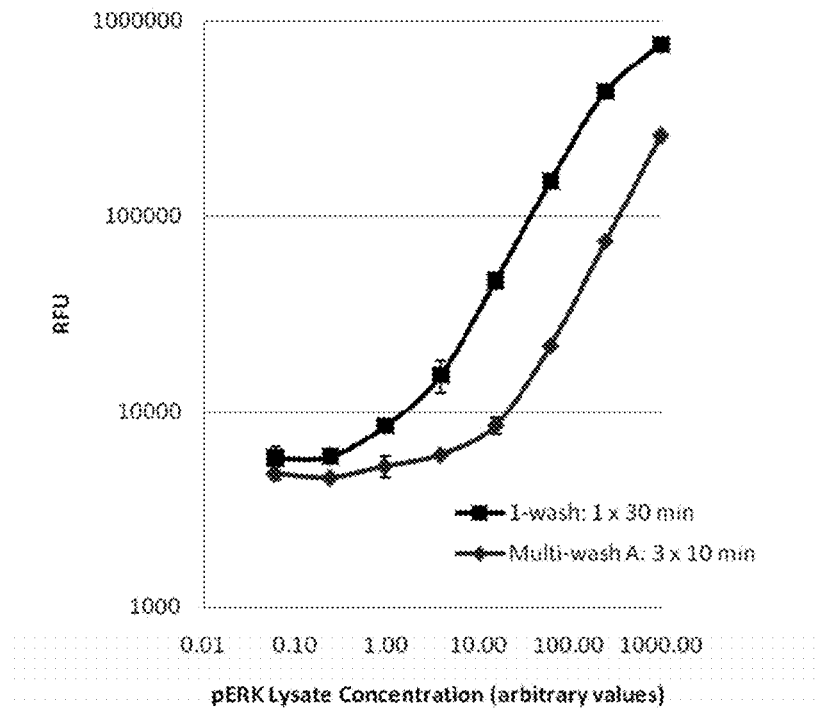
FIGS. 2A and 2B show the mean and standard deviations for the duplicate data points at each pERK lysate concentration analyzed. In this Figure, the comparison clearly demonstrate better assay performance the same total assay time period when the assay components are incubated concurrently, compared with standard ELISA protocols whereby assay components are incubated sequentially.
Figure 2B:
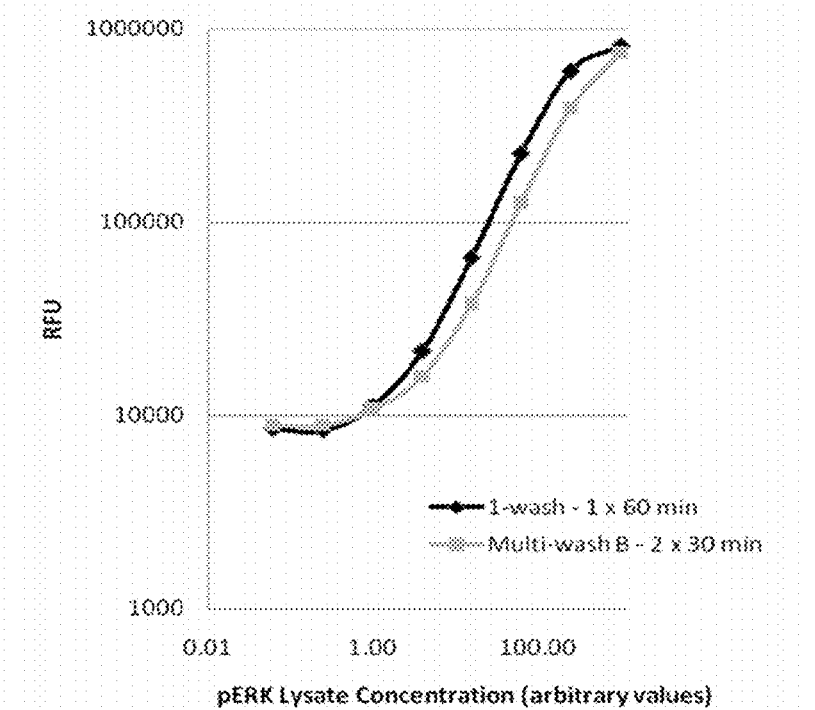

When the 1-wash and multi-wash ELISAs were performed for the same total length of time of 1 h or less, the 1-wash ELISA was superior in sensitivity (FIG. 2). Comparison of a 1×30 min incubation step to 3×10 min incubation steps on a streptavidin coated plate (2A) showed that the 1-wash system was approximately 10 times more sensitive than the multiwash system. Although not as significant, this trend was also noticeable when comparing a 1×60 min 1-wash assay system on a streptavidin plate, to a 2×30 min multiwash system on an anti-pERK IgG coated plate (2B). The major benefit of the 1-wash ELISA protocol was that it allowed multiple antibody-antigen binding events to occur simultaneously in the single 30 or 60 minute incubation period thereby improving the pERK detection capabilities per unit time.

Capture Antibody Efficiency

Figure 3:
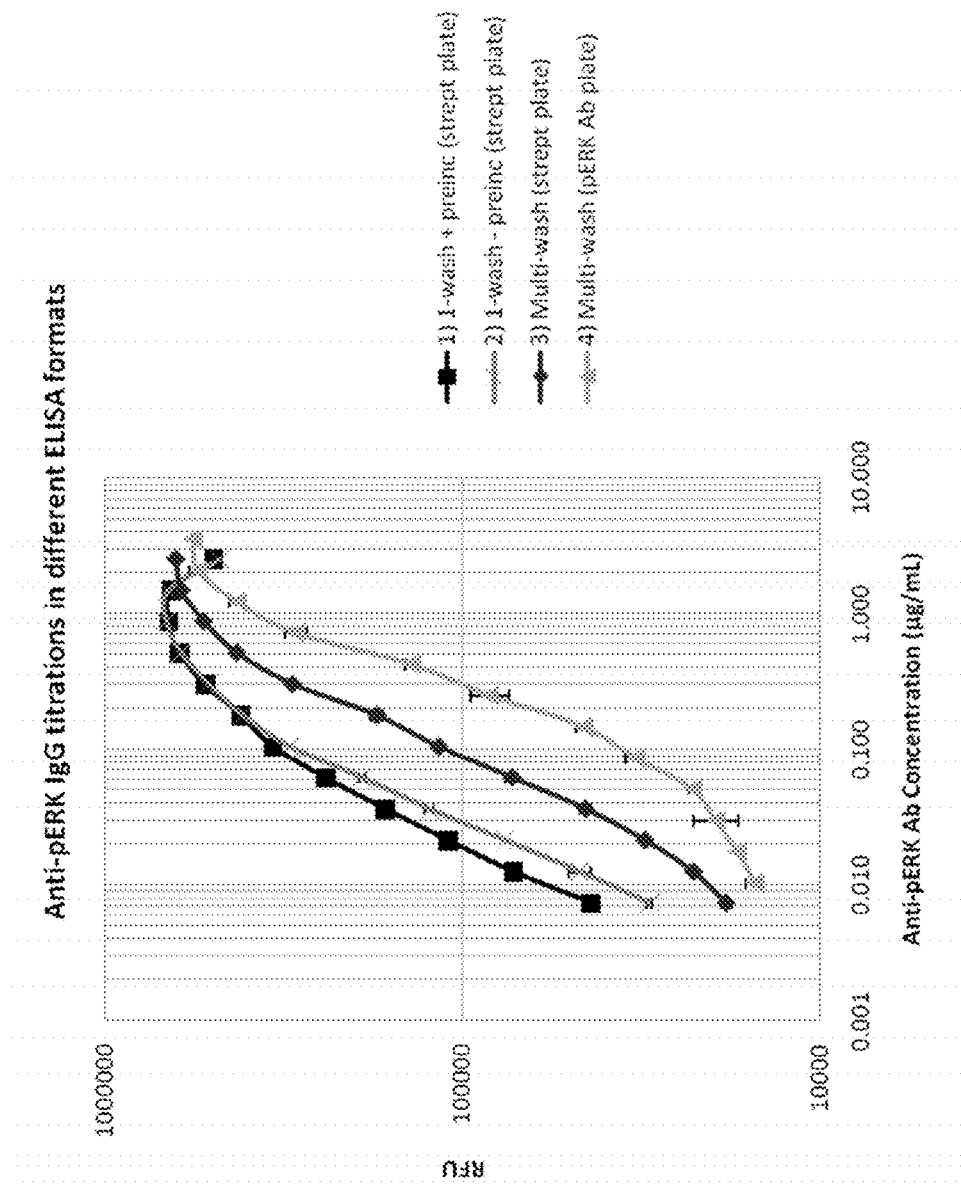
FIG. 3 shows for the purposes of comparison, the concentration of the capture antibody (anti-phospho-ERK) required for optimal assay performance for three ELISA protocols for the detection of phosphorylated ERK 1/2, using varying concentrations of the capture antibody in combination with a fixed concentration of both cellular lysate, and detection antibody. (1) A simultaneous ELISA format, whereby the assay components, namely the capture antibody (anti-pERK-biotin), the analyte (cellular lysate), and the detection antibody (anti-ERK-HRP), were incubated concurrently in a streptavidin-coated microplate for 120 min. (2) A simultaneous ELISA format, whereby the assay components, namely the capture antibody (anti-pERK-peptide), the analyte (cellular lysate), and the detection antibody (anti-ERK-HRP), were incubated concurrently in an anti-peptide antibody-coated microplate for 120 min. (3) A standard multi-incubation ELISA format, whereby the analyte was incubated in a capture-antibody (non-biotinylated) coated microplate for 120 min, followed by the detection antibody for 120 min. The wells were subjected to a standard wash cycle between each incubation step for each assay. After the wash cycle, HRP substrate was added to the wells, and the plates were incubated for 10 min in the dark. The fluorescent signal in the wells was measured at 540ex/590em nm.

The concentration dependency of anti-pERK IgG (+/−biotinylation) for detecting pERK was assessed in each of the ELISA protocols (FIG. 3). With or without a pre-incubation step, the 1-wash protocol required approximately 4× and 10× less anti-pERK IgG, to detect the same amount of pERK when compared to multi-wash ELISA protocols 3 and 4 respectively. The importance of a pre-incubation step (protocol 1 vs protocol 2) in the 1-wash ELISA was noticeable when the anti-pERK IgG concentrations were 100 ng/mL or less. At these lower concentrations, more pERK per unit antibody (approx 15% higher signal) was able to be detected when a pre-incubation step was incorporated into the 1-wash protocol. Collectively, these results indicated that the 1-wash protocol was more efficient with its use of anti-pERK IgG compared to the multi-wash format for detecting the same amount of pERK. A possible explanation for this phenomenon was that the 1-wash format allowed the formation of solution-phase pERK immune complexes, enabling their binding to the streptavidin or anti-pERK IgG coated surface in a more orientated fashion thereby enhancing antibody functionality. Conversely, in the absence of pERK and detection IgG, biotinylated or unbiotinylated anti-pERK IgG could bind randomly to the surface, which may have led to a portion of pERK IgG binding sites becoming inaccessible to pERK and/or sterically hindering subsequent binding events in the sandwich (i.e. detection IgG).

Figure 4:
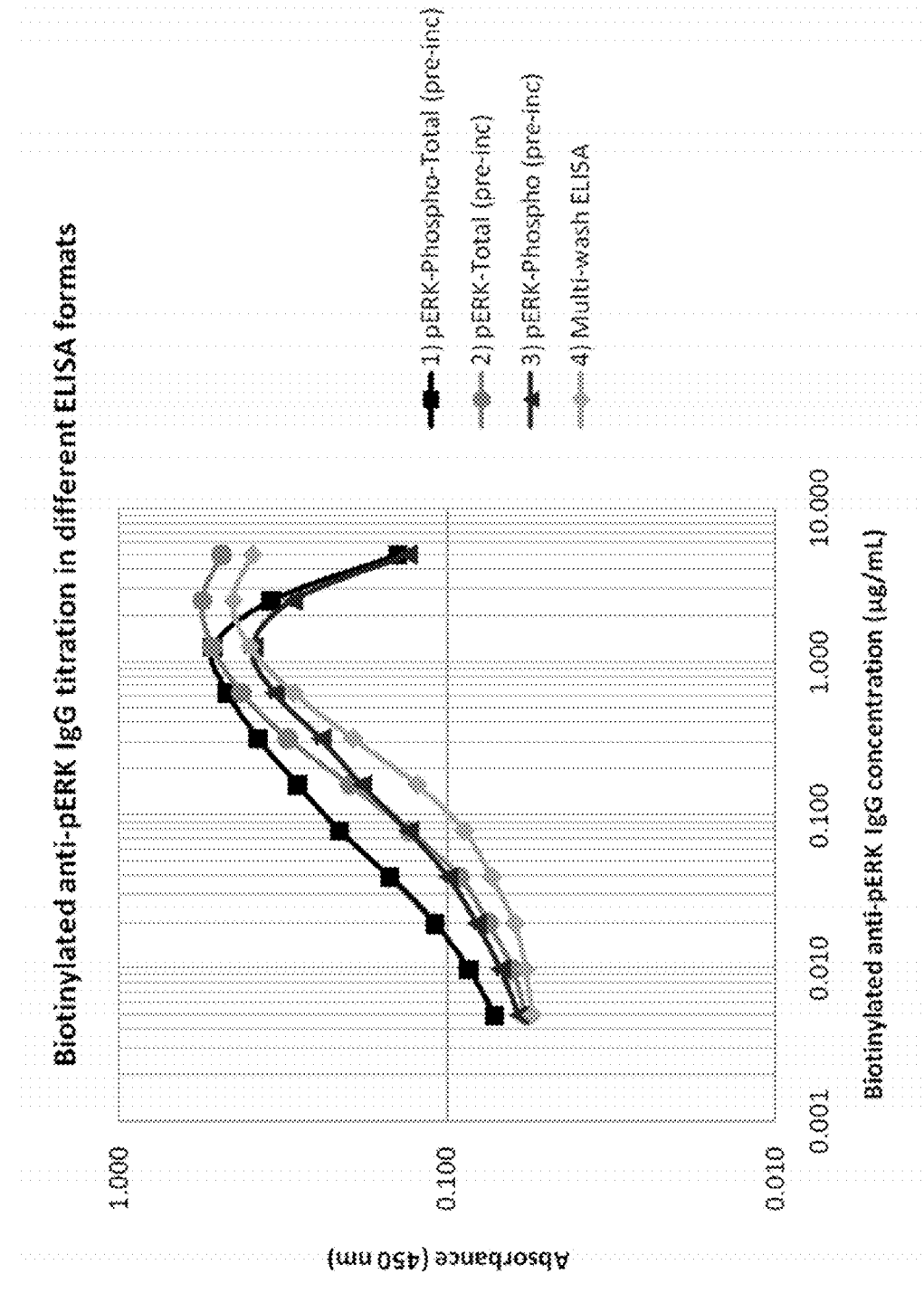
FIG. 4 shows for the purposes of comparison, the requirement for sequential incubations for optimal assay performance for two ELISA protocols for the detection of phosphorylated ERK 1/2. (1) A simultaneous ELISA format, whereby the assay components, namely the capture antibody (anti-phospho-ERK-peptide), the analyte (cellular lysate), and the detection antibody (anti-ERK-HRP), were incubated concurrently in an antipeptide antibody-coated microplate for 120 min. (2) A sequential ELISA format, whereby the solution-phase assay components, namely the capture antibody (anti-pERK-peptide), the analyte (cellular lysate), and the detection antibody (anti-ERK-HRP), were incubated concurrently in a separate reaction vessel for 60 min. The assay components were subsequently transferred to an antipeptide antibody-coated microplate for 60 min. At the conclusion of incubation on the antipeptide antibody-coated assay microplate, both protocols required a standard wash cycle. After the wash cycle, HRP substrate was added to the wells, and the plates were incubated for 10 min in the dark. The fluorescent signal in the wells was measured at 540ex/590em nm.

The improved anti-pERK IgG efficiency phenomenon highlighted in FIG. 3 for the 1-wash ELISA format was investigated further by separating the multiple antibody-antigen binding events of the pERK assay (FIG. 4). This highlighted that independent formation of pERK with anti-total ERK-HRP IgG or anti-pERK IgG (protocols 2 & 3 respectively), prior to binding to their immobilized partner on the plate, contributed to the more efficient use of anti-pERK IgG in the 1-wash ELISA format. Individually, protocols 2 & 3 were approximately 2 times more efficient with their use of anti-pERK IgG for detecting pERK compared to the multi-wash ELISA (protocol 4). Furthermore when the individual binding events of protocols 2 & 3 were allowed to occur simultaneously as part of the 1-wash ELISA (protocol 1), the use of anti-pERK IgG compared to the multi-wash procedure was 4-5 times less when measuring the same concentration of pERK. Ultimately this highlighted that the binding of both antibodies to pERK in solution were important for enhancing the functionality of the anti-pERK IgG used in the 1-wash ELISA. This would result in less reagent use (i.e. antibody) and therefore reduced assay cost, compared to the multi-wash ELISA format.

Versatility

Figure 5:
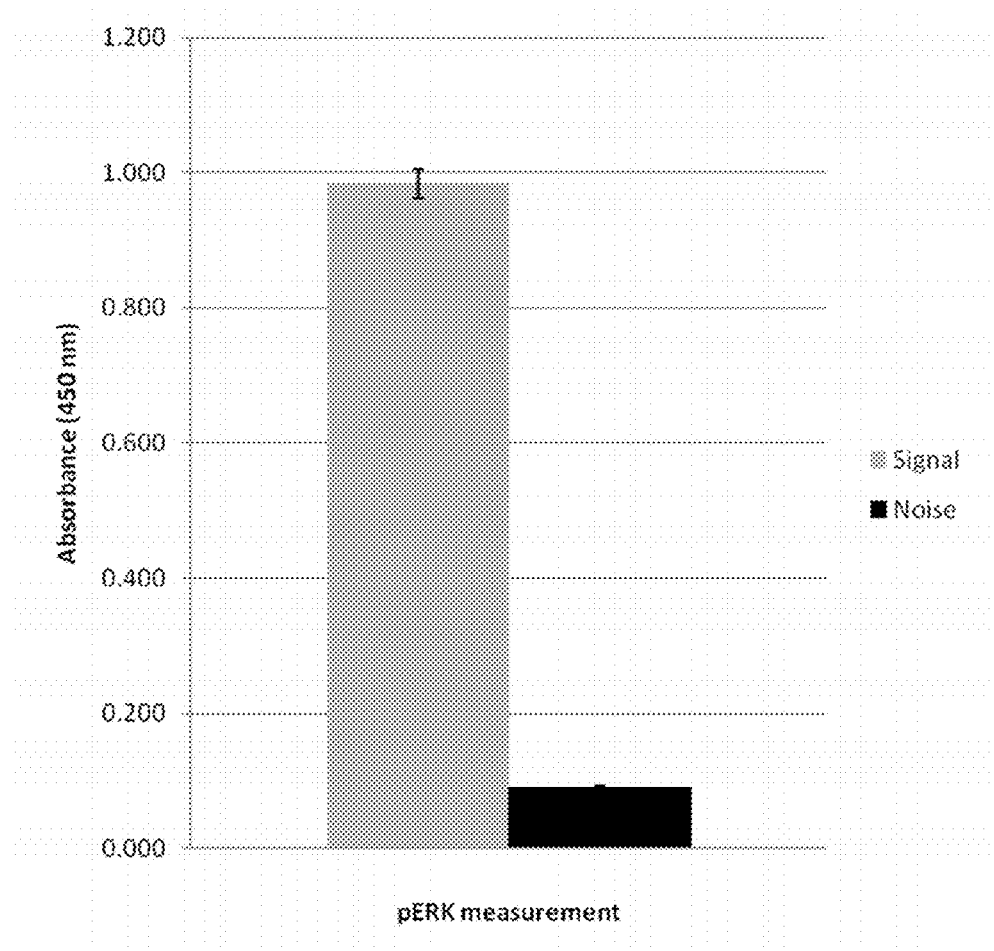
FIG. 5 shows a single-incubation, single-wash ELISA, was performed using a 3-antibody configuration. The assay components, namely the capture antibody (anti-pERK-biotin), the analyte (cellular lysate), the detection antibody (rabbit anti-ERK), and a generic anti-rabbit-HRP antibody, were incubated concurrently in a streptavidin-coated microplate for 120 min (signal), and compared with a similar assay run with a buffer-only control for the analyte (noise). The wells were subjected to a standard wash cycle after the incubation step, and SigmaFAST™ HRP substrate was added to the wells, and each plate was incubated for 10 min in the dark. The colorimetric signal in the wells was measured at 450 nm.

The 1-wash ELISA protocol was also challenged using a secondary detection antibody that was conjugated to HRP (FIG. 5). This was achieved by replacing the anti-total ERK-HRP with the original unconjugated antibody (i.e. minus HRP) and introducing anti-rabbit IgG-HRP as the secondary detection antibody. That is, this experiment used a 3 antibody protocol in the 1-wash ELISA format and yielded an A450 signal for pERK of approximately 1.0 AU and a signal:noise value of 10. Although unoptimized, in principle this secondary detection approach was validated in a 1-wash protocol and highlighted the versatility of the 1-wash ELISA using at least 3 antibodies.

Robustness

Figure 6:
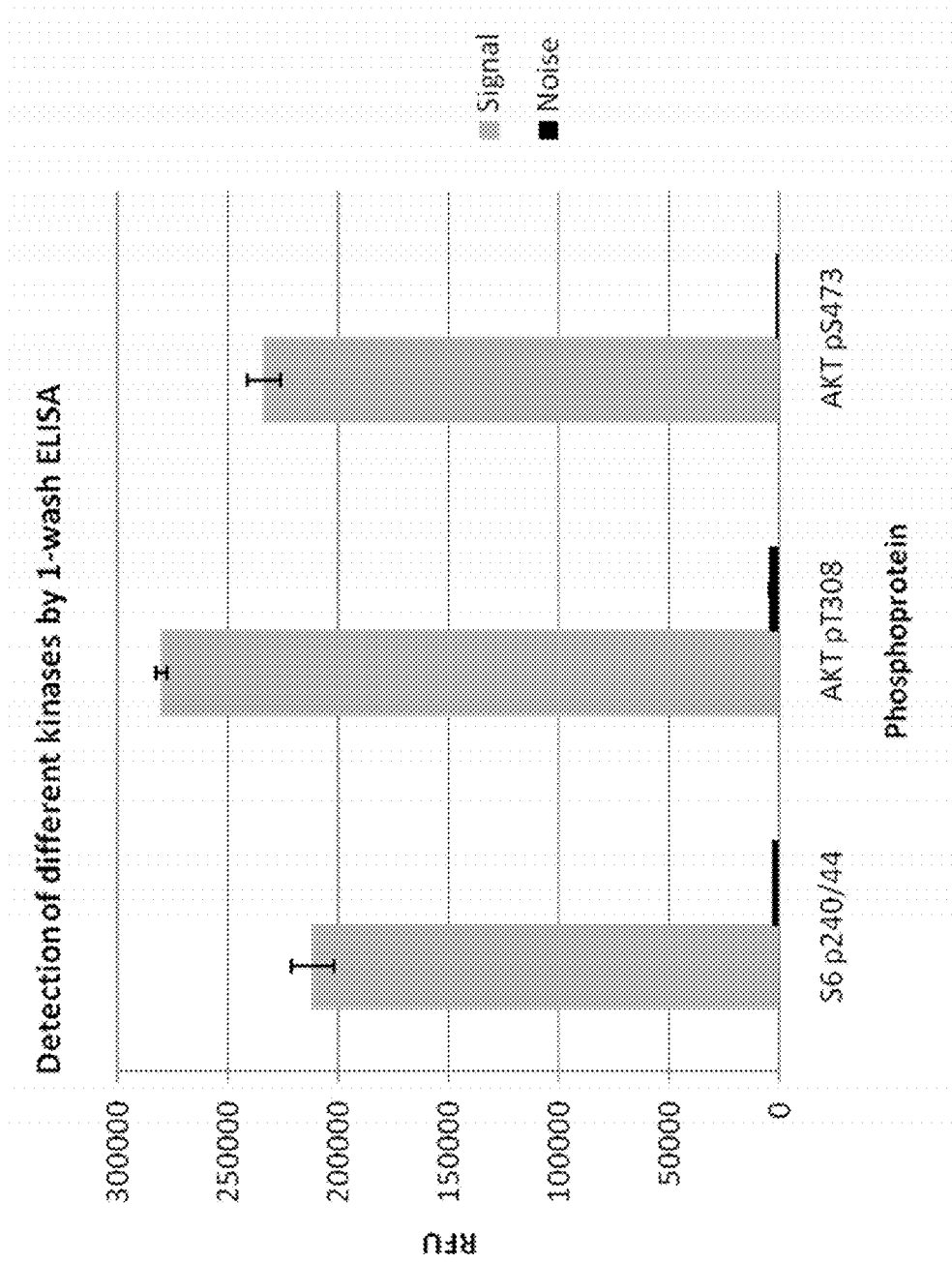
FIG. 6 shows the detection of different kinases by a single incubation, single wash ELISA. Cell lysates containing either phosphorylated S6 p240/44, AKT pT308 or AKT pS473 (signal), or buffer-only controls (noise) were added to separate wells of an assay microplate (streptavidin coated 384-well Nunc Maxisorp™ plate). The reaction was started by the addition of target-specific antibody pairs (one biotinylated and the other conjugated to HRP) to the lysates. The assays were incubated for 2 h, then subjected to a wash cycle. After the wash cycle, QuantaRed™ HRP substrate was added to the wells, and the plate was incubated for 10 min in the dark. The fluorescent signal in the wells was measured at 550ex/600em nm.

Detection of other phosphoproteins including S6 p240/44, AKT pT308 and AKT pS473 was also achieved in the 1-wash ELISA system (FIG. 6). In 384 well streptavidin coated plates, signal:noise ratios of greater than 60 were achieved when assaying cell lysates containing the specific phosphoproteins of interest. Like the pERK protocol, the AKT pS473 assay also used an anti-phospho IgG as the capture antibody with an anti-total IgG used as the detection antibody (i.e. conjugated to HRP). Alternatively the S6 p240/44 and AKT pS473 assays used an anti-total IgG as the capture antibody, with a specific anti-phospho IgG-HRP completing the sandwich. These results demonstrated the robustness of the 1-wash ELISA with its ability to detect different targets in varying immune complex orientations.

Example 4

Microfluidics

Figure 7:
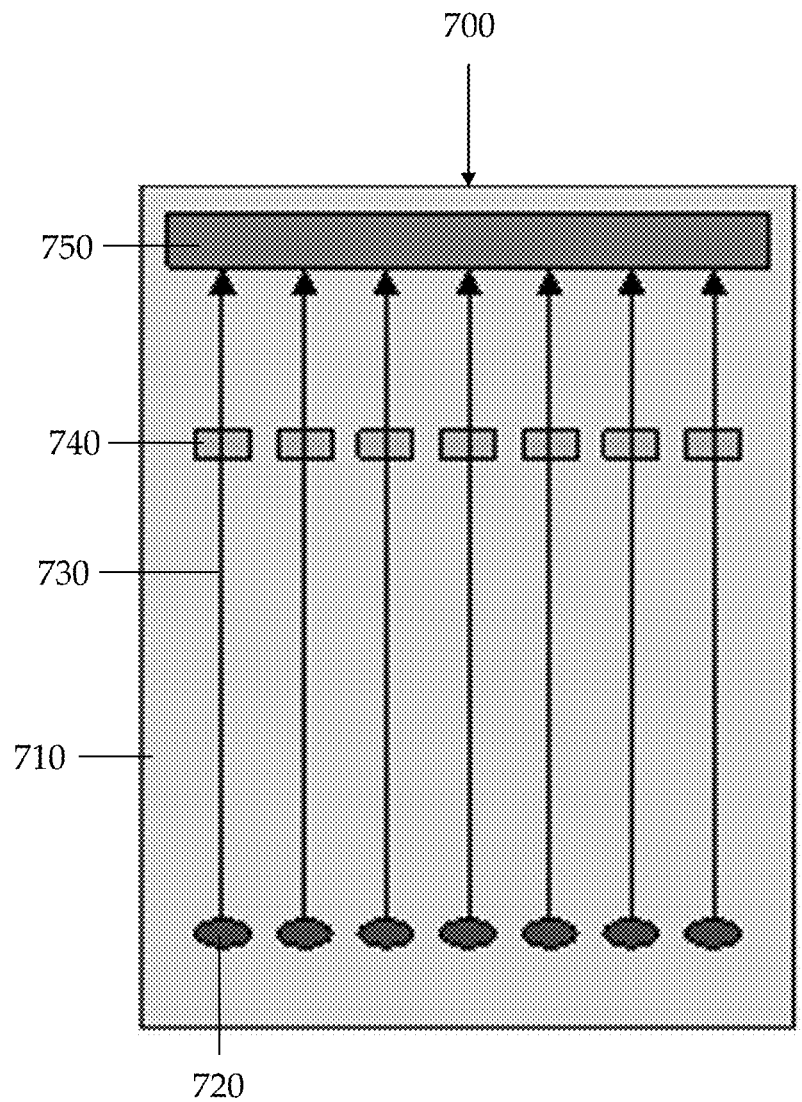
FIG. 7 is a schematic diagram showing a microfluidic cartridge suitable for use in accordance with some embodiments of the methods of the present disclosure.

Microfluidic reactions were performed in a microfluidic cartridge as shown in FIG. 7.

Referring to FIG. 7, the microfluidic cartridge 700 comprises a plastic substrate 710 into which a plurality of flow channels 730 are formed. A sample is introduced into the flow channel 730 via sample inlet 720. The sample is then driven along flow channel 730 by a pump (not shown). Detection region 740 comprises an electrode for electrochemical detection to which an immobilization agent is bound. In the embodiments described in the following examples, the immobilization agent is streptavidin. Moreover, although the present invention contemplates any suitable electrodes and methods for electrochemical detection, the method described in the following examples utilizes the electrodes and detection methods described in U.S. Pat. No. 6,770,190. After passing over detection area 740, the sample is transported to waste collection area 750.

An example of the method of the present invention performed in the microfluidic cartridge is described below:

Samples were mixed with a reaction buffer (phosphate buffered saline, BSA 0.3%, polyethylene glycol sorbitan monolaurate sold under the trademark TWEEN 20 0.1%) containing two antibodies to the analyte of interest. For each analyte, the two antibodies were raised against distinct epitopes on the analyte of interest, such that both antibodies could bind to the protein of interest simultaneously. One of the antibodies performed the function of a capture agent and had biotin attached to it, while the other antibody performed the function of a detectable agent and was linked to horse radish peroxidise (HRP).

The samples being measured contained varying amounts of an analyte of interest, in the present examples either phospho-ERK or phospho-AKT. A microfluidic cartridge (see FIG. 7) was placed on a pumping and detection instrument, and samples were drawn onto the microfluidic cartridge into separate lanes of the cartridge. The cartridge bound the biotinylated antibody at the detection region. As set out above, the detection region comprised an electrode for electrochemical detection to which streptavidin is bound as an immobilisation agent. As such, a complex comprising biotinylated capture antibody, bound analyte and HRP-linked detectable antibody would become immobilised to the electrode via interaction of the biotin on the capture antibody and streptavidin on the electrode.

After capture, the cartridge was automatically washed with buffer without antibodies. Following this wash step, a solution containing HRP substrate (SigmaFAST OPD) was drawn over the cartridge, allowing bound HRP to convert the HRP substrate to products that could be detected electrochemically by the electrode and detection equipment present on the pumping device. The electrical signals generated were proportional to the level of HRP-induced product conversion, which was proportional to the amount of analyte bound to the capture antibodies.

Example 5

Detection of pERK Using a Microfluidic System

Recombinant pERK was diluted in 1× lysis buffer, with four fold dilutions from a top concentration of 400 ng/ml (10 nM). Samples were pre incubated with an equal volume of reaction buffer (see above).

Figure 8A:
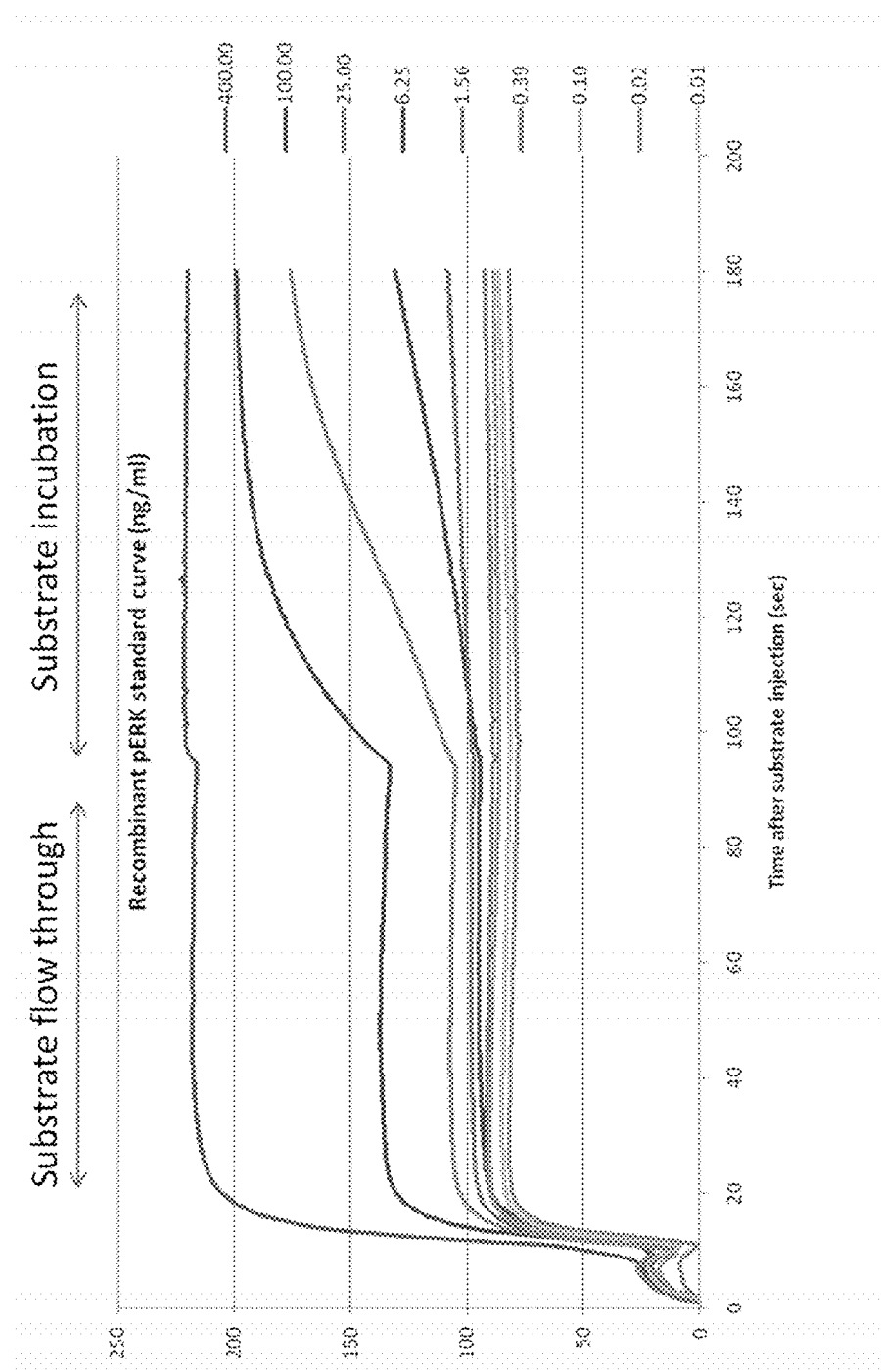
FIG. 8A shows the raw results of electrochemical detection (in mV) during the substrate flow through phase and substrate incubation phase.
Figure 8B:
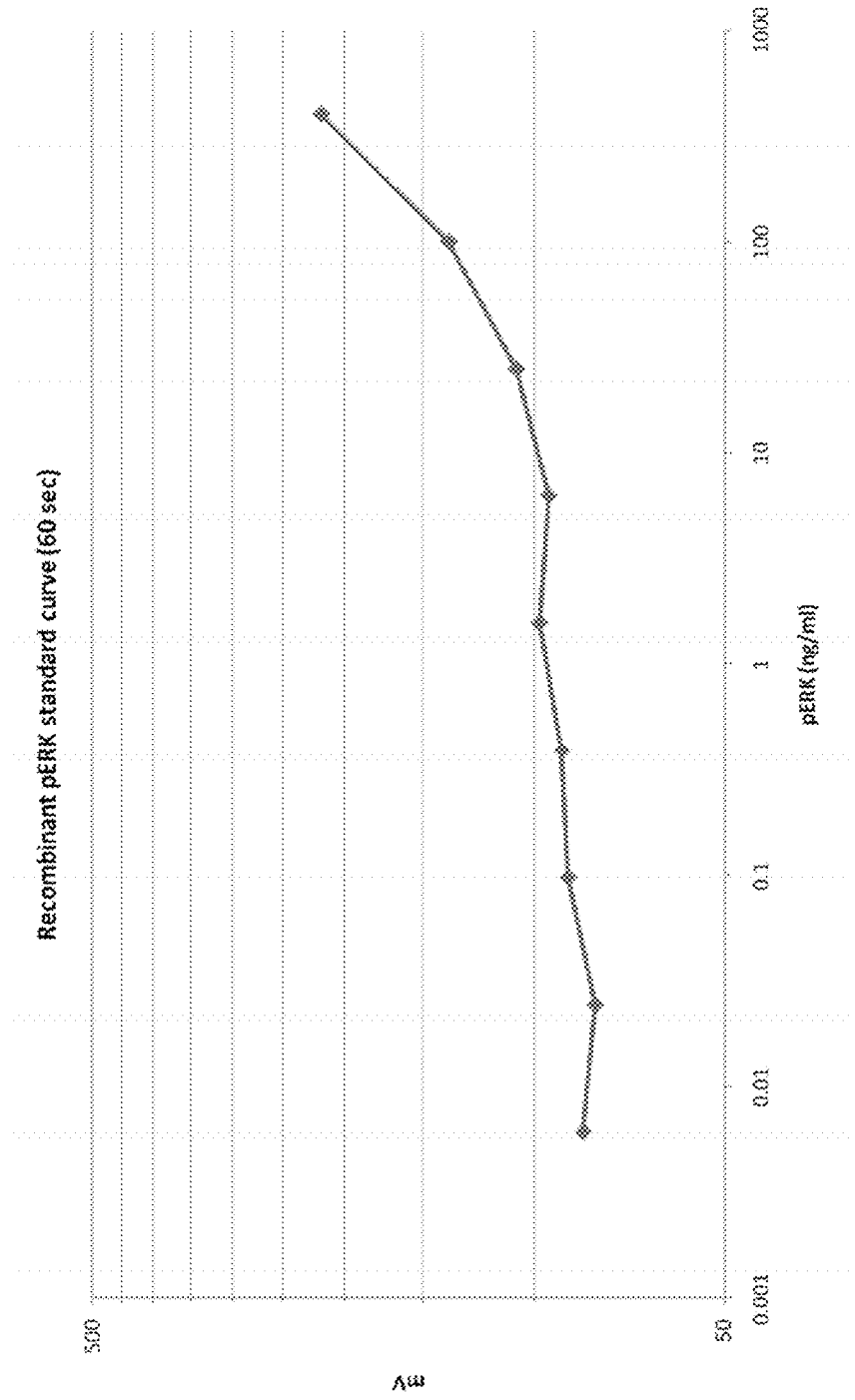
FIG. 8B shows a pERK standard curve generated using data taken from 60 seconds after injection of substrate (during flow through phase).
Figure 8C:
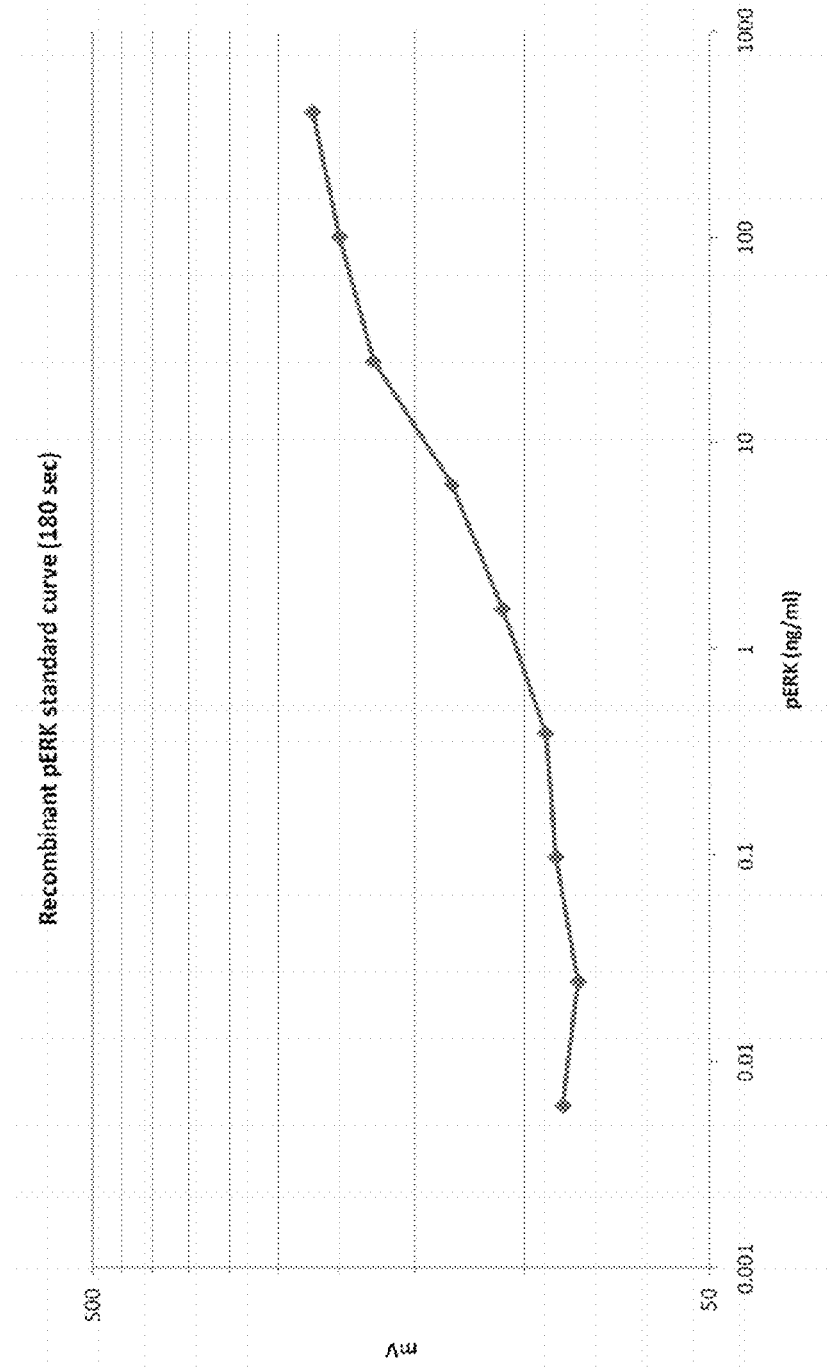
FIG. 8C shows a pERK standard curve generated using data taken from 180 seconds after injection of substrate (at the end of the substrate incubation phase).

The sample/reaction buffer mix was then run on a microfluidic cartridge as described in Example 4. The results are shown in FIGS. 8A-8C. Each data point shown is the average of 3 flow cells from a single cartridge. The data was transformed by taking the point at which substrate injection begins as zero. Data was collected from the point at which substrate flow through begins up until the end of substrate incubation phase (180 s after substrate injection).

As can be seen by comparing FIGS. 8*b* and 8*c*, data collection at the end of the substrate incubation phase (180 s after substrate injection) appeared to provide greater sensitivity. Using the data taken from 180 seconds after injection of substrate, the detection limit of the chip was about 2 ng/ml pERK.

Example 6

Detection of pAKT Using a Microfluidic System

Recombinant pAKT473 was diluted in 1× lysis buffer, with five fold dilutions from a top concentration of 100 ng/ml. Samples were pre incubated for two hours with an equal volume of reaction buffer (see above) to equilibrate the interaction and so minimise incubation effects during the run.

Figure 9A:
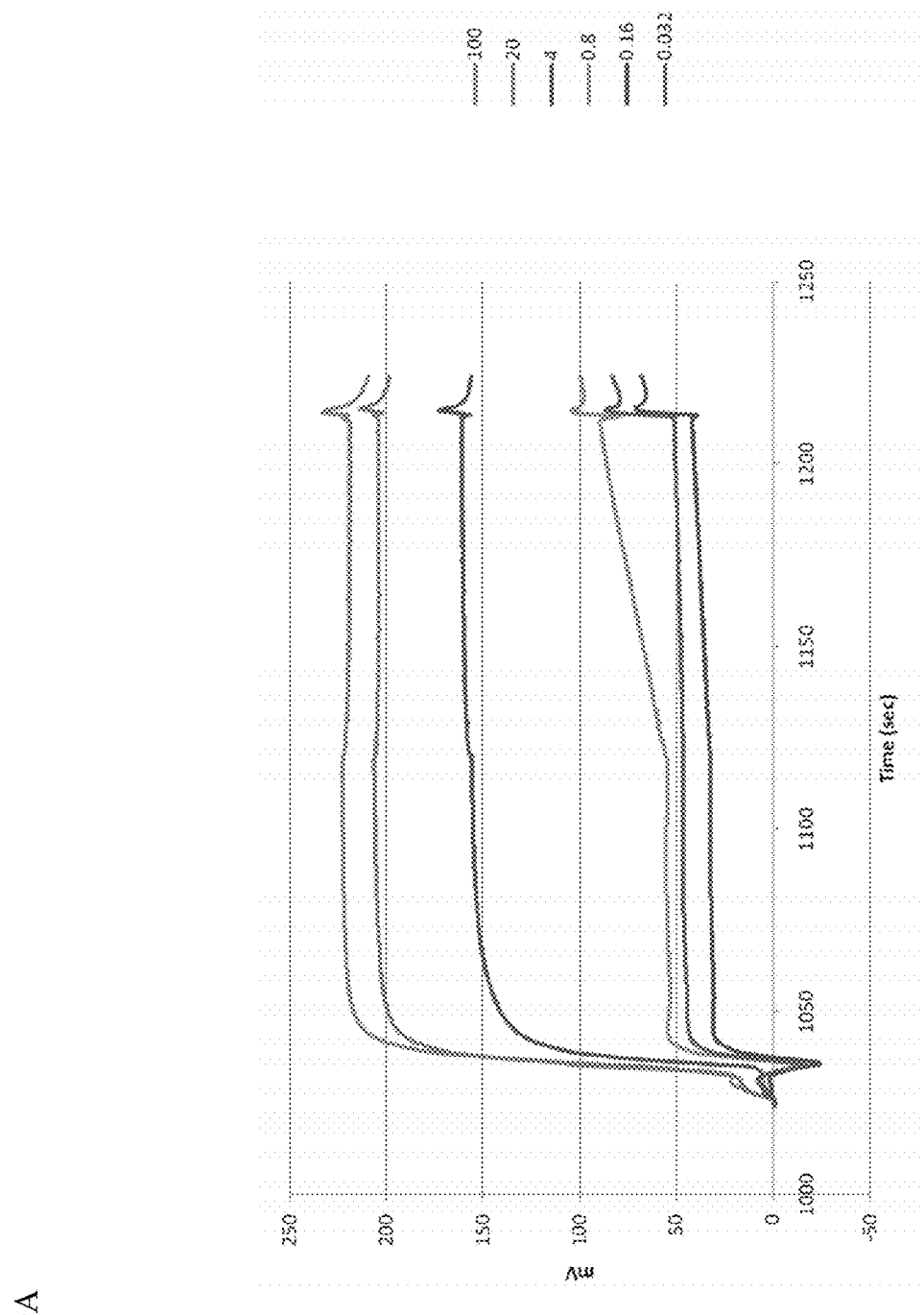
FIG. 9A shows the raw results of electrochemical detection (in mV) during the substrate flow through phase and substrate incubation phase.
Figure 9B:
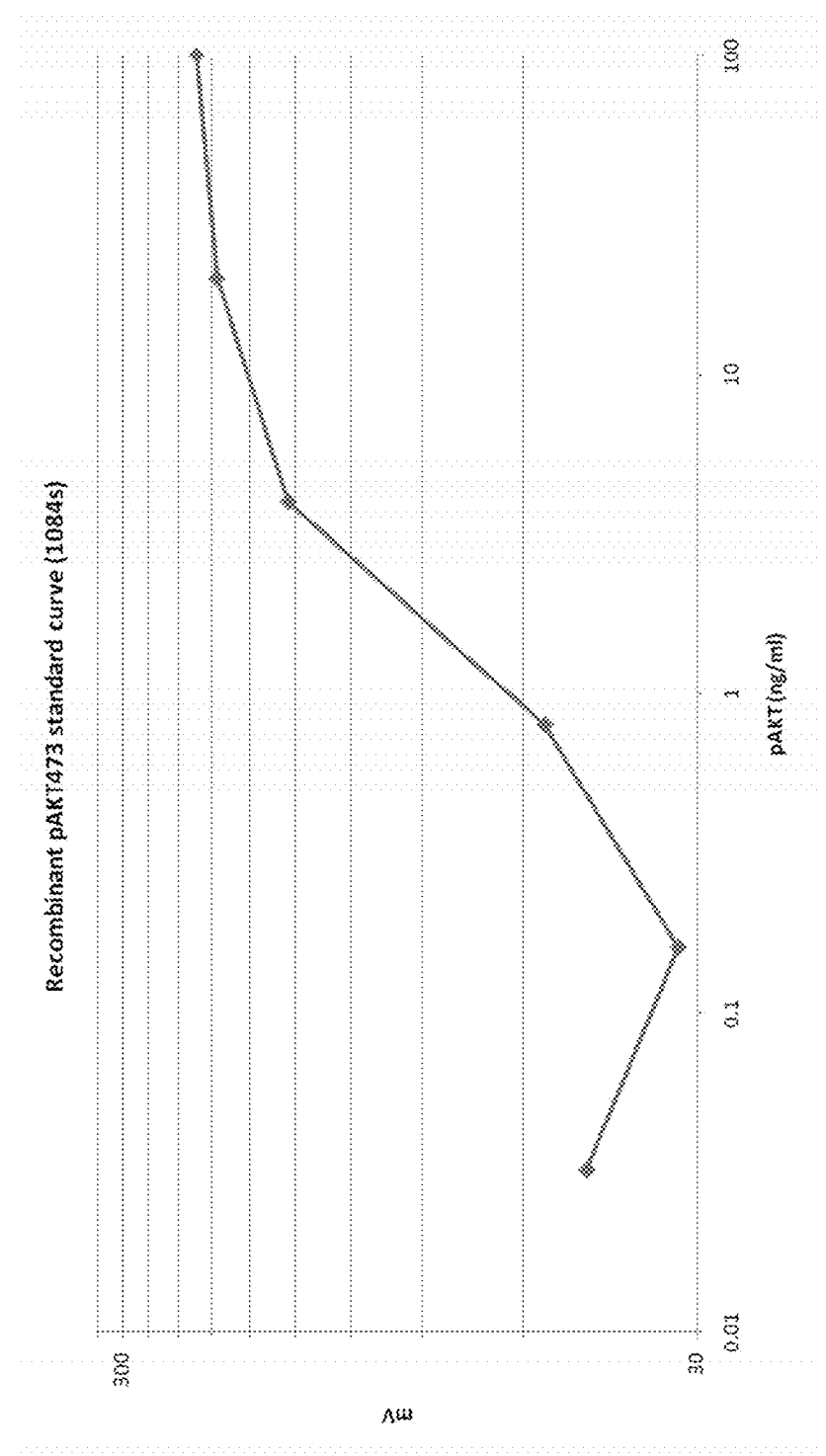
FIG. 9B shows a pAKT473 standard curve generated using data taken from 60 seconds after injection of substrate (during flow through phase).
Figure 9C:
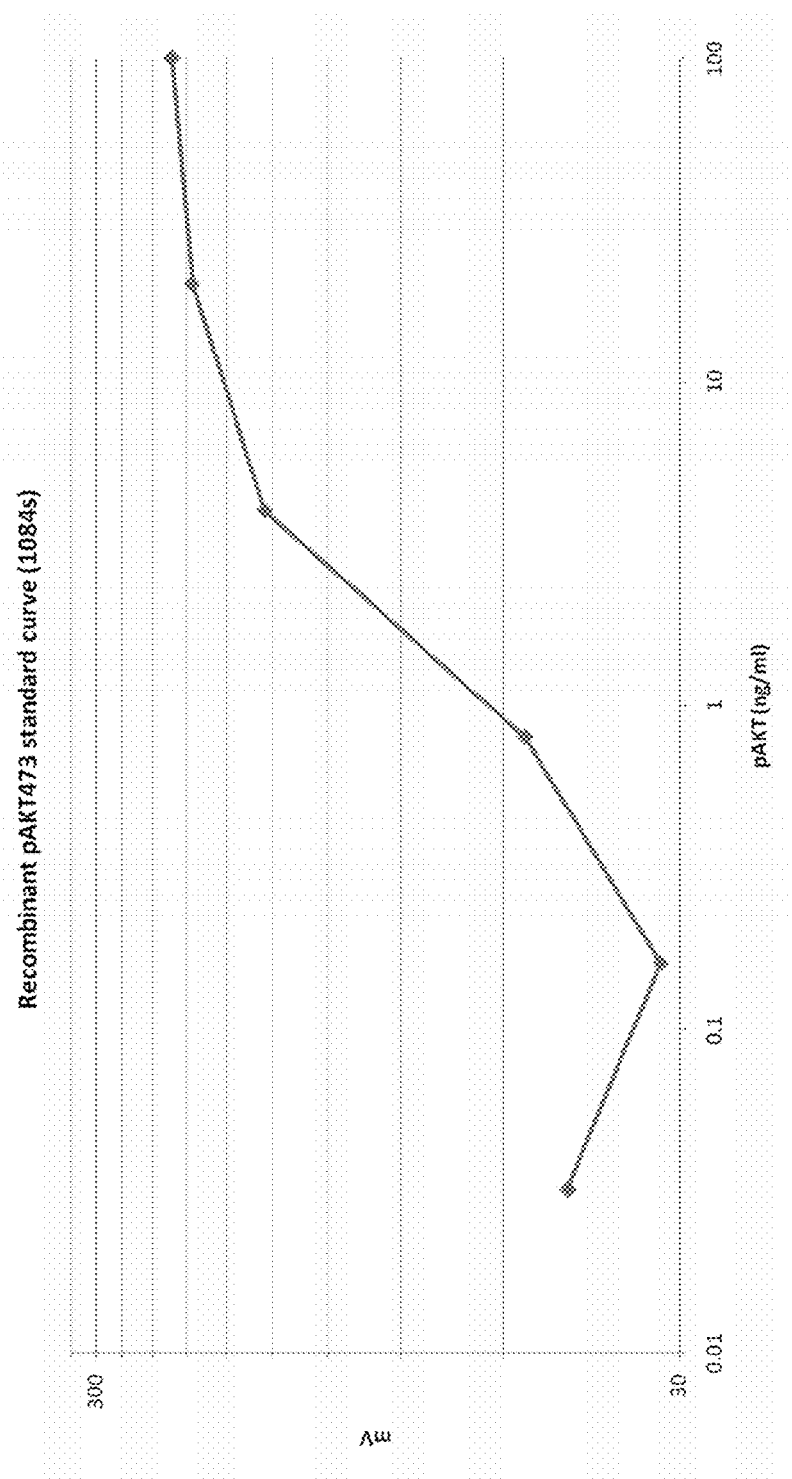
FIG. 9C shows a pAKT473 standard curve generated using data taken from 180 seconds after injection of substrate (at the end of the substrate incubation phase).

The sample/reaction buffer mix was then run on a microfluidic cartridge as described in Example 4. The results are shown in FIGS. 9A-9C. Each data point shown is the average of 3 flow cells from a single cartridge. The data was transformed by taking the point at which substrate injection begins as zero. Data was collected from the point at which substrate flow through begins up until the end of substrate incubation phase (180 s after substrate injection).

Using the data taken from 180 seconds after injection of substrate, the detection limit of the chip was about 1 ng/ml pAKT.

Example 7

Reagent Order of Addition Permutations

Capture antibody (anti-pERK-peptide conjugate or anti-pERK-biotin conjugate), detection antibody (anti-total ERK-HRP conjugate), capture/detection antibody mixture, and varying concentrations of cell lysate containing pERK were added to (A) anti-peptide conjugate antibody coated plates or (B) streptavidin coated microplates, in 8 different permutations (refer to Table 1 & 2). Individual assay components were added 1 min apart to the plates, and incubated for 2 h. Plates were washed, incubated with HRP substrate, before detection of the fluorescent product.

TABLE 1

Reagent volumes for order of addition assessment

| Assay Component | Volume/Well |
|---|---|
| Capture/Detection Antibody Mix | 50 µl |
| Lysate | 50 µl |
| Capture Antibody | 25 µl |
| Detection Antibody | 25 µl |

TABLE 2

Reagent order of addition permutations

| Trial # | 1st Addition | 2nd Addition | 3rd Addition |
|---|---|---|---|
| 1 | Capture/Detection Ab Mix | Lysate | n/a |
| 2 | Lysate | Capture/Detection Ab Mix | n/a |
| 3 | Lysate | Capture Ab | Detection Ab |
| 4 | Lysate | Detection Ab | Capture Ab |
| 5 | Detection Ab | Capture Ab | Lysate |
| 6 | Detection Ab | Lysate | Capture Ab |
| 7 | Capture Ab | Lysate | Detection Ab |
| 8 | Capture Ab | Detection Ab | Lysate |

Figure 10A:
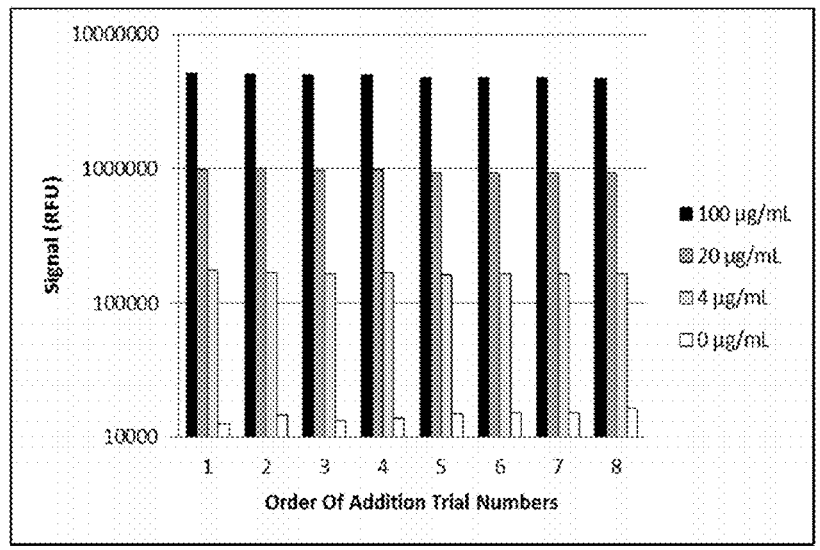
FIG. 10 demonstrates equivalent assay performance with various permutations on the order of delivery of assay components to the assay well, using a peptide capture antibody conjugate (anti-pERK-peptide) (FIG. 10A), or biotin capture antibody conjugate (anti-pERK-biotin) (FIG. 10B), as the assay capture reagent The assay components were added in various permutations (refer to example 7, Tables 1 and 2). Individual assay components were added 1 min apart to the plates and incubated for 2 h at room temperature, then subjected to a wash cycle. After the wash cycle, HRP substrate was added to the wells, and the plates were incubated for 10 min in the dark. The fluorescent signal in the wells was measured at 540ex/590em nm.
Figure 10B:
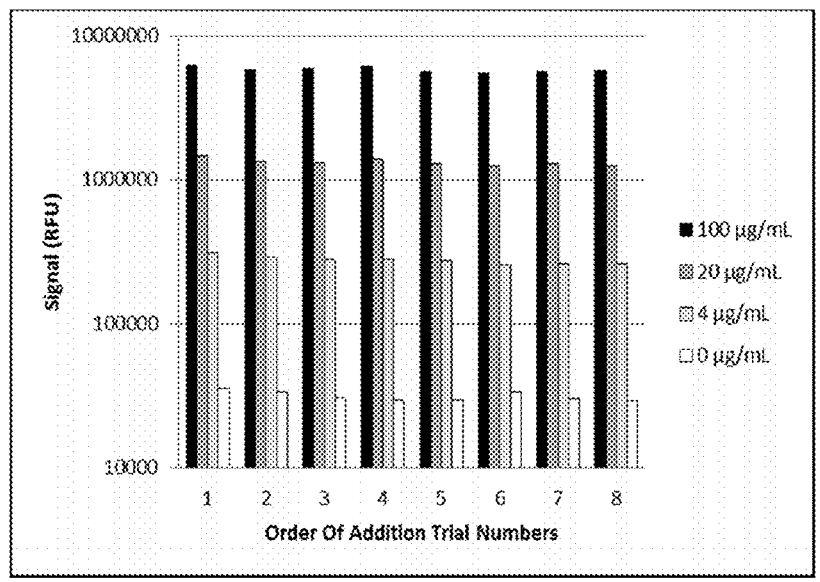

The effect of reagent order of addition on pERK detection in the single-incubation ELISA using different capture systems is shown in FIG. 10. Across the 8 different permutations, and at several analyte concentrations, little signal difference were observed. This result demonstrates that equivalent results can be obtained in a single-incubation ELISA assay, irrespective of the order of addition of the individual components.

Example 8

Figure 11A:
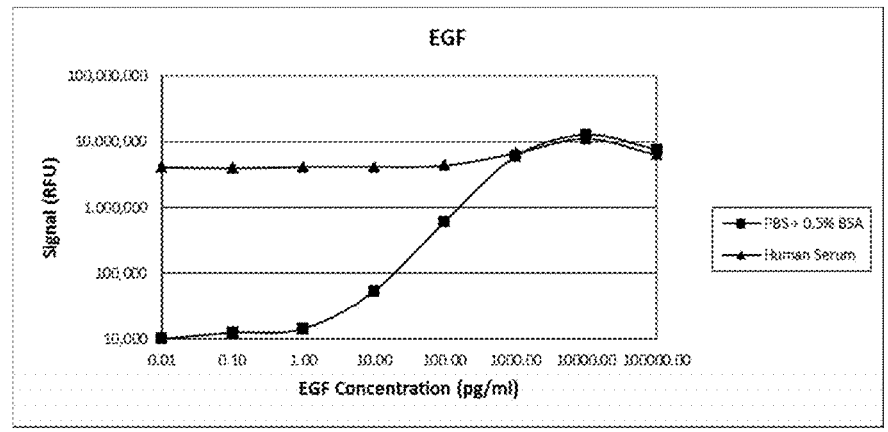
FIG. 11 shows detection of recombinant human EGF, IL-2 and TNFα, in either PBS/0.5% BSA or human serum. Peptide-capture antibody conjugates, and HRP-detection antibody conjugates specific for each of EGF (FIG. 11A), IL-2 (FIG. 11B) and TNFα (FIG. 11C) were prepared. Recombinant EGF, IL-2 or TNFα were prepared at concentrations ranging from 100 ng/mL to 10 fg/mL, in either PBS/0.5% BSA, or human serum, and 50 μL/well of each analyte was added to an ELISA assay plate coated with an anti-peptide antibody. The assays were initiated by addition of mixtures containing both specific antibodies for each of EGF, IL-2 or TNFα, along with a general anti-HAMA composition available commercially from Bioreclamation LLS (Westbury, N.Y., USA—'Immunoglobulin Inhibiting Reagent (IIR)), to the appropriate ELISA plate wells. The assays were incubated for 1 h, then subjected to a wash cycle. After the wash cycle, HRP substrate was added to the wells, and the plates were incubated for 10 min in the dark. The fluorescent signal in the wells was measured at 540ex/590em nm.
Figure 11B:
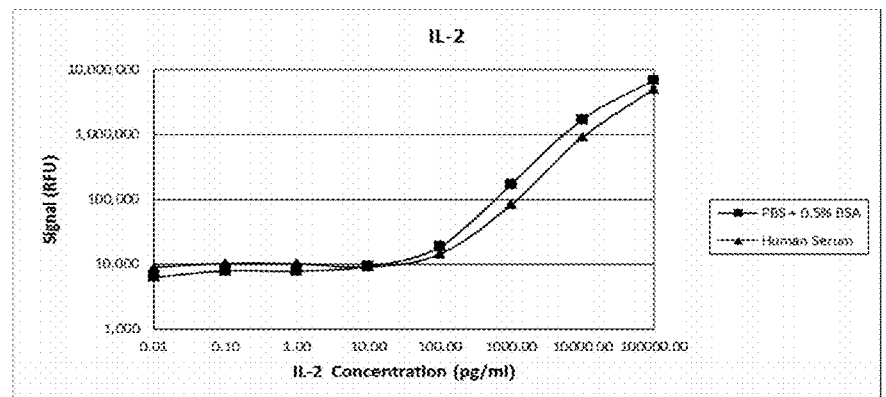
Figure 11C:
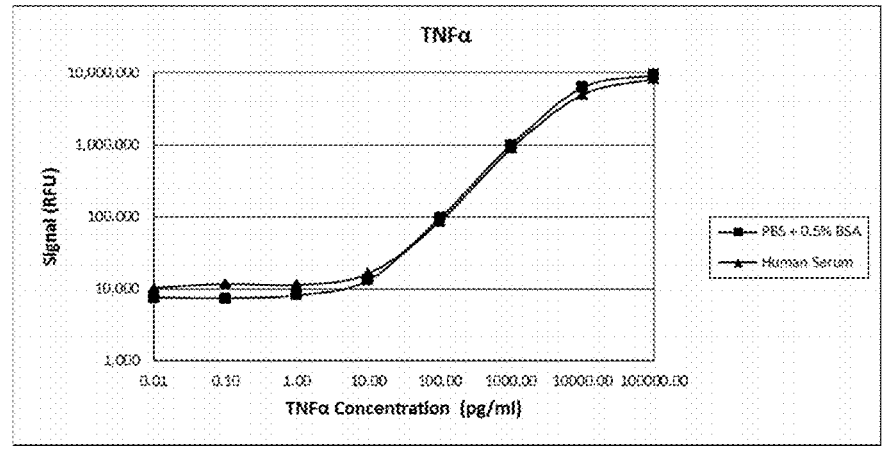

Recombinant Protein Standard Curves in Different Biological Milieu Using the Peptide Conjugate Capture System A demonstration of the use of the single-incubation ELISA assay format for the detection of three recombinant human proteins diluted in human serum is provided in FIG. 11. EGF, IL-2 and TNFα were measured in PBS/0.5% BSA and human serum. Detection limits of ≤10 pg/mL were ascertained for each assay in PBS/0.5% BSA, and similar sensitivity for both IL-2 and TNFα were observed for analyte diluted in human serum. The detection limit for EGF in human serum could not be detected due to the presence of a high level of endogenous EGF, which was confirmed using a standard commercial EGF ELISA kit (R&D Systems, data not shown). FIG. 11 shows the mean and standard deviations for the duplicate data points for each target analyzed.

This data illustrates that the single-incubation ELISA assay format was robust to measuring analytes in different biological milieu. The assay clearly demonstrates efficacy for several different targets in serum, whereby the assay components are incubated concurrently. The high signal for EGF in human serum is due to the presence of endogenous EGF protein(s) in this medium.

Example 9

Recombinant Protein Standard Curves Using the Peptide Conjugate Capture System in a 10 Min Single-Incubation ELISA Nunc 96 well Maxisorp™ plates were passively coated with an anti peptide tag antibody overnight at 4° C. Plates were washed 3× with PBS-T and blocked with 200 µL/well of a 1% BSA solution in PBS-T (0.05%). Blocking solution was aspirated prior to assay. Analyte (eg 50 µL of recombinant protein) were added to the wells followed by the addition of an antibody antibody mixture (50 µL) containing pre-optimised concentrations of peptide tag conjugated anti-analyte capture antibody and HRP-conjugated anti-analyte detection antibody. Plates were incubated for 10 min before washing 3× with PBS-T. Fluorescent HRP substrate (100 µL) was added to the wells and incubated for 5 mins before measurement of fluorescent product.

Recombinant human proteins EGF, IL-2 and TNFα were prepared in PBS/0.5% BSA at concentrations ranging from 100 ng/mL down to 1 pg/mL and 50 µL/well added to an anti peptide tag antibody ELISA plate. Capture/detection antibody mix for EGF (A), IL-2 (B) and TNFα (C) were added to the appropriate ELISA plate wells and incubated for 10 min. Plates were washed before incubation with HRP substrate for 5 min and detection of the fluorescent product.

Figure 12:
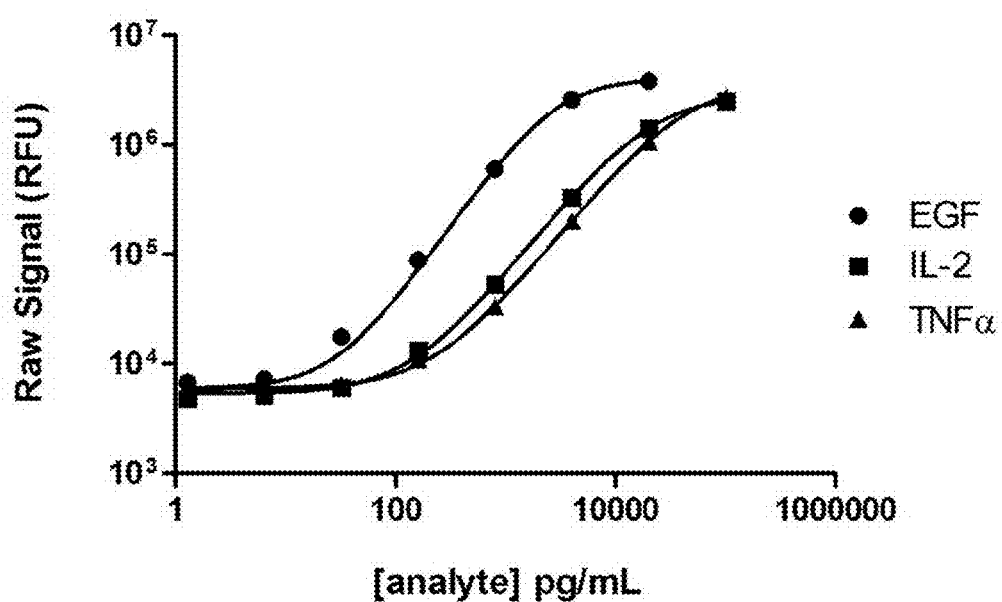
FIG. 12 shows detection of recombinant human EGF, IL-2 and TNFα in a 15 min total assay time. Peptide-capture antibody conjugates, and HRP-detection antibody conjugates specific for each of EGF (●), IL-2 (■) and TNFα (▲) were prepared. Recombinant EGF, IL-2 or TNFα were prepared at concentrations ranging from 100 ng/mL to 10 fg/mL, in PBS/0.5% BSA, and 50 μL/well of each analyte was added to an ELISA assay plate coated with an anti-peptide antibody. The assays were initiated by addition of mixtures containing both specific antibodies for each of EGF, IL-2 or TNFα to the appropriate ELISA plate wells. The assays were incubated for 10 min, then subjected to a wash cycle. After the wash cycle, HRP substrate was added to the wells, and the plates were incubated for 5 min in the dark. The fluorescent signal in the wells was measured at 540ex/590em nm.

FIG. 12 shows the detection of three recombinant human proteins using a 10 min single-incubation ELISA assay format on an anti peptide tag antibody coated ELISA plate. EGF, IL-2 and TNFα standard curves were measured successfully in PBS/0.5% BSA with detection limits of ≤32 pg/mL ascertained for each assay. This data illustrated that the simplified peptide conjugate capture/single-incubation ELISA assay format was amenable to measuring multiple analytes on the same plate in as little as 10 minutes. As can be seen, in the 10 minute single-incubation ELISA the assay was still able to efficiently detect the three analytes, even at a concentration of the analytes less than 100 pg/ml.

Example 10

Intra-Plate Variation

Figure 13:
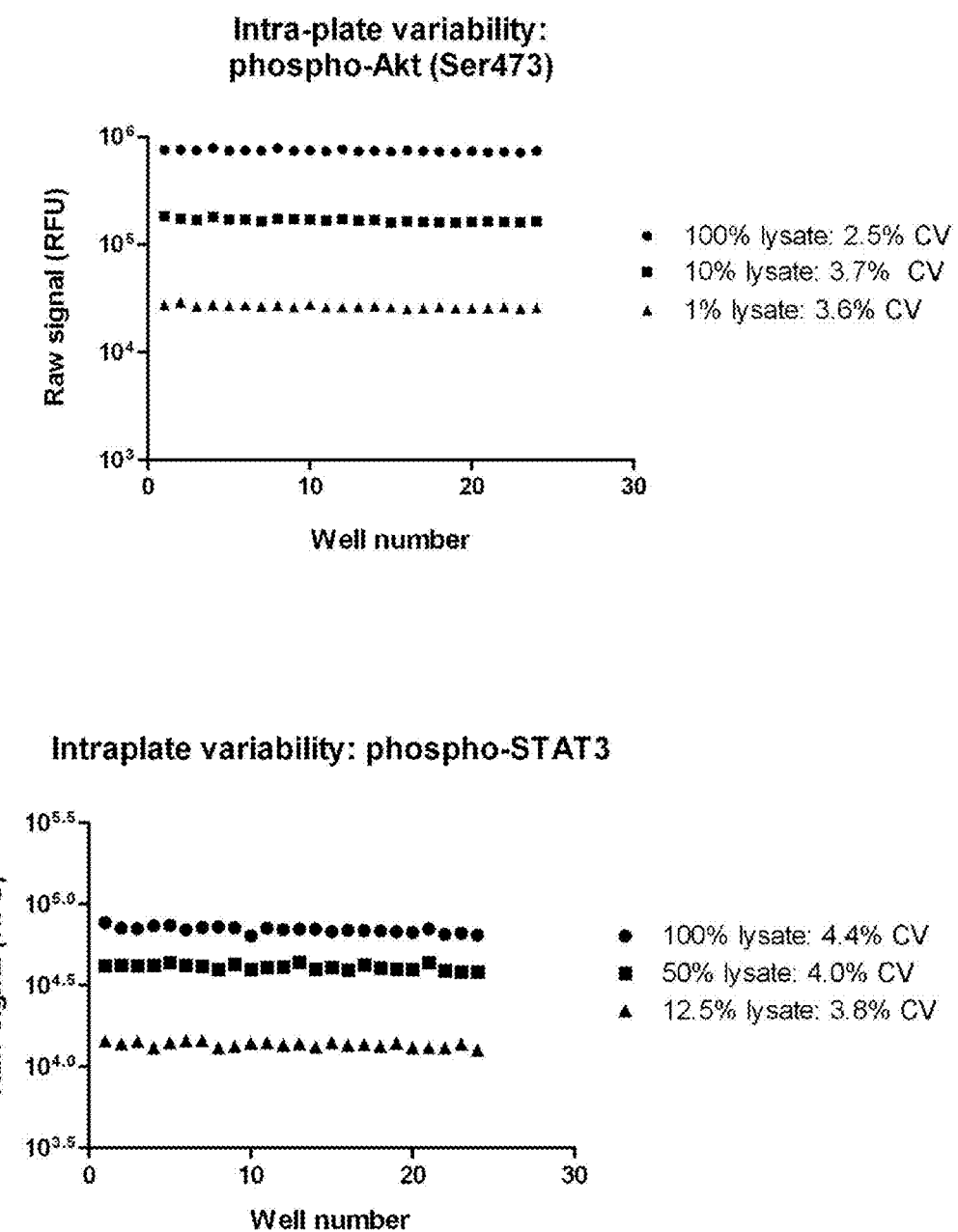
FIG. 13 shows intra-plate variation observed for 2 separate single-incubation ELISAs for either phospho-AKT (pSer473) or phospho-STAT3.

FIG. 13 shows intra-plate variation observed for 2 separate single-incubation ELISAs for either phospho-AKT (pSer473) or phospho-STAT3. For each target, cellular lysate was diluted to 3 different concentrations using 1× Lysis buffer as indicated, and added to 24 replicate wells of a 96-well streptavidin-coated microplate. To initiate the assay reaction, for either target, a mixture of the biotin-conjugated capture antibody, and the HRP-conjugated detection antibody were added to the lysates, and incubated for 1 hour. The wells were subjected to a standard wash cycle for each assay. After the wash cycle, QuantaRed™ HRP substrate was added to the wells, and each plate was incubated for 10 min in the dark. The fluorescent signal in the wells was measured at 550ex/600em nm. FIGS. 13A and 13B show the data points at each lysate concentration analyzed, for phospho-AKT and phospho-STAT3, respectively. The coefficient of variation (CV %) for each analyte concentration was calculated by dividing the standard deviation observed over the 24 wells at each concentration, by the mean of the 24 wells at the same concentration, and transforming this fraction to a percentage value. Typically, a value of less than 10% is desired for many assays, for example, in certain high quality assays, and the data presented here demonstrates suitable low intra-plate variability characteristics.

Example 11

Detection of TNFα

Figure 14:
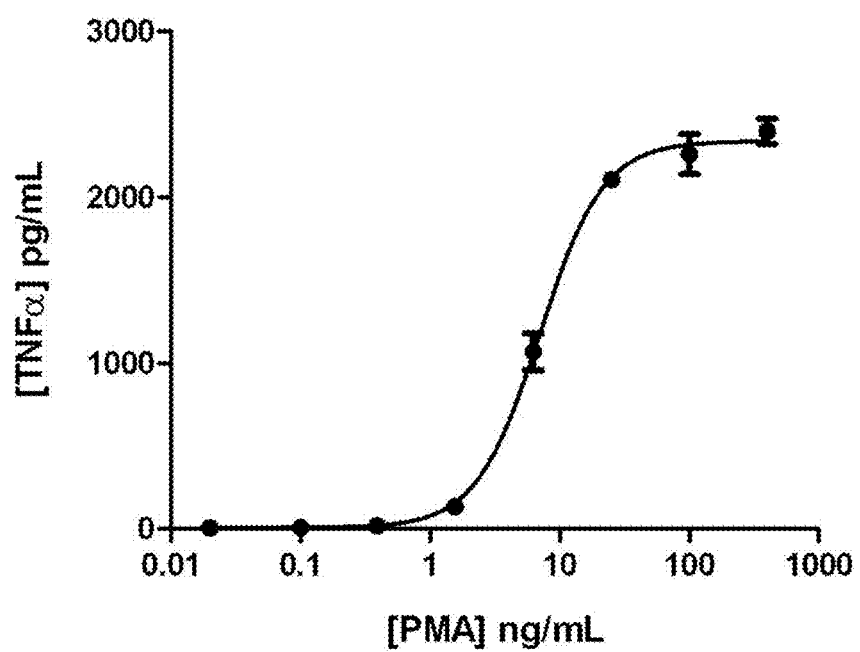
FIG. 14 shows detection of TNFα in tissue culture supernates.

FIG. 14 shows detection of TNFα in tissue culture supernates. THP-1 cells were seeded into 96-well tissue culture microplates in RMPI cell culture medium containing 10% (v/v) foetal bovine serum and various other standard cell culture additives. The cells were then treated with a various concentrations of PMA diluted in the same medium, and incubated overnight in a humidified 37° C. incubator. The following day 50 μL of medium was aspirated from the cell culture wells, and added to the wells of a peptide-coated 96-well assay plate. The assay reaction was initiated by the addition of 50 μL of an antibody mixture containing the capture antibody-peptide conjugate, and the detection antibody-HRP conjugate, and incubated for 1 hour. The wells were subjected to a standard wash cycle for each assay. After the wash cycle, fluorescent HRP substrate was added to the wells, and each plate was incubated for 10 min in the dark. The fluorescent signal in the wells was measured at 540ex/590em nm, and quantitated using a standard curve generated against the same target. FIG. 14 shows the mean and standard deviations for the duplicate data points for each target analyzed. In this Figure, the assay demonstrates efficient detection of specific target analyte in tissue culture supernates using the certain embodiments, whereby the assay components are incubated concurrently.

Example 12

Detection of Phospho-AKT (pSer473) or Phospho-ERK in a 25 Min Total Assay Time

Figure 15A:
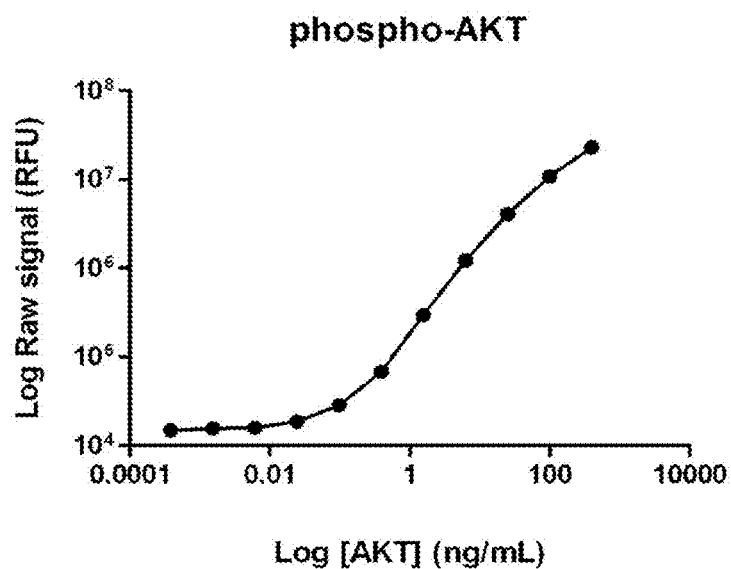
FIGS. 15A and 15B show the data points at each analyte concentration analyzed, for phospho-AKT and phospho-ERK, respectively. Both assays demonstrated sensitivity to less than 1 ng/mL.
Figure 15B:
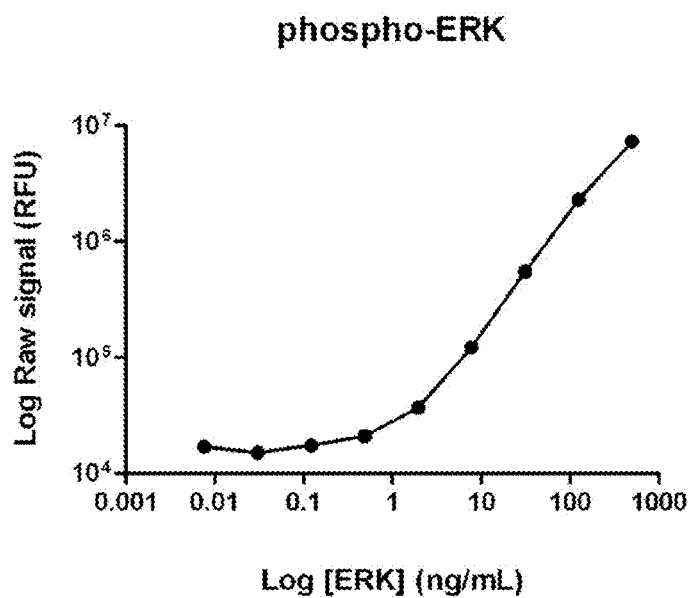

FIG. 15 shows detection of either phospho-AKT (pSer473) or phospho-ERK in a 25 min total assay time. For each target, recombinant active (A) phospho-AKT or (B) phospho-ERK was diluted as indicated, to various concentrations using 1× Lysis buffer containing 0.1% BSA and added to 4 replicate wells of a 96-well streptavidin-coated microplate. To initiate the assay reaction, for either target, a mixture of the biotin-conjugated capture antibody, and the HRP-conjugated detection antibody were added to the lysates, and incubated for 1 hour. The wells were subjected to a standard wash cycle for each assay. After the wash cycle, QuantaRed™ HRP substrate was added to the wells, and each plate was incubated for 10 min in the dark. The fluorescent signal in the wells was measured at 550ex/600em nm. FIGS. 15A and 15B show the data points at each analyte concentration analyzed, for phospho-AKT and phospho-ERK, respectively. Both assays demonstrated sensitivity to less than 1 ng/mL.

Example 13

Detection of IL-2 in Using a ERK Peptide-Anti Peptide Capture Pair

Figure 16:
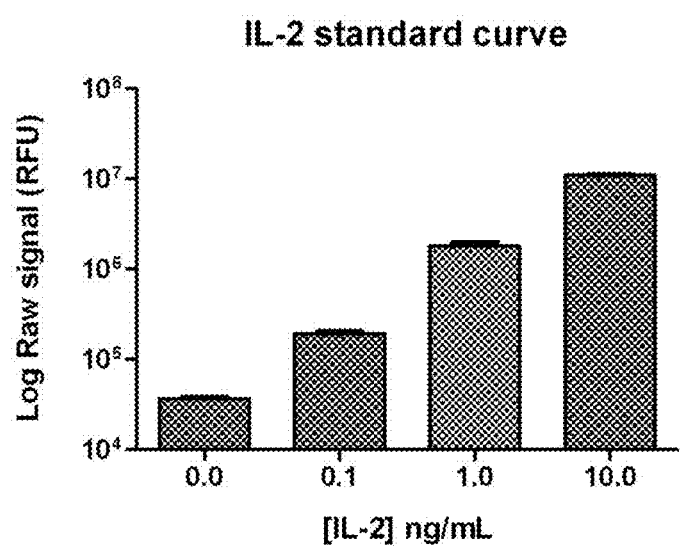
FIG. 16 shows detection of various concentrations of IL-2 using a peptide tag/anti-peptide tag antibody capture system.

FIG. 16 shows detection of IL-2 in using a ERK peptide-anti peptide capture pair. Recombinant interleukin 2 (IL-2) was diluted as indicated, to various concentrations using 1×PBS containing 0.1% BSA and added to duplicate wells of a 96-well anti-ERK-peptide antibody-coated microplate. To initiate the assay reaction, for either target, a mixture of the ERK peptide capture antibody, and the HRP-conjugated detection antibody were added to the lysates, and incubated for 1 hour. The wells were subjected to a standard wash cycle for each assay. After the wash cycle, fluorescent HRP substrate was added to the wells, and each plate was incubated for 10 min in the dark. The fluorescent signal in the wells was measured at 540ex/590em nm. FIG. 16 shows the data points at each analyte concentration analyzed, demonstrating sensitivity to 100 pg/mL or less.

Example 14

General Discussion

The single-incubation ELISA uses an immuno-sandwich format, but with at least one difference. For the single-incubation ELISA assay, both the analyte and the assay reagents are added to the assay microplate at the same time, in solution. After a short incubation period, unbound assay reagents and analytes are washed away, and immuno-complexes containing both antibodies are detected. The single-incubation ELISA allows the user a higher degree of assay flexibility. In contrast to other ELISA formats, in particular sets of examples no target-specific antibodies are present on the assay microplate itself, so assays for several different targets can be performed in different wells on the same microplate. For example, a cellular lysate can be analyzed on the same assay microplate in parallel for p38-MAPK phosphorylation, ERK phosphorylation, AKT phosphorylation and JNK phosphorylation, giving fast, accurate and quantifiable information on key cell signalling events. However, if desired target antibodies may be immobilized on the plate.

The single-incubation ELISA provides the high quality results desired from a sandwich immunoassay, and the assay allows for the use of self-contained kits to conduct the assay.

For example, a kit may contain one or more of the following components:
Capture Antibody Reagent
Detection Antibody Reagent
Lysis Buffer (for example supplied at 5× concentration) containing a mixture of detergents for cellular lysis, and phosphatase inhibitors.
Enhancer Solution—containing factors for enhancing assay performance, such as anti-HAMA components, and target-specific additives to increase assay performance.
ADHP Dilution Buffer—containing cofactors necessary for the HRP-mediated conversion of ADHP to resorufin.
ADHP (for example supplied at 100× concentration)
Wash Buffer (for example supplied at 10× concentration)
Stop Solution—for stopping HRP activity when necessary
Assay Control Lysate
Assay microplate
Assay diluent—for the dilution of concentrated samples

Example 15

General Assay Protocols (i) Protocol for use with samples such as cellular lysates and tissue culture supernates
Assay Protocol
1. Add 50 μl/well of sample to the assay microplate. 50 μl/well assay controls may be added to separate wells if desired.
2. Add 50 μl/well of antibody mix to the wells. Generally a concentration of antibodies in the mix of 50-500 ng/mL is suitable. Cover the microplate and incubate at room temp on a microplate shaker (~300 rpm).
3. Wash wells with 200 μl/well wash buffer (repeat 3 times). After final wash, remove any remaining wash solution from wells. A suitable wash buffer is PBS containing polyethylene glycol sorbitan monolaurate sold under the trademark TWEEN 20.
4. Immediately prior to use, prepare substrate mix. A suitable substrate mix is TMB, ADHP, OPD, or other suitable HRP substrates, diluted with co-factors suitable for mediating their conversion to measurable by-products. Add 100 μl/well of substrate mix. Cover microplate with foil, and incubate for 10 minutes at room temp on a microplate shaker (~300 rpm).
5. Add 10 μl/well stop solution, and mix briefly (5-10 sec) on a microplate shaker. A suitable stop solution is a dilute acid such as HCl, or a strong detergent such as SDS.
6. Read fluorescence signal with a compatible filter set.
(ii) Protocol for serum samples, or other samples that may carry sample-specific interferences
Assay Protocol
1. Add 25 μl/well Enhancer mix. Enhancer mix containing general components for the neutralization of HAMAs, as well other components for the neutralization of target-specific binding proteins carried in serum.
2. Add 50 μl/well of sample to the assay microplate. 50 μl/well assay controls may be added to separate wells if desired.
3. Add 25 μl/well of antibody mix to the wells. Cover the micro plate and incubate for 1 hour at room temp on a microplate shaker (~300 rpm).
3. Wash wells with 200 μl/well wash buffer (repeat 3 times). After final wash, remove any remaining wash solution from wells.
4 Prepare substrate prior to use and add 100 μl/well. Cover microplate with foil, and incubate for 10 minutes at room temp on a microplate shaker (~300 rpm).
5. Add 10 μl/well stop solution, and mix briefly (5-10 sec) on a microplate shaker.
6. Read fluorescence signal with a compatible filter set.

Example 16

Detection of IL-2 in Using a ERK Peptide-Anti Peptide Capture Pair

FIG. 16 shows detection of IL-2 in using a ERK peptide-anti peptide capture pair. Recombinant interleukin 2 (IL-2) was diluted as indicated, to various concentrations using 1×PBS containing 0.1% BSA and added to duplicate wells of a 96-well anti-ERK-peptide antibody-coated microplate. To initiate the assay reaction, for either target, a mixture of the ERK peptide capture antibody, and the HRP-conjugated detection antibody were added to the lysates, and incubated for 1 hour. The wells were subjected to a standard wash cycle for each assay. After the wash cycle, fluorescent HRP substrate was added to the wells, and each plate was incubated for 10 min in the dark. The fluorescent signal in the wells was measured at 540ex/590em nm. FIG. 16 shows the data points at each analyte concentration analyzed, demonstrating sensitivity to 100 pg/mL or less.

Example 17

Figure 17:
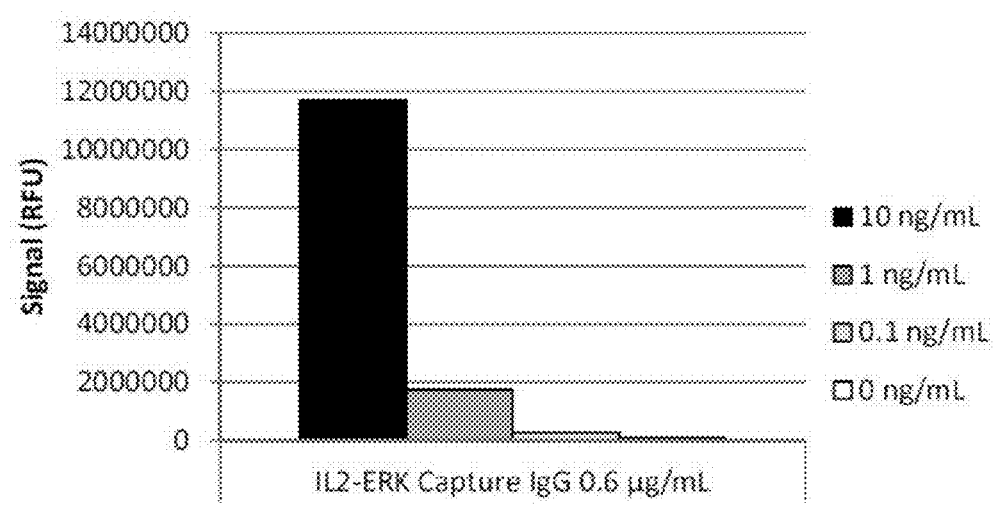
FIG. 17 shows detection of various concentrations of IL-2 using a peptide tag anti peptide tag antibody capture system.

Detection of Various Concentrations of IL-2 Using a Peptide Tag Anti Peptide Tag Antibody Capture System FIG. 17 shows detection of various concentrations of IL-2 using a peptide tag anti peptide tag antibody capture system.
Antibodies were generated in mice as monoclonal antibodies to a 23 amino acid peptide, KRITVEEALAHPYLEQYY-DPTDE (SEQ ID NO. 2), a sequence derived from the carboxy terminus of the human ERK proteins (ERK C-term peptide). Purified antibodies (TGR, 12D4) to this peptide were passively coated onto a maxisorb Nunc immunoassay plate, and the plate then blocked against further non-specific protein attachment. The ERK C-term peptide was also used to conjugate to antibodies to the human IL-2 protein (R&D Systems), so that the peptide would act to anchor this antibody to the plate surface. A second IL-2 antibody (R&D Systems) was conjugated to horse radish peroxidase (HRP) to be used as the reporter antibody. Recombinant human IL-2 was mixed with PBS/BSA (0.1%) at various concentrations shown, and to these solutions were added the IL-2 antibodies. After an hour incubation, the wells were washed with a wash buffer, and fluorescent HRP substrate added for 10 min, followed by reading of the plate at 540/590 nm ex/em wavelengths in a plate reader.
It can be seen that the assay system measured the concentrations of IL-2 present in each sample and that the variation between samples was low as indicated by the small error bars.

Example 18

Figure 18:
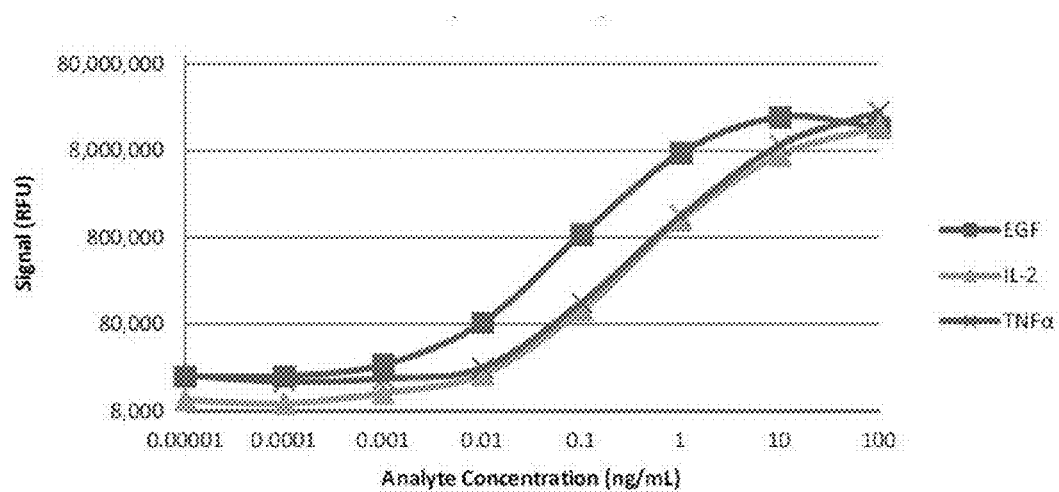
FIG. 18 shows detection of various concentrations of EGF, IL-2 & TNFα using a peptide tag anti peptide tag antibody capture system.

Detection of Various Concentrations of EGF, IL-2 & TNFα Using a Peptide Tag Anti Peptide Tag Antibody Capture System FIG. 18 shows detection of various concentrations of EGF, IL-2 & TNFα using a peptide tag anti peptide tag antibody capture system.
Antibodies specific to the peptide DYKDDDDK (SEQ ID NO. 1; Sigma, catalog number F1804) were passively coated onto a maxisorb Nunc immunoassay plate at 5 μg/mL overnight in PBS, and the plate then blocked against further non-specific protein attachment. The peptide DYKDDDDK (SEQ ID NO. 1) was also used to conjugate to IgG antibodies to the human IL-2 protein (R&D Systems), human EGF or human TNF☐ so that the peptide would act to anchor this antibody to the plate surface. A second detectable antibody to each analyte (R&D Systems) was also conjugated to horse radish peroxidase (HRP) to be used as the reporter antibody. EGF, IL-2 & TNFα peptide (C-terminal acid) capture IgG's & and their respective HRP detection were IgG's prepared in reaction buffer. Pure analytes as standards were diluted in PBS/BSA (0.5%) at various concentrations shown. Analyte (50 μL/well) was added to the coated plate and then added 50 μL/well of corresponding antibody mix (Capture 200 ng/mL; detection 50 ng/mL). After an hour incubation with shaking, the wells were washed three time with a wash buffer, and fluorescent HRP substrate (ADHP) added for 10 min, followed by reading of the plate at 540/590 nm ex/em wavelengths in a plate reader. The data shows the sensitive detection of each of EGF, IL-2 and TNF☐ in separate wells of a microtitre plate using a single-wash, peptide tag antibody capture system.

Example 19

Figure 19:
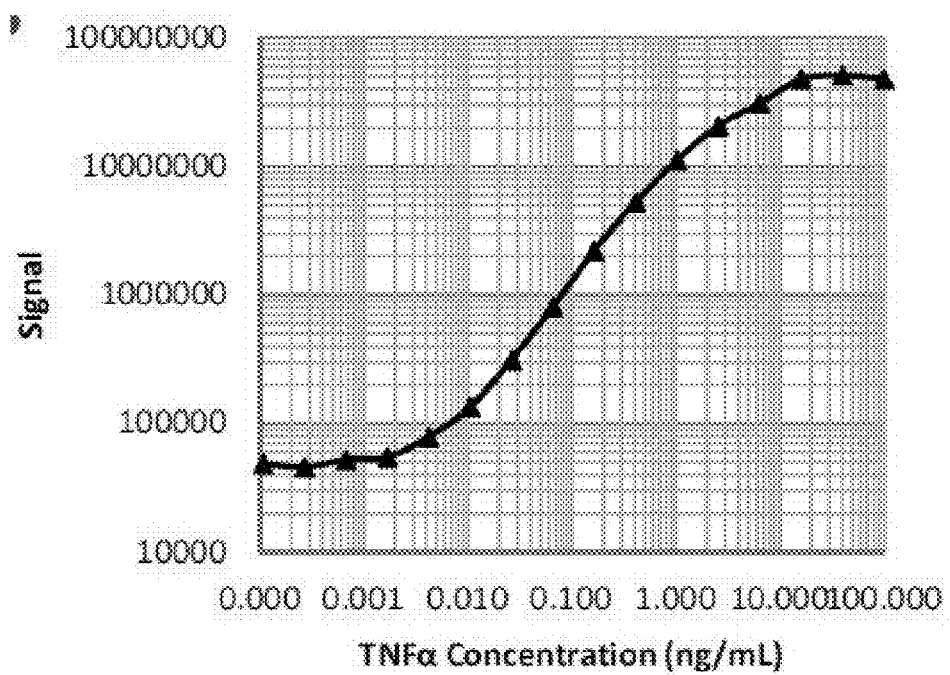
FIG. 19 shows the signal obtained for various concentrations of analyte using a peptide tag anti peptide tag antibody capture system.

Detection of Various Concentrations of Analyte Using a Peptide Tag Anti Peptide Tag Antibody Capture System FIG. 19 shows the signal obtained for various concentrations of analyte using a peptide tag anti peptide tag antibody capture system.

Antibodies were generated in mice as monoclonal antibodies to the peptide DYKDDDDK (SEQ ID NO. 1). Purified antibodies to this peptide were coated onto a maxisorb Nunc immunoassay plate at 10 ug/ml, and the plate then blocked against further non-specific protein attachment. The peptide DYKDDDDK (SEQ ID NO. 1) was also used to conjugate to antibodies to the human TNFα protein (R&D Systems), so that the peptide would act to anchor this antibody to the plate surface. A second TNF☐ antibody (R&D Systems) was conjugated to horse radish peroxidase (HRP) to be used as the reporter antibody. TNFα was mixed with PBS/BSA (0.5%) at various concentrations shown, and to these solutions were added the IL-2 antibodies (Capture 200 ng/mL; detection 50 ng/mL). After an hour incubation with shaking, the wells were washed with a wash buffer, and fluorescent HRP substrate added for 10 min, followed by reading of the plate at 540/590 nm ex/em wavelengths in a plate reader. The data shows that the use of a peptide tag antibody capture system, whereby in this case the peptide tag was DYKDDDDK, and the system was a single-wash ELISA format, enabled the sensitive measurement of TNFα with a total assay time of approximately 1 hour.

Example 20

Figure 20:
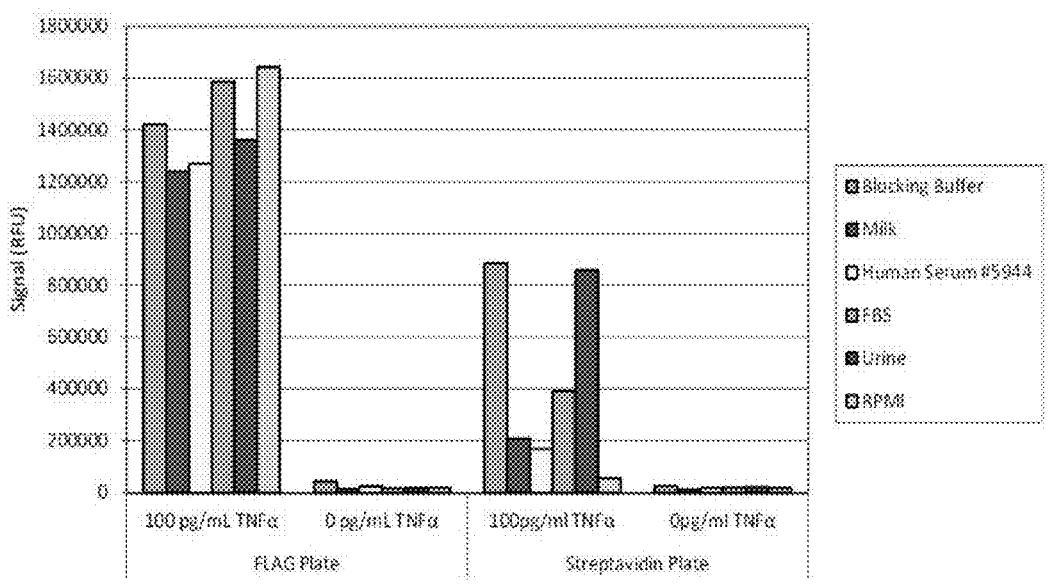
FIG. 20 shows a comparison of a biotin-streptavidin capture system to a peptide tag-anti-peptide antibody capture system in various biological milieu.

Comparison of a Biotin-Streptavidin Capture System to a Peptide Tag-Anti-Peptide Antibody Capture System in Various Biological Milieu FIG. 20 shows a comparison of a biotin-streptavidin capture system to a peptide tag-anti-peptide antibody capture system in various biological milieu.

Antibodies were generated in mice as monoclonal antibodies to the peptide DYKDDDDK (SEQ ID. NO. 1). Purified antibodies to this peptide were coated onto a maxisorb Nunc immunoassay plate at 10 μg/ml overnight in carbonate buffer, and the plate washed and then blocked against further non-specific protein attachment. Separately, a commercial streptavidin-coated plate (Nunc Immobiliser) was used for biotin-conjugated antibodies assays. The peptide DYKDDDDK (SEQ ID NO. 1) was used to conjugate to antibodies to the human TNFα protein (R&D Systems), so that the peptide would act to anchor this antibody to the plate surface to which had been coated antibodies to this peptide. Separately, antibodies to the human TNFα protein (R&D Systems), were also linked with biotin, so that this would act to anchor this antibody to the plate surface to which had been coated streptavidin. A second species of TNFα antibody (R&D Systems) was conjugated to horse radish peroxidase (HRP) to be used as the reporter antibody. TNFα was mixed with various media (blocking buffer, milk, human serum, FBS, urine or RPMI) at 100 pg/mL or not added at all, and to these solutions were added either to the TNFα antibodies linked with biotin (Capture 750 ng/mL; detection 50 ng/mL) or peptide DYKDDDDK (SEQ ID NO. 1) (Capture 300 ng/mL; detection 50 ng/mL), and the HRP-linked TNFα antibodies. After an hour incubation, the wells were washed with a wash buffer, and fluorescent HRP substrate ADHP added for 10 min, followed by reading of the plate at 540/590 nm ex/em wavelengths in a plate reader. It can be seen from the data that the peptide tag-anti-peptide antibody capture systems was superior to the biotin-streptavidin system in detecting analytes, particularly when analytes were present in particular media. Of special note are the inhibitory effects on the assay of TNFα present in milk, serum, FBS and RPMI when using the biotin-streptavidin system, reflecting the presence of biotin in these samples that interferes with this capture system.

Example 21

Figure 21:
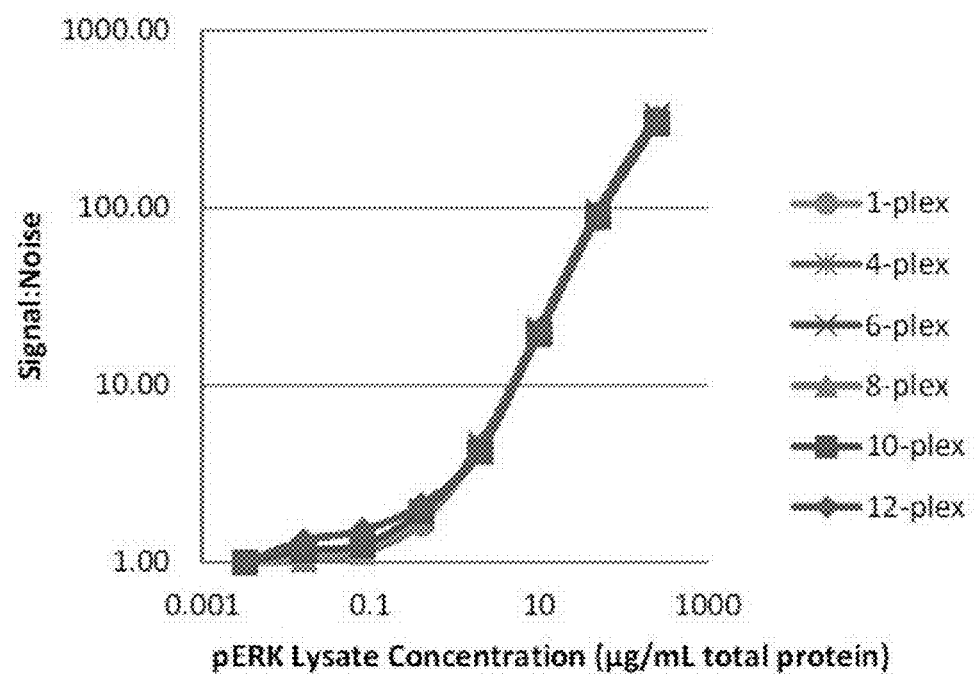
FIG. 21 shows that a streptavidin biotin capture system utilizing an antibody capture agent and an antibody detectable agent is not affected by increasing concentrations of irrelevant antibodies. shows the data from FIG. 21 has been normalised in terms of signal:noise, where noise is the signal of the immunocomplex obtained for each condition compared to the signal obtained in the absence of analyte.

Streptavidin Biotin Capture Systems Utilizing an Antibody Capture Agent and an Antibody Detectable Agent is not Affected by Increasing Concentrations of Irrelevant Antibodies FIG. 21 shows that a streptavidin biotin capture system utilizing an antibody capture agent and an antibody detectable agent is not affected by increasing concentrations of irrelevant antibodies.

Nunc Immobiliser plates, coated with streptavidin, were used in an assay to determine capacity of p-ERK antibody binding and p-ERK analyte measurement. Antibodies to the phosphorylation site of the ERK protein (TGR, Thr202/Tyr204) were linked with biotin, so that this would act to anchor this antibody to the plate surface to which has been coated streptavidin. Separately, a second ERK antibody (Santa Cruz) was linked to horse radish peroxidase (HRP) to act as a reporter antibody. Samples containing cellular lysates in which the p-ERK protein was present at various concentrations were then mixed with the ERK antibodies either in the absence (1-plex) or presence (4-12-plex) of increasing numbers of pairs of irrelevant antibodies at the same concentration as the ERK antibodies, such that one of the pair of the irrelevant antibodies was also biotinylated in the same way and extent as the ERK antibody. After 1 hour, the wells were washed with a wash buffer, and fluorescent HRP substrate ADHP added for 10 min, followed by reading of the plate at 540/590 nm ex/em wavelengths in a plate reader. Results are presented as absolute fluorescence signal.

FIG. 21 shows the data normalised in terms of signal:noise, where noise is the signal of the immunocomplex obtained for each condition compared to the signal obtained in the absence of analyte.

It can be seen from these graphs that the single-wash assay system with both antibodies being present with the analyte, in this case using the biotin-streptavidin pair, can use low concentrations of Capture antibodies, allowing the presence of up to 12 pairs of unrelated tagged antibodies to be present without there being any assay interference.

Example 22

Figure 22A:
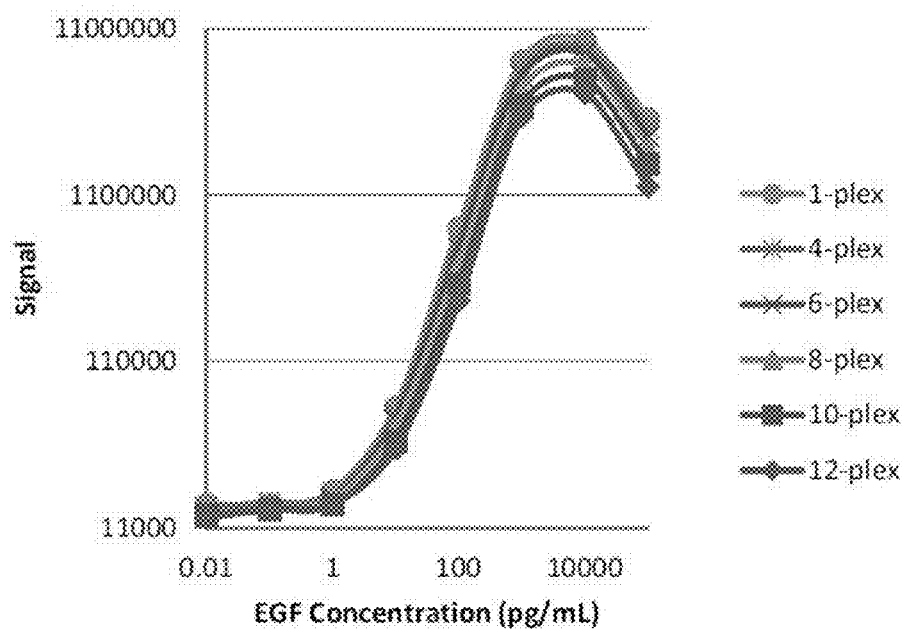
FIG. 22A shows that anti peptide tag antibody-peptide capture system utilizing an antibody capture agent and an antibody detectable agent is not affected by increasing concentrations of irrelevant antibodies.

Anti Peptide Tag Antibody-Peptide Capture Systems Utilizing an Antibody Capture Agent and an Antibody Detectable Agent is not Affected by Increasing Concentrations of Irrelevant Antibodies FIG. 22A shows that anti peptide tag antibody-peptide capture system utilizing an antibody capture agent and an antibody detectable agent is not affected by increasing concentrations of irrelevant antibodies Antibodies were generated in mice as monoclonal antibodies to the peptide DYKDDDDK (SEQ ID NO. 1). Purified antibodies to this peptide were coated onto a maxisorb Nunc immunoassay plate, and the plate then blocked against further non-specific protein attachment. Antibodies to the human EGF protein (R&D Systems) were linked with the peptide DYKDDDDK (SEQ ID NO. 1), so that this would act to anchor this antibody to the plate surface to which has been coated streptavidin. Separately, a second EGF antibody (R&D Systems) was linked to horse radish peroxidase (HRP)

to act as a reporter antibody. Samples containing EGF at various concentrations were then mixed with the EGF antibodies either in the absence (1-plex) or presence (4-12-plex) of increasing numbers of pairs of irrelevant antibodies at the same concentration as the EGF antibodies, such that one of the pair of the irrelevant antibodies was also linked with the peptide DYKDDDDK (SEQ ID NO. 1) in the same way and extent as the EGF antibody. After 1 hour, the wells were washed with a wash buffer, and fluorescent HRP substrate ADHP added for 10 min, followed by reading of the plate at 540/590 nm ex/em wavelengths in a plate reader. Results are presented as absolute fluorescence signal.

Figure 22B:
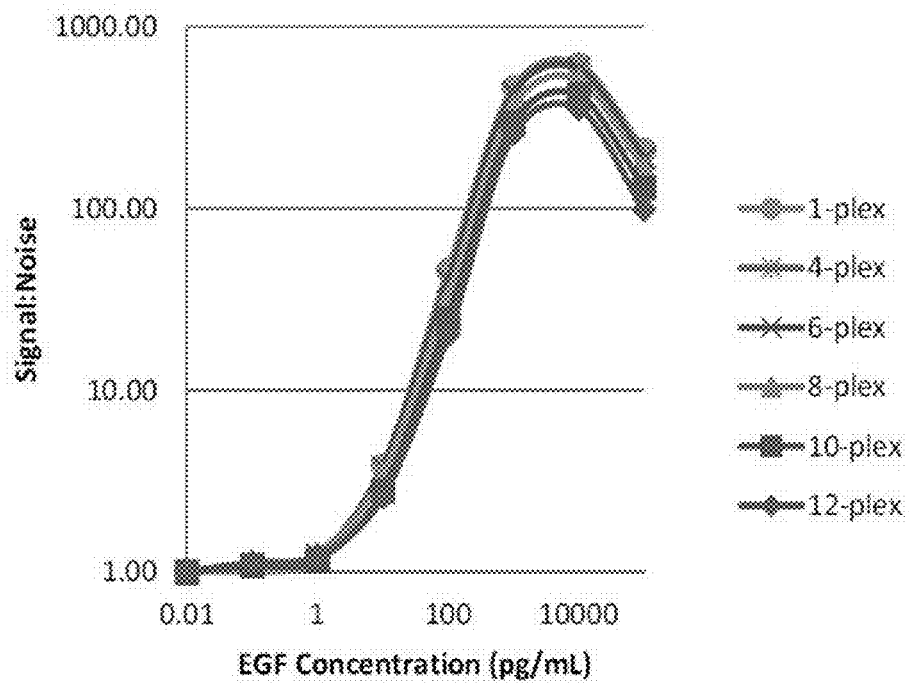
FIG. 22B shows the data from FIG. 22A has been normalised in terms of signal:noise, where noise is the signal of the immunocomplex obtained for each condition compared to the signal obtained in the absence of analyte.

FIG. 22B shows the data from FIG. 22A normalised in terms of signal:noise, where noise is the signal of the immunocomplex obtained for each condition compared to the signal obtained in the absence of analyte.

It can be seen from these graphs that the single-wash assay system with both antibodies being present with the analyte, in this case using the peptide-anti-peptide antibody pair, can use low concentrations of Capture antibodies, allowing the presence of up to 12 pairs of unrelated tagged antibodies to be present without there being any assay interference.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Also, it must be noted that, as used herein, the singular forms "a", "an" and "the" include plural aspects unless the context already dictates otherwise.

The invention claimed is:

1. A method for detecting an analyte, comprising: covalently binding an antibody capture agent with a plurality of peptide tags to form a tagged antibody capture agent;
   forming an analyte complex comprising the analyte bound to the tagged antibody capture agent and to a detectable agent separately;
   introducing the analyte complex to an anti-peptide antibody immobilized on a substrate;
   immobilizing the analyte complex to the substrate by binding at least one of the plurality of peptide tags with the anti-peptide antibody; and
   detecting the analyte by detection of the detectable agent.

2. The method according to claim 1, wherein the analyte is a non-nucleic acid analyte.

3. The method according to claim 1, wherein the tagged antibody capture agent complexes with a non-nucleic acid portion of the analyte.

4. The method according to claim 1, wherein the tagged antibody capture agent binds with the analyte substantially exclusive of nucleic acid-nucleic acid interactions.

5. The method according to claim 1, wherein at least one of the plurality of peptide tags is not naturally occurring.

6. The method according to claim 1, wherein the covalently binding comprises cross-linking.

7. The method according to claim 6, wherein the cross-linking comprises covalent conjugation by primary amines in the antibody capture agent.

8. The method according to claim 1, wherein the tagged antibody capture agent is in solution.

9. The method according to claim 8, wherein the solution has a tagged antibody capture agent concentration in the range from 50 to 500 ng/ml.

10. The method according to claim 1, wherein the tagged antibody capture agent has a dissociation constant, Kd, of between $10^{-6}$ and $10^{-12}$ M.

11. The method according to claim 1, wherein the detectable agent is in solution.

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: FLAG tag sequence

<400> SEQUENCE: 1

Asp Tyr Lys Asp Asp Asp Asp Lys
1               5

<210> SEQ ID NO 2
<211> LENGTH: 23
<212> TYPE: PRT
<213> ORGANISM: Homo sapiens

<400> SEQUENCE: 2

Lys Arg Ile Thr Val Glu Glu Ala Leu Ala His Pro Tyr Leu Glu Gln
1               5                   10                  15

Tyr Tyr Asp Pro Thr Asp Glu
            20
```

12. The method according to claim 1, wherein the detectable agent comprises a detectable tag.

13. The method according to claim 12, wherein the detectable tag comprises one or more of an enzyme, a fluorophore, and a lanthanide ion.

14. The method according to claim 1, wherein the anti-peptide antibody is bound to the substrate via a non-covalent attachment.

15. The method according to claim 1, wherein the substrate is at least partially blocked.

16. The method according to claim 1, wherein the complexing occurs in a solution.

17. The method according to claim 16, wherein the solution has a tagged antibody capture agent concentration in the range from 50 to 500 ng/ml.

18. The method according to claim 1, wherein the analyte is provided in a biological sample.

19. The method according to claim 18, wherein the sample has an analyte concentration of 100 ng/ml or less.

20. The method according to claim 18, wherein the sample comprises one or more proteins separate from the analyte wherein the one or more proteins have a total concentration of more than 0.01 mg/ml.

21. The method according to claim 19, wherein the sample comprises one or more proteins separate from the analyte wherein the one or more proteins have a total concentration of more than 0.01 mg/ml.

22. The method according to claim 18, wherein the sample comprises one or more of blood, serum, urine, milk, cell lysate, and a derivative thereof.

23. The method according to claim 21, wherein the sample comprises one or more of blood, serum, urine, milk, cell lysate, and a derivative thereof.

24. The method according to claim 1, wherein the complexing and the immobilizing occur in a single reaction vessel, and more than one analyte is detected in the single reaction vessel.

25. The method according to claim 1, wherein the complexing occurs in a first reaction vessel and the immobilizing occurs in a second reaction vessel.

26. The method according to claim 1, wherein the immobilizing comprises incubating.

27. The method according to claim 26, wherein the analyte is detected in less than 120 minutes after the incubating is initiated.

28. The method according to claim 1, further comprising one or more washings after immobilizing.

29. The method according to claim 28, wherein the one or more washings consists of no more than one washing.

30. The method according to claim 1, wherein the plurality of peptide tags comprises a peptide comprising the amino acid sequence DYKDDDDK (SEQ ID NO. I).

* * * * *

UNITED STATES PATENT AND TRADEMARK OFFICE
CERTIFICATE OF CORRECTION

PATENT NO. : 9,086,407 B2
APPLICATION NO. : 13/436764
DATED : July 21, 2015
INVENTOR(S) : Antony James Sheehan et al.

It is certified that error appears in the above-identified patent and that said Letters Patent is hereby corrected as shown below:

In the claims

Column 48, lines 1-13 should read

1. A method for detecting an analyte, comprising:
covalently binding an antibody capture agent with a plurality of peptide tags to form a tagged antibody capture agent;
forming an analyte complex comprising the analyte bound to the tagged antibody capture agent and separately to a detectable agent;
introducing the analyte complex to an anti-peptide antibody immobilized on a substrate;
immobilizing the analyte complex to the substrate by binding at least one of the plurality of peptide tags with the anti-peptide antibody; and
detecting the analyte by detection of the detectable agent.

Signed and Sealed this
Seventeenth Day of November, 2015

Michelle K. Lee
*Director of the United States Patent and Trademark Office*